United States Patent [19]

Bruice et al.

[11] Patent Number: 5,698,674
[45] Date of Patent: Dec. 16, 1997

[54] TRIHETEROCYCLIC PEPTIDES CAPABLE OF BINDING THE MINOR AND MAJOR GROOVES OF DNA

[75] Inventors: Thomas C. Bruice, Santa Barbara; Kenneth A. Browne, Goleta; Gong-Xin He, Fremont, all of Calif.

[73] Assignee: The Regents of the University of California, Oakland, Calif.

[21] Appl. No.: 226,934

[22] Filed: Apr. 13, 1994

[51] Int. Cl.$^6$ .......................... C07K 5/08; C07D 401/00; C07D 255/02; C07D 207/00
[52] U.S. Cl. .......................... 530/331; 540/474; 546/256; 546/272.7; 458/518
[58] Field of Search .......................... 548/400, 518, 548/557, 561, 564, 566; 514/403, 2, 183, 359, 408, 426, 427; 530/331; 540/474; 546/256, 272.7

[56] References Cited

PUBLICATIONS

Blasko, A., Browne, K.A., He, G.-X, Bruice, T.C., "Microgonotropens and Their Interactions with DNA. 3.[1] Structutal Analysis of the 1:1 Complex of d(CG-CAAATTTGCG)$_2$ and Dien-Microgonotropen-c by 2D NMR Spectroscopy and Restrained Molecular Modeling," *J. Am. Chem. Soc.* 115:7080 (1993) (Exhibit 1).

Coll, M., et al., "A Bifurcated hydrogen-bonded conformation in the d(AT) base pairs of the DNA dodecamer d(CG-CAAATTTGCG) and its complex with distamycin," *Proc. Natl. Acad. Sci. USA* 84:8385–8389 (1987) (Exhibit 2).

Pelton, J., and Wemmer, D., "Binding Modes of Distamycin A with d(CGCAAATTTGCG)$_2$ Determined by Two–Dimensional NMR," *J. Am. Chem. Soc.* 112:1393–1399, (1990) (Exhibit 3).

Lee, M., et al., "Molecular Recognition between Oligopeptides and Nucleic Acids: Influence of van der Waals Contacts in Determining the 3'–Terminus of DNA Sequences Read by Monocationic Lexitropsins", *J. Am. Chem. Soc.*, 110:3641–3649 (1988) (Exhibit 4).

Dwyer, T., et al., "Design and Binding of a Distamycin A Analog to d(CGCAAGTTGGC) d(GCCAACTTGCG): Synthesis, NMR Studies, and Implications for the Design of Sequence–Specific Minor Groove Binding Oligopeptides," *J. Am. Chem. Soc.*, 114:5911–5919 (1992) (Exhibit 5).

He, G.-X., Browne, K., Groppe, J., Blasko, A., Mei, H.-Y, and Bruice, T., "Microgonotropens and Their Interactions with DNA. 1.[1] Synthesis of the Tripyrrole Peptides Dien-Microgonotropen-a, -b, and -c and Characterization of Their Interactions with dsDNA," *J. Am. Chem. Soc.*, 115:7061–7071 (1993).

Krowicki, K. and Lown, J., "Synthesis of Novel Imidazole-Containing DNA Minor Groove Binding Oligopeptides Related to the Antiviral Antibiotic Netropsin," *J. Org. Chem.* 52:3493–3501 (1987) (Exhibit 7).

Gursky, G., et al., "Synthetic Sequence–specific Ligands," *Cold Spring Harbor Symposium Quant. Biol.*, 47:367–378 (1983) (Exhibit 8).

Kopka, M., Yoon, C., Goodsell, D., Pjura, P., Dickerson, R., "The molecular origin of DNA–drug specificity in netropsin and distamycin," *Proc. Natl. Acad. Sci. USA* 82:1376–1380 (1985) (Exhibit 9).

Bialer, M., Yagen, B., and Mechoulam, R., "A Total Synthesis of Distamycin A, An Antiviral Antibiotic ," *Tetrahedron* 34:2389–2391 (1978) (Exhibit 10).

Lown, J., and Krowicki, K., "Efficient Total Syntheses of the Oligopeptide Antibiotics Netropsin and Distamycin," *J. Org. Chem.* 50:3774–3779 (1985) (Exhibit 11).

Rao, K.E., Bathini, Y., Lown, J.W., "Synthesis of Novel Thiazole–Containing DNA Minor Groove Binding Oligopeptides Related to the Antibiotic Distamycin" *J. Org. Chem.* 55:728–737 (1990) (Exhibit 12).

(List continued on next page.)

Primary Examiner—Mindy Fleisher
Assistant Examiner—Robert Schwartzman
Attorney, Agent, or Firm—Merchant, Gould, Smith, Edell, Welter & Schmidt

[57] ABSTRACT

The present invention provides a triheterocyclic peptide having first, second, and third 5-member heterocyclic moieties having the following formula $CR_3CONH-Q^1-CONH-Q^2-CONH-Q^3-CONH-(CR_3)_S-B$, wherein $Q^1$ is selected from a group consisting of:

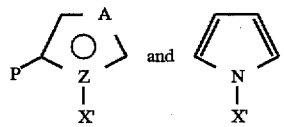

wherein $Q^2$ is selected from a group consisting of:

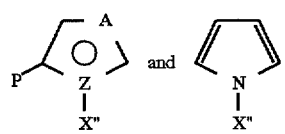

wherein $Q^3$ is selected from a group consisting of:

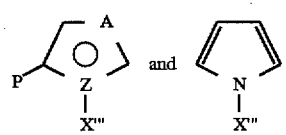

wherein at least one of A and Z is other than C; wherein A is C, N, O, or S; wherein B is $N(CR_3)_n$ or $C(NH_2)_2$; wherein n is an integer from 2 to 10; wherein P is H, a lower alkyl or a halogen; wherein Q1, Q2, and Q3 are the same or different; wherein R is H, a lower alkyl group; wherein S is an integer from 1 to 10; wherein X' represents $CR_3$, $(CR_2)_n$—NRY, or $(CR_2)_n$—$CR_2Y$; wherein X" represents $CR_3$, $(CR_2)_n$—NRY, or $(CR_2)_n$—$CR_2Y$; wherein X'" represents $CR_3$, $(CR_2)_n$—NRY, or $(CR_2)_n$—$CR_2Y$; wherein Y is a polyamine group, and wherein Z is C or N; wherein at least one of X', X", or X'" is other than $CR_3$.

32 Claims, 38 Drawing Sheets

OTHER PUBLICATIONS

Nagasawa, T., et al., "New Agents for t–Butyloxycarbonylation and p–Methoxybenzyl–oxycarbonylation of Amino Acids," *Bull. Chem. Soc. Jpn.* 46:1269–1272 (1973) (Exhibit 13).

Carpino, Louis, and Tsao, J.–H., "The β–(Trimethylsilyl) ethoxycarbonyl Amino–protecting Group," *J.C.S. Chem. Comm.* 358–359 (1978) (Exhibit 14).

Rosowsky, A., and Wright, J.E., "$N^\epsilon$–[[2–(Trimethylsilyl)ethoxy]carbonyl] Derivatives of Tri–L–lysine and Tetra–L–lysine as Potential Intermediates in the Block Polymer Synthesis of Macromolecular Drug Conjugates," *J. Org. Chem.* 54:5551–5558 (1989) (Exhibit 15).

Galas, D.J., and Schmitz, A., "DNAase footprinting: a simple method for the detection of protein–DNA binding specificity," *Nucleic Acids Res.* 5:3157–3170 (1978) (Exhibit 16).

Harshman, K.D., and Dervan, P.B., "Molecular recognition of B–DNA by Hoechst 33258+," *Nucleic Acids Res.* 13:4825–4835 (1985) (Exhibit 17).

Baker, B.F., and Dervan, P.B., "Sequence–Specific Cleavage of DNA by N–Bromoacetyldistamycin. Product and Kinetic Analyses," *J. Am. Chem. Soc.* 111:2700–2712 (1989) (Exhibit 18).

Burkhoff, A.M. and Tullius, T.D., "The Unusual Conformation Adopted by the Adenine Tracts in Kinetoplast DNA" *Cell* 48:935–943 (1987) (Exhibit 19).

Van Dyke, M.W., Hertzberg, R.P., Dervan, P.B., "Map of distamycin, netropsin, and actinomycin binding sites on heterogeneous DNA:DNA cleavage–inhibition patterns with methidiumpropyl–EDTAFe(II)," *Proc. Natl. Acad. Sci. USA* 79:5470–5474 (1982) (Exhibit 20).

Dabrowiak, J.C., and Goodisman, J., "Quantitative Footprinting Analysis of Drug–DNA Interactions," In *Chemistry & Physics of DNA–Ligand Interactions*, Kallenbach, N.R., Ed., Adenine Press: New York, 1989, pp. 143–174 (Exhibit 21).

Goodisman, J., and Dabrowiak, J.C., "Structural Changes and Enhancements in DNase I Footprinting Experiments," *Biochemistry* 31:1058–1064 (1992) (Exhibit 22).

Browne, K., He, G.–X., Bruice, T.C., "Microgonotropens and Their Interactions with DNA. 2.[1] Quantitative Evaluation of Equilibrium Constants for 1:1 and 2:1 Binding of Dien–Microgonotropen–a, –b, and –c as Well as Distamycin and Hoechst 33258 to d(GGCGCAAATTTGGCGG)/d(C-CGCCAAATTTGCGCC)," *J. Am. Chem. Soc.* 115:7072–7079 (1993) (Exhibit 23).

Wu, Hen–Ming, and Crothers, D.M., "The locus of sequence–directed and protein–induced DNA bending," *Nature* 308:509–513 (1984) (Exhibit 24).

Levene, S.D., et al., "Bending and Flexibility of Kinetoplast DNA," *Biochemistry* 25:3988–3995 (1986) (Exhibit 25).

Thompson, J.F., and Landy, A., "Empirical estimation of protein–induced DNA bending angles: application to λ site–specific recombination complexes," *Nucleic Acids Res.* 16:9687–9705 (1988) (Exhibit 26).

States, D.J., Haberkorn, R.A., Ruben, D.J., "A Two–Dimensional Nuclear Over–hauser Experiment with Pure Absorption Phase in Four Quadrants," *Journal of Magnetic Resonance* 48:286–292 (1982) (Exhibit 27).

Kessler, H., et al., "Separation of Cross–Relaxation and J Cross–Peaks in 2D Rotating–Frame NMR Spectroscopy," *J. Am. Chem. Soc.* 109:607–609 (1987) (Exhibit 28).

Patel, D.J., Shapiro, L., "Molecular recognition in noncovalent antitumor agent–DNA complexes: NMR studies of the base and sequence dependent recognition of the DNA minor groove by netropsin," *Biochimie* 67:887–915 (1985) (Exhibit 29).

Patel, D.J., Shapiro, L., "Sequence–Dependent Recognition of DNA Duplexes," *J. Biol. Chem.* 261:1230–1240 (1986) (Exhibit 30).

Patel, D.J., Shapiro, L., Hare, D., "DNA and RNA: NMR studies of conformations and dynamics in solution," *Q. Rev. Biophys.* 20:35–112 (1987) (Exhibit 31).

Gao, X., Patel, D., "Antitumour drug—DNA Interactions: NMR studies of echin–omycin and chromomycin complexes," *Q. Rev. Biophys.* 22:93–138 (1989).

Zhang, X., Patel, D., "Solution Structure of the Nogalamycin—DNA Complex," *J. Biochemistry* 29:9451–9466 (1990) (Exhibit 33).

Brooks, B.R., Bruccoleri, Olafson, B.D., States, D.J., Swaminathan, S.,Karplus, M., "Charmm: A program for Macromolecular Energy, Minimization, and Dynamics Calculations," *J. Comp. Chem.* 4:187–217 (1983) (Exhibit 34).

Prive, G., Yanagi, K., and Dickerson, R., "Structure of the B–DNA Decamer C–C–A–A–C–G–T–T–G–G and Comparison with Isomorphous Decamers C–C–A–A–G–A–T–T–G–G and C–C–A–G–G–C–C–T–G–G," *J. Mol. Biol.* 217:177–199 (1991) (Exhibit 35).

Blasko, A., Bruice, T.C., "Stoichiometry and structure of complexes of DNA oligomers with Microgonotropens and distamycin by $^1$H NMR spectroscopy and molecular modeling," *Proc. Natl. Acad. Sci. USA*, 90:10018–10022 (1993).

Kim, S.G., Lin, L. J., Reid, B., "Determination of Nucleic Acid Backbone Conformation by $^1$H NMR," *Biochemistry* 31:3564–3574 (1992) (Exhibit 37).

Umemoto, K., Sarma, M.H., Gupta, G., Luo, J., Sarma, R., "Structure and Stability of a DNA Triple Helix in Solution: NMR Studies on $d(T)_6d(A)_6d(T)_6$ and Its and Its Complex with a Minor Groove Binding Drug, " *J. Am. Chem. Soc.* 112:4539–4545 (1990) (Exhibit 38).

Klevit, R., Wemmer, D., Reid, B., "$^1$H NMR Studies on the Interaction between Distamycin A and a Symmetrical DNA Dodecamer," *Biochemistry* 25:3296–3303 (1986) (Exhibit 39).

Leupin, W., Chazin, W., Hyberts, S., Denny, W., Wuthrich, K., "NMR Studies of the Complex between the Decadeoxynucleotide d–$(GCATTAATGC)_2$ and a Minor–Groove–Binding Drug," *Biochemistry* 25:5902–5910 (1986) (Exhibit 40).

Grokhovskii, S.L., Zhuze, A.L., Gottikh, B.P., "Ligands Possessing Affinity for Definite Sequences of DNA Base Pairs. VII. systhesis of analogs of Distamycin A Consisting of Two and Three N–Isoamylpyrrolecarboxamide fragments and an analog conting methyl–amide bonds in the molecule," *Plenum Publishging Co.* (1993) (Exhibit 41).

Bruice et al. (1992) Proc. Natl. Acad. Sci. USA 89:1700–1704 Mar. 1992.

FIG. I
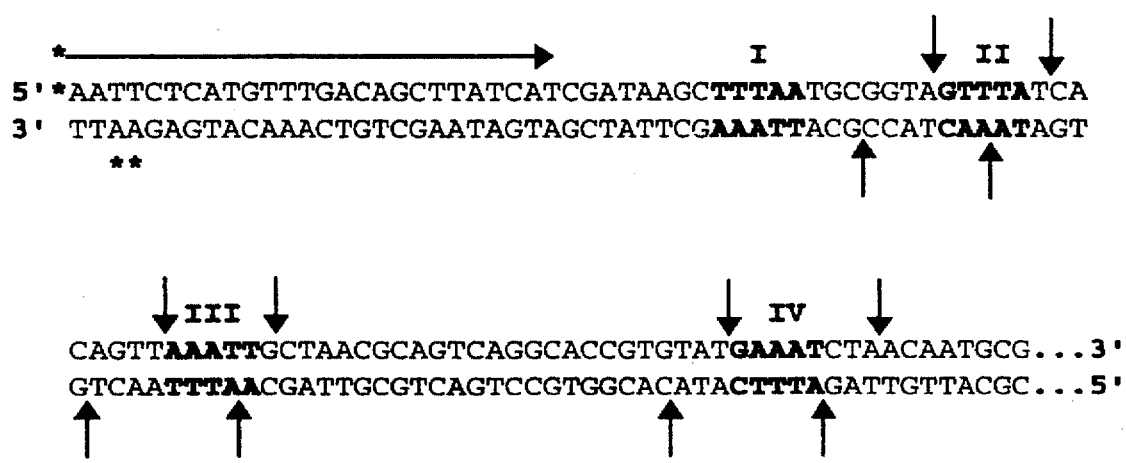

5'- $C_1$ $G_2$ $C_3$ $A_4$ $A_5$ $A_6$ $T_7$ $T_8$ $T_9$ $G_{10}$ $C_{11}$ $G_{12}$ -3'
3'- $G_{-1}$ $C_{-2}$ $G_{-3}$ $T_{-4}$ $T_{-5}$ $T_{-6}$ $A_{-7}$ $A_{-8}$ $A_{-9}$ $C_{-10}$ $G_{-11}$ $C_{-12}$ -5'

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:1:

GGCGCAAATT TGGCGG 16

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:2:

CCGCCAAATT TGCGCC 16

(2) INFORMATION FOR SEQ ID NO:3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:3:

CGCAAATTTG CG 12

(2) INFORMATION FOR SEQ ID NO:4:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:4:

AATTCTCATG TTTGACAGCT TATCATCGAT AAGCTTTAAT GCGGTAGTTT ATCACAGTTA 60

AATTGCTAAC GCAGTCAGGC ACCGTGTATG AAATCTAACA ATGCG 105

(2) INFORMATION FOR SEQ ID NO:5:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

TTAAGAGTAC AAACTGTCGA ATAGTAGCTA TTCGAAATTA CGCCATCAAA TAGTGTCAAT 60

TTAACGATTG CGTCAGTCCG TGGCACATAC TTTAGATTGT TACGC 105

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (genomic)

( x i ) SEQUENCE DESCRIPTION: SEQ ID NO:6:

```
GCGTTAAAC GC                                                    12
```

TRIHETEROCYCLIC PEPTIDES CAPABLE OF BINDING THE MINOR AND MAJOR GROOVES OF DNA

ACKNOWLEDGEMENT OF GOVERNMENT SUPPORT

This invention was made with Government support under Grant Contract No. N00014-90-J-4132 awarded by the Office of Naval Research. The Government has certain rights in this invention.

BACKGROUND

The advancement of molecular biology and genetic engineering has led to a greater understanding of the structure and function of nucleic acids on the molecular level. This greater understanding has brought about a need for reagents that can specifically bind to nucleic acids, particularly DNA, without requiring a complementary base sequence for hybridization. These reagents can be used to block enzymes that act on nucleic acids as well as to detect nucleic acids with high sensitivity.

Tripyrrole peptides are well known to bind weakly to some nucleic acids. Examples of such tripyrrole peptides include distamycin and netropsin and analogs thereof.

Distamycin is an oligopeptide originally isolated from a culture of *Streptomyces distallicus*. Distamycin binds the minor groove of AT-rich sequences of B-DNA, directly affects the conformation of bound and flanking nucleotides, and exhibits antibiotic activity. The structure of Distamycin is as follows.

FCE24517 is an analog of distamycin. Unlike distamycin, FCE24517 possesses anti-tumor activity. However, both distamycin and FCE24517 are unstable molecules. Further, both bind weakly to DNA. The structure of FCE24517 is as follows.

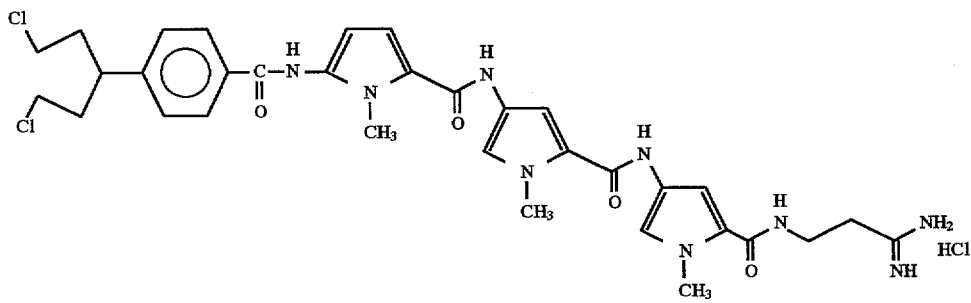

Netropsin is an oligopeptide that binds the minor groove of DNA without intercalating between DNA bases. Typically, netropsin exhibits preference for AT stretches and has demonstrated the ability to interfere with the actions of DNA topoisomerases I and II. The structure of netropsin is as follows.

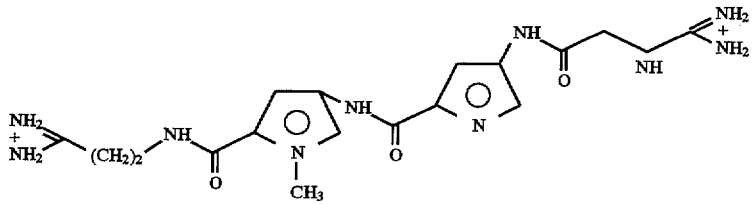

Microgonotropens are another class of tripyrrole peptides which bind to the minor groove of double stranded DNA (dsDNA) and extend its binding to the major groove. Microgonotropens are analogs of distamycin.

Microgonotropens are capable of binding the minor groove of DNA sequence selectively, reaching up and out of the minor groove with their polyamine moieties, and firmly grasping the phosphodiester backbone. In so doing, the microgonotropens increase their binding affinities to DNA and alter the conformation of DNA.

Microgonotropens, like the related lexitropsin minor groove binding agents distamycin and netropsin, have an affinity for A+T-rich regions.

The central polyamine groups of the microgonotropens were designed to reach the phosphate backbone of the DNA, to point towards the major groove and be able to ligate a metal ion, thereby providing putative hydrolytic catalysis of the dsDNA or enhanced base pair recognition.

Dien-microgonotropens are tripyrrole peptides which bind weakly to DNA (FIG. 15). They exhibit enhanced minor groove binding due to electrostatic interaction of the putative catalytic groups with the phosphodiester linkages. The structure of dien-microgonotropens are as follows.

tic agent with a high affinity for DNA would remain bound to DNA despite the presence of other competing agents having a lower affinity and/or an increased concentration.

SUMMARY OF THE INVENTION

The present invention provides a triheterocyclic peptide useful for binding DNA. The triheterocyclic peptide is one that contains three cyclic compounds. Such cyclic compounds may be a pyrrole, furan, thiophene, imidazole, oxazole, thiazole, and pyrazole.

The triheterocyclic peptide has first, second, and third heterocyclic rings. One, two or three of these heterocyclic rings have a polyamine group attached thereto. The polyamine group extends from a heteroatom of the heterocyclic ring towards the phosphate backbone and major groove of DNA.

Additionally, the polyamine groups of the triheterocyclic peptide attach to metal ions, phosphate substituents, and/or the floor of the major groove of DNA.

In one embodiment of the invention, the triheterocyclic peptide of the invention has the following formula:

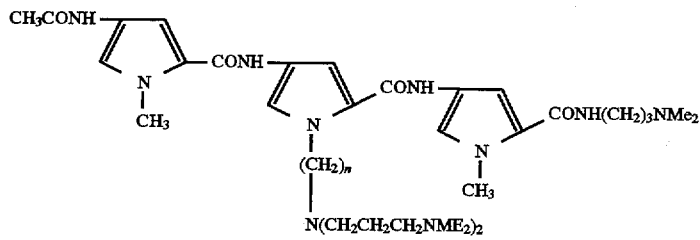

Although dien-microgonotropens specifically bind the minor groove of DNA, there was a need to develop other reagents with increased binding to DNA with increased stability which distamycin and FCE24517 do not provide.

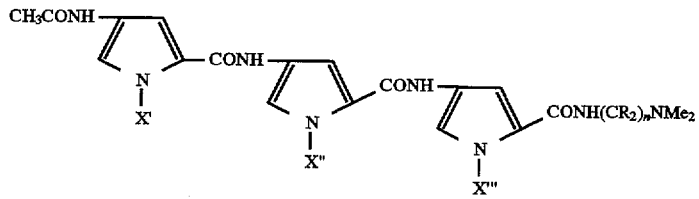

Stable reagents with higher binding affinities to DNA would provide a more advantageous diagnostic or therapeutic agent. For example, a diagnostic agent with a high affinity for DNA would provide less false positives when a more stringent washing condition is required. Further, a therapeu- X' is $CR_3$, $(CR_2)_n$—NRY, or $(CR_2)_n$—$CR_2Y$. X" is $CR_3$, $(CR_2)_n$—NRY, or $(CR_2)_n$—$CR_2Y$. Additionally, X'" is $CR_3$, $(CR_2)_n$—NRY, or $(CR_2)_n$—$CR_2Y$. The R group in the triheterocyclic peptide is a hydrogen (H) atom, a lower alkyl group, or halogen atom.

In another embodiment, the microgonotropen is a tren-microgonotropen having the following formula:

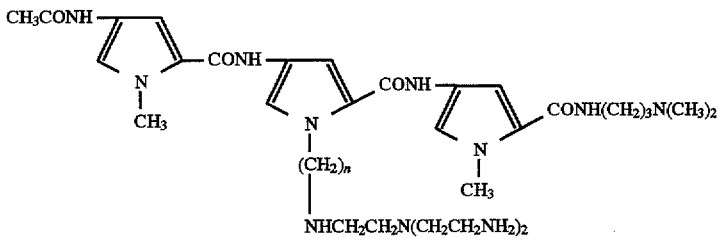

wherein $(CR_2)_n$ represents an alkyl linker of varied chain length, n is an integer of between 2-10. R represents H or a lower alkyl group.

Tren-microgonotropens are tripyrrole peptides having first, second, and third pyrrole rings. A pyrrole ring is a five atom aromatic ring having nitrogen at position 1 of the ring.

The peptide of the invention is capable of binding DNA. By so doing, the peptide is capable of prohibiting the binding of DNA with an enzyme, for example, topoisomerase I, which is important in DNA replication and/or genetic expression.

Generally, the peptide of the invention has a polyamine group attached to the nitrogen atom of one of the pyrroles of the tripyrrole peptide. In a preferred embodiment, the polyamine group is attached to the nitrogen (N) atom of the second pyrrole of the tripyrrole peptide.

Further, the peptide has the following characteristics. The peptide is capable of binding the minor groove of DNA with an equilibrium constant of $\geq 10^9 M^{-1}$. Additionally, the peptide is incapable of alkylating the enzyme or DNA.

In one embodiment of the present invention, the peptide is capable of binding the minor and major grooves of DNA so as to alter the conformation of DNA. This peptide has a polyamine group attached to the nitrogen atom of the second pyrrole of the tripyrrole peptide. The peptide has the following formula:

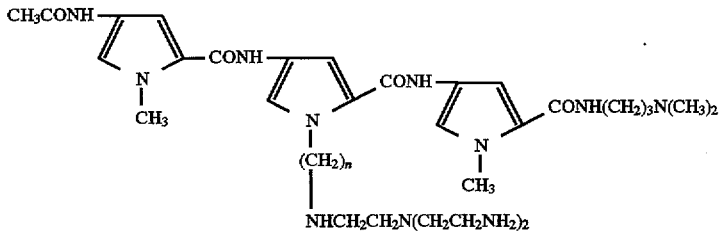

wherein n is 3, 4, or 5.

BRIEF DESCRIPTION OF THE FIGURES

FIG. 1. Partial nucleotide sequence of the 167 bp EcoRI/RsaI restriction fragment from plasmid pBR322 detailing four A+T-rich binding sites (bold type). The oligonucleotide primer for synthesis of dideoxynucleotide sequencing products is depicted by a horizontal arrow adjacent the annealing site. Positions of incorporated radiolabel in the oligonucleotide primer, 5'-labeled strand, and 3'-labeled strand are indicated with asterisks. Vertical arrows depict cleavages proximal to the protected sites. These were determined by the analysis of both 5' (downward arrows) and 3' (upward arrows) labeled restriction fragments at a binding agent concentration of 50 µM (SEQ ID NOS: 4-5).

(b) $R_L$ vs. agent concentration, {6a (____open circle____), 6b (_____open square____), and distamycin (____closed square____)} when examining the 1078 bp DNA fragment. The curves are interpolations between the data points for 6a, 6b, and distamycin. The data for FIGS. 5a and 5b were generated from FIG. 4 as explained in the text.

FIGS. 6a/b. A gel showing the effect of 6b, distamycin, and 5b (FIG. 15) on the ability of calf thymus topoisomerase I to relax 1 μg of supercoiled pBR322 at 37° C. The lanes are labeled with the name and the micromolar concentrations of the reagent used. In the first panel, the pBR322 was preincubated with or without 6b, distamycin, or 5b for 60 min before the 18 hr incubation with topoisomerase I (except for the φ control). In the second panel, pBR322 was incubated with topoisomerase I for 30 min before the addition of 6b, distamycin, or 5b and the subsequent 18 hr incubation.

Figure 7A:
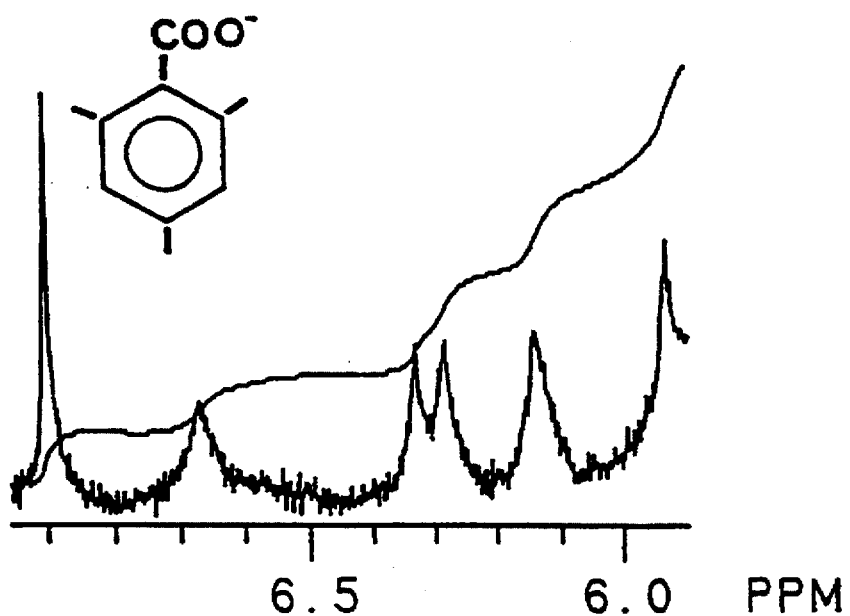
Figure 7B:
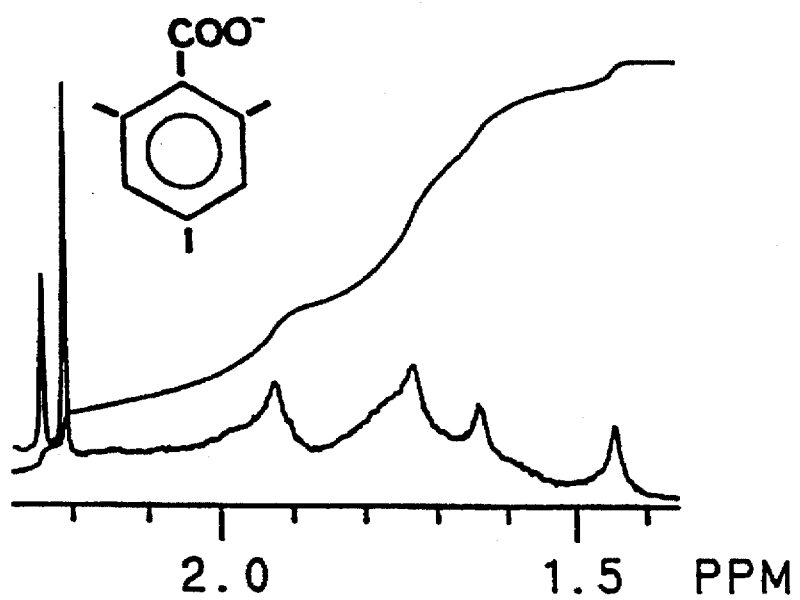
Figure 7C:
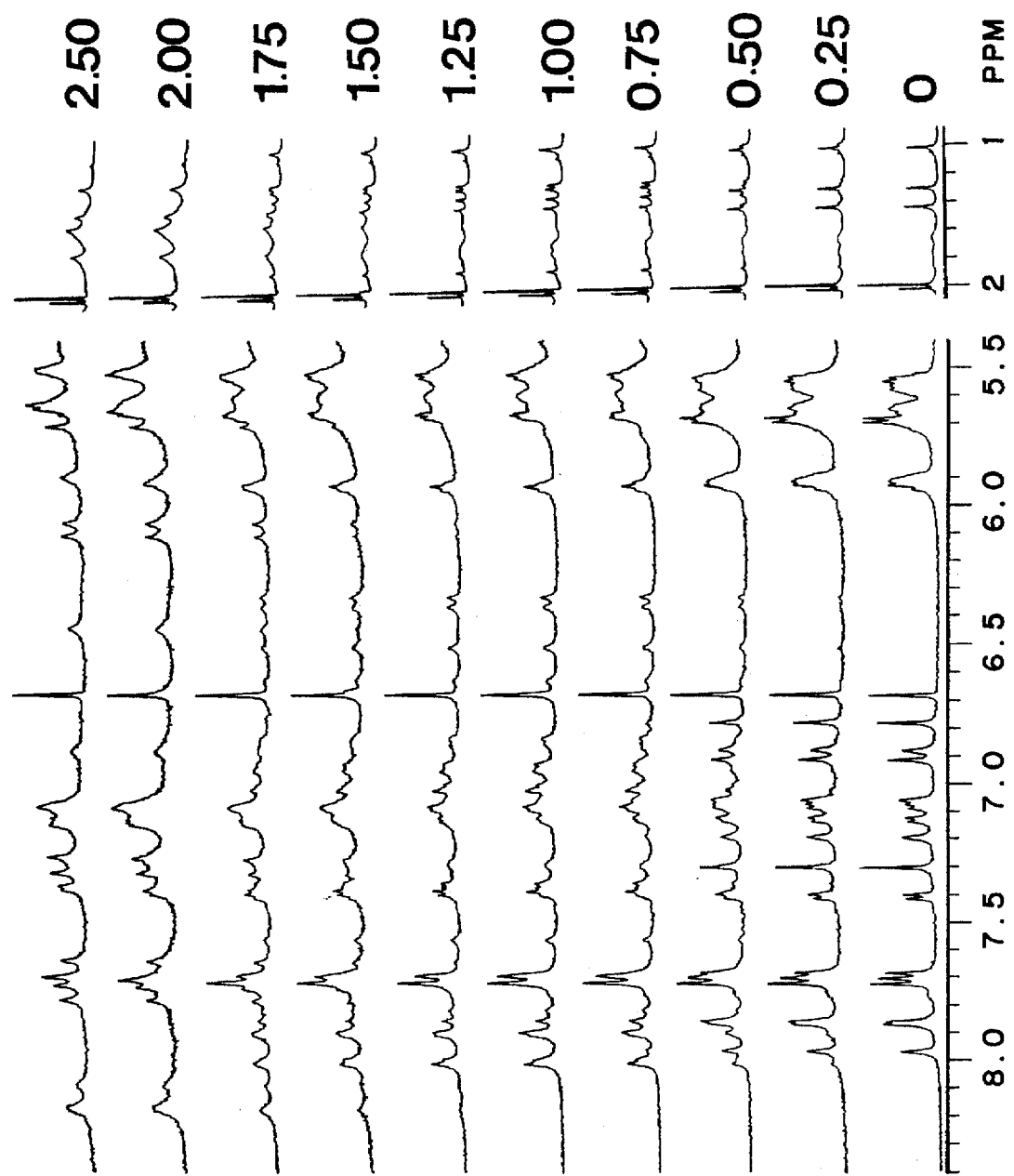

FIG. 7a–7c. $^1$H NMR titration of $3.8\times10^{-4}$M d(CGCA$_3$T$_3$GCG (SEQ ID NO:3))$_2$ in D$_2$O (10 mM phosphate buffer, pH 7.0, 10 mM NaCl, $3.8\times10^{-4}$M mesitoate) with tren-microgonotropen-b (6b) at the indicated mole ratios of 6b/dsDNA. Insets A and B (6b/dsDNA=2:1) show that the 3,5 aromatic protons of mesitoate (internal standard) integrate 1:1 with each of the pyrrole protons of 6b (inset A) and the 2,6 CH$_3$'s of mesitoate integrate 1:1 with each of the T$_7$, T$_8$, and T$_9$ equivalent CH$_3$ protons of the + and − strands (inset B).

Figure 8:
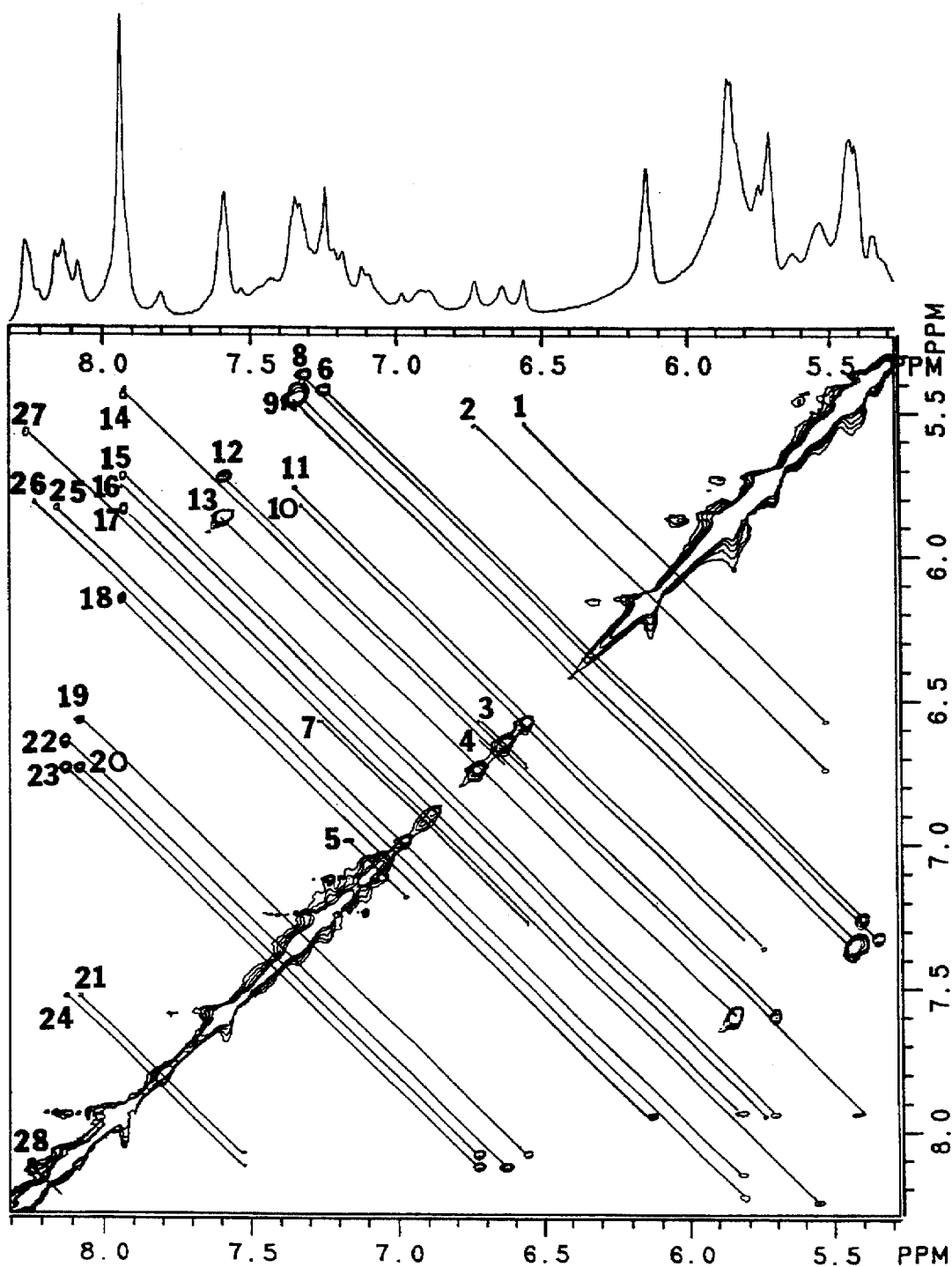

FIG. 8. Expansion of the nuclear Overhauser effect spectropscopy (NOESY) spectrum in the (5.3–8.3)×(5.3–8.3) ppm region of the 1:1 complex of d(CGCA$_3$T$_3$GCG (SEQ ID NO:3)), $2.5\times10^{-3}$M with 6b in 99.96% D$_2$O containing 10 mM NaCl and 10 mM phosphate buffer, pH 7.0 at 10° C. ($\tau_m$=180 ms). 1. H6-A$_{-8}$H1'; 2. H4-A$_{-8}$H1'; 3. H4-H6; 4. H4-H2; 5. A$_4$H2-A$_5$H2; 6. H3-CH$_2$"(1); 7. H6-H5; 8. C$_{-2}$H6-C$_{-2}$H5; 9. C$_{11}$H6-C$_{11}$H5, C$_3$H6-C$_3$H5; 10. C$_{11}$H6-G$_{10}$H1'; 11. C$_3$H6-C$_3$H1'; 12. C$_1$H6-C$_1$H1'; 13. C$_1$H6-C$_1$H5; 14. G$_{12}$H8-C$_{11}$H5; 15. G$_2$H8-C$_1$H1'; 16. G$_{-3}$H8-T$_{-4}$H1'; 17. G$_2$H8-G$_2$H1'; 18. G$_{12}$H8-G$_{12}$H1'; 19. A$_{-8}$H2-H6; 20. A$_{-8}$H2-H4; 21. A$_{-9}$H2-A$_{-8}$H2; 22. A$_{-7}$H2-H2; 23. A$_{-7}$H2-H4; 24. A$_{-9}$H2-A$_{-7}$H2; 25. A$_{-9}$H8-A$_{-9}$H1', A$_6$H8-A$_6$H1'; 26. A$_4$H8-A$_4$H1'; 27. A$_5$H8-A$_5$H1'; 28. A$_{-8}$H8-A$_{-9}$H8, A$_5$H8-A$_6$H8.

Figure 9:
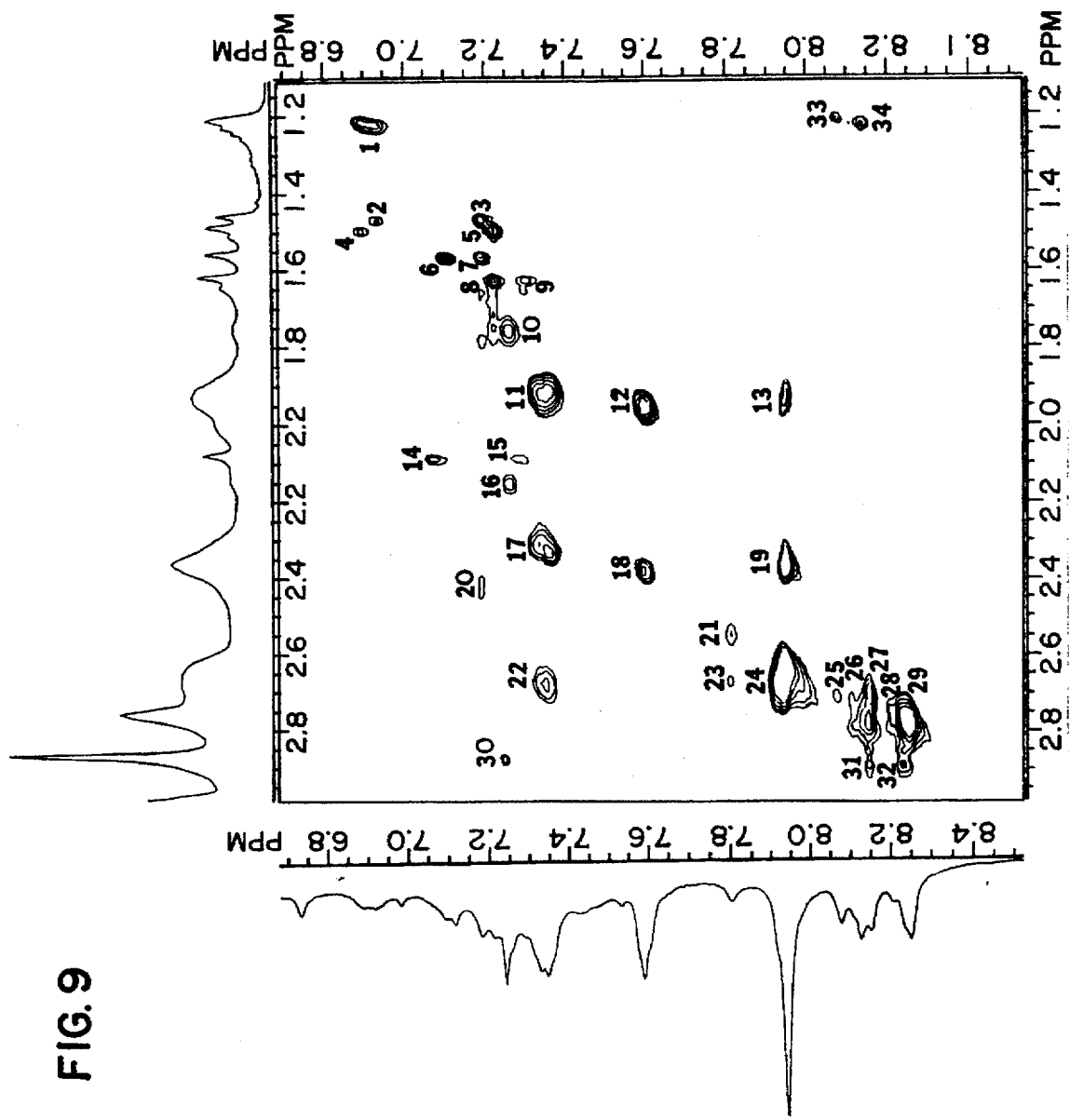

FIG. 9. Expansion of the NOESY spectrum in the (6.7–8.5)×(1.1–3.0) ppm region of the 1:1 complex of d(CGCA$_3$T$_3$GCG (SEQ ID NO:3))$_2$, $2.5\times10^{-3}$M with 6b in 99.96% D$_2$O containing 10 mM NaCl and 10 mM phosphate buffer, pH 7.0 at 10° C. ($\tau_m$=180 ms). 1. T$_7$H6-T$_7$CH$_3$, T$_{-6}$H6-T$_{-6}$CH$_3$; 2. T$_7$H6-T$_8$CH$_3$; 3. T$_8$H6-T$_8$CH$_3$; 4. T$_{-6}$H6-T$_{-5}$CH$_3$; 5. T$_{-5}$H6-T$_{-5}$CH$_3$; 6. T$_9$H6-T$_9$CH$_3$; 7. T$_8$H6-T$_9$CH$_3$; 8. T$_{-5}$H6-T$_{-4}$CH$_3$; 9. T$_{-4}$H6-T$_{-4}$CH$_3$; 10. H5-CH$_2$"(2); 11. C$_3$C$_{11}$H6-C$_3$C$_{11}$H2'; 12. C$_1$H6-C$_1$H2'; 13. G$_2$G$_{12}$H8-C$_1$C$_{11}$H2'; 14. H$_1$—CH$_3^{R1}$; 15. T$_{-4}$H6-CH$_3^{R1}$; 16. H3-CH$_2$"(3); 17. C$_3$C$_{11}$H6-C$_3$C$_{11}$H$_2$"; 18. C$_1$H6-C$_1$H2"; 19. G$_2$G$_{12}$H8-C$_1$C$_{11}$H2"; 20. T$_8$H6-T$_7$H2"; 21. G$_{10}$H8-G$_{10}$H2'; 22. C$_3$C$_{11}$H6-G$_2$G$_{10}$H2"; 23. G$_{10}$H8-G$_{10}$H2"; 24. G$_2$G$_{12}$G$_{-3}$H6-G$_2$G$_{12}$G$_{-3}$H2"; 25. A$_{-7}$H8-A$_{-7}$H2'; 26. A$_6$H8-A6H2'2"; 27. A$_{-9}$H8-A$_{-9}$H2'; 28. A$_4$H8-A$_4$H2'2"; 29. A$_5$H8-A$_5$H2'2"; 30. H5-A$_{-8}$H2"; 31. A$_{-9}$H8-A$_{-9}$H2'2"; 32. A$_{-8}$H8-A$_{-8}$H2'2"; 33. A$_{-7}$H8-T$_{-6}$CH$_3$; 34. A$_6$H8-T$_7$CH$_3$.

Figure 10:
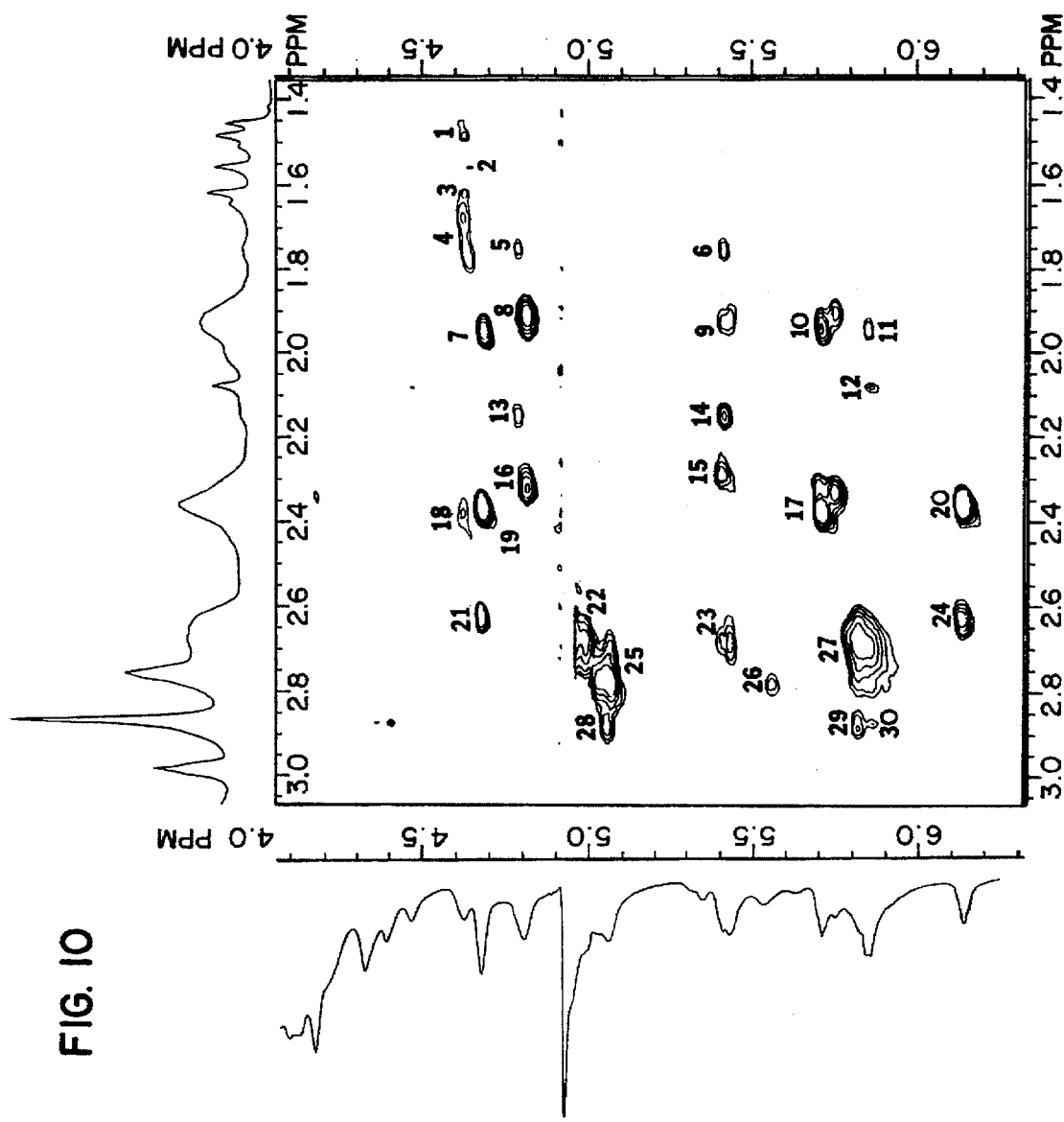

FIG. 10. Expansion of the NOESY spectrum in the (1.4–3.1)×(4.0–6.3) ppm region of the 1:1 complex of d(CGCA$_3$T$_3$GCG (SEQ ID NO:3))$_2$, $2.5\times10^{-3}$M with 6b in 99.96% D$_2$O containing 10 mM NaCl and 10 mM phosphate buffer, pH 7.0 at 10° C. ($\tau_m$=180 ms ). 1. T$_{-5}$T$_8$CH$_3$—T$_5$T$_8$H3'; 2. T$_9$CH$_3$—T$_9$H3'; 3. T$_{-4}$CH$_3$—T$_{-4}$H3'; 4. CH$_2$" (2)-T$_8$H3'; 5. CH$_2$"(2)-T$_9$H3'; 6. CH$_2$"(1)-CH$_2$"(2); 7. C$_1$H2'-C$_1$H3'; 8. C$_1$C$_{11}$H2'-C$_1$C$_{11}$H3'; 9. C$_3$C$_{11}$H2'-C$_3$C$_{11}$H5; 10. C$_1$C$_3$C$_{11}$H2'-C$_1$C$_3$C$_{11}$H1'; 11. C$_1$H2'-C$_1$H5; 12. CH$_3^{R1}$-A$_6$H1'; 13. CH$_2$"(3)-T$_9$H3'; 14. CH$_2$"(3)-CH$_2$" (1); 15. C$_3$C$_{11}$H2"-C$_3$C$_{11}$H5; 16. C$_3$C$_{11}$H2"-C$_3$C$_{11}$H3'; 17. C$_3$C$_{11}$H2"-C$_3$C$_{11}$H1'; 18. T$_7$T$_{-5}$H2"-T$_7$T$_{-5}$H3'; 19. G$_{12}$H2'-G$_{12}$H3'; 20. G$_{12}$H2'-G$_{12}$H1'; 21. G$_{12}$H2"-G$_{12}$H3'; 22. G$_2$G$_{10}$H2"-G$_2$G$_{10}$H3'; 23. C$_3$C$_{10}$H5-G$_2$G$_{10}$H2"; 24. G$_{12}$H2"-G$_{12}$H1'; 25. A$_4$A$_5$A$_6$H3'-A$_4$A$_5$A$_6$H2'2"; 26. A$_5$A$_{-8}$H1'-A$_5$A$_{-8}$H2"; 27. A$_4$A$_6$G$_{10}$G$_2$H1'-A$_4$A$_6$G$_{10}$G$_2$H2'2"; 28. A$_{-9}$A$_{-8}$H1'-A$_{-9}$A$_{-8}$H2"; 29. A$_{-9}$H2"-A$_{-9}$H1'; 30. CH$_3^{R3}$-G$_{10}$H1'.

Figure 11:
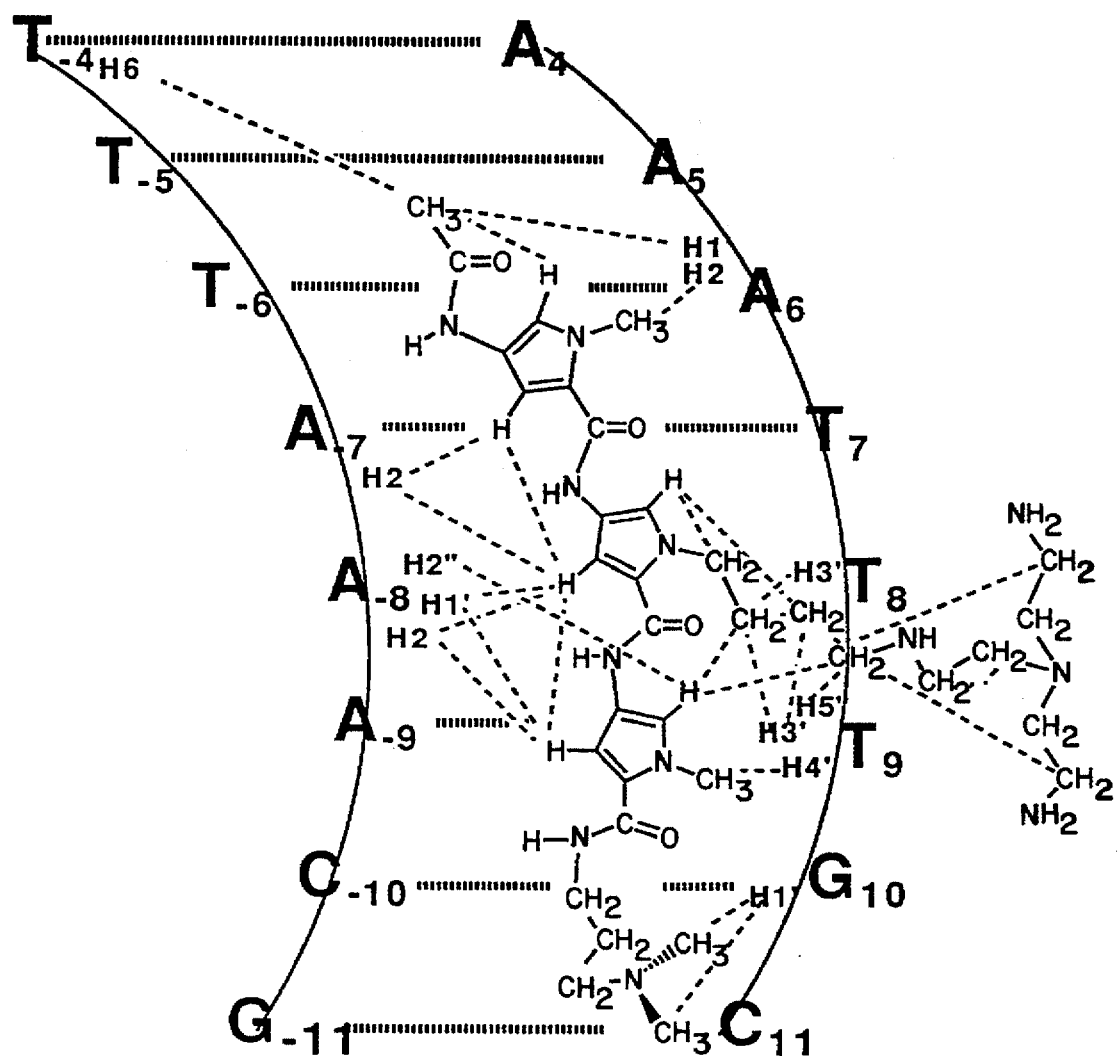

FIG. 11. Schematic representation of the dsDNA-6b intracomplex and 6b intramolecular NOE interactions (represented by broken lines) in the 1:1 complex of d(CGCA$_3$T$_3$GCG (SEQ ID NO:3))$_2$ at 2.5 mM with 6b in 99.96% D$_2$O containing 10 mM NaCl and 10 mM phosphate buffer, pH 7.0 at 10° C.

Figure 12:
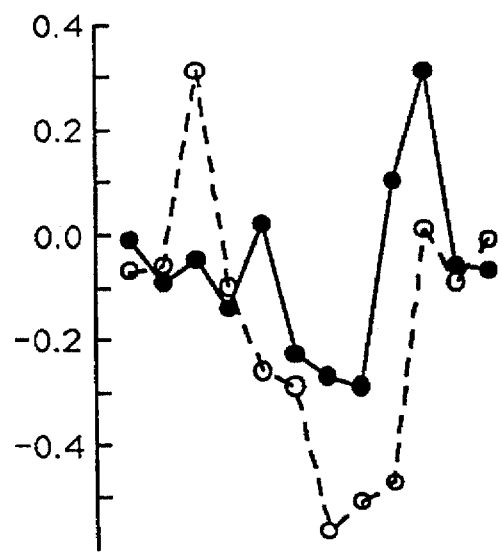
Figure 12:
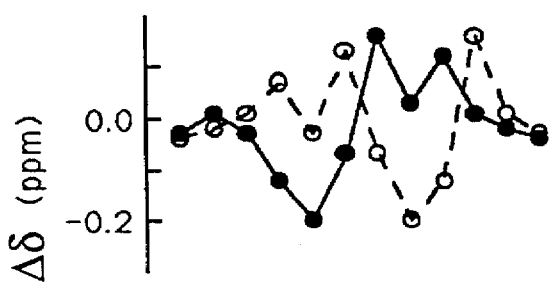
Figure 12:
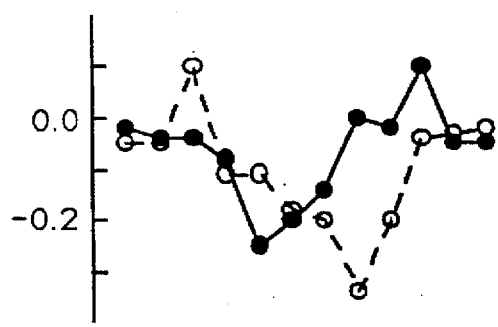
Figure 12:
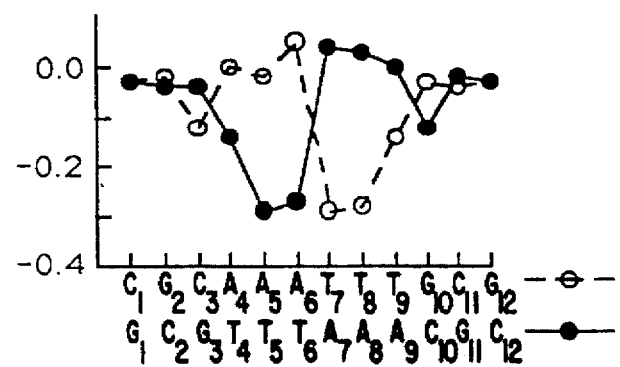
Figure 12:
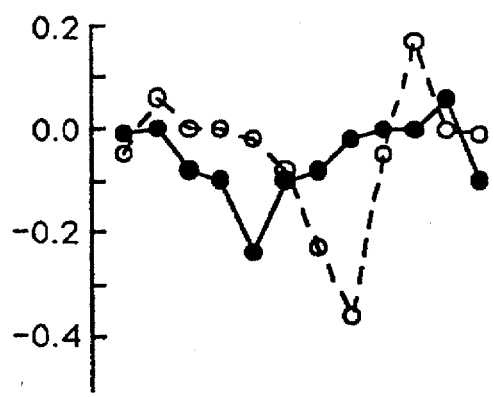
Figure 12:
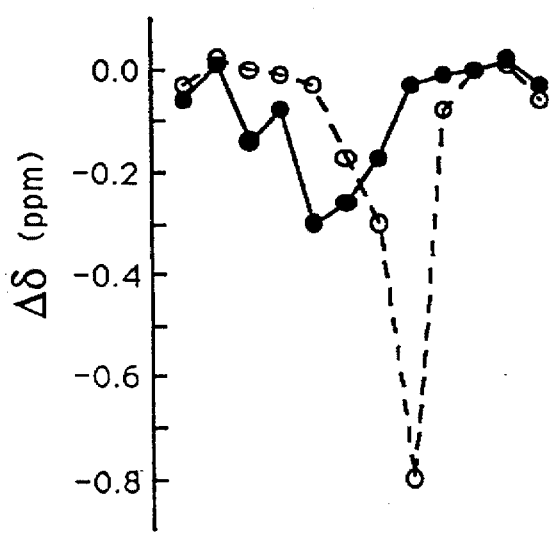
Figure 12:
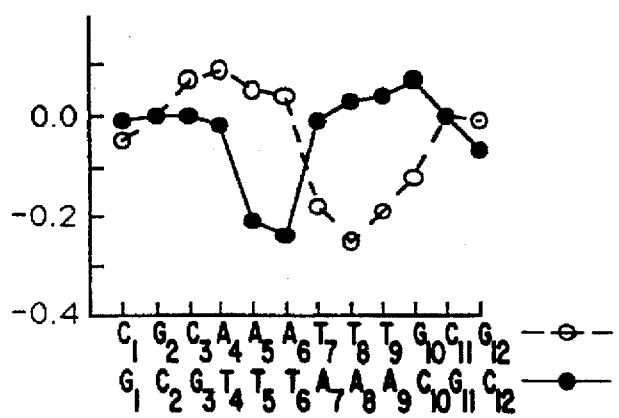

FIG. 12. Induced chemical shift differences between the 1:1 complex of d(CGCA$_3$T$_3$GCG (SEQ ID NO:3))$_2$ with 6b and the free dsDNA vs. the dsDNA sequence for the selected dsDNA protons: (a) H1'; (b) H2'; (c) H2"; (d) H3'; (e) H5'; (f) H5"; (g) H6/8. Δδ=δ$_{complex}$−δ$_{free\ dsDNA}$.

Figure 13B:
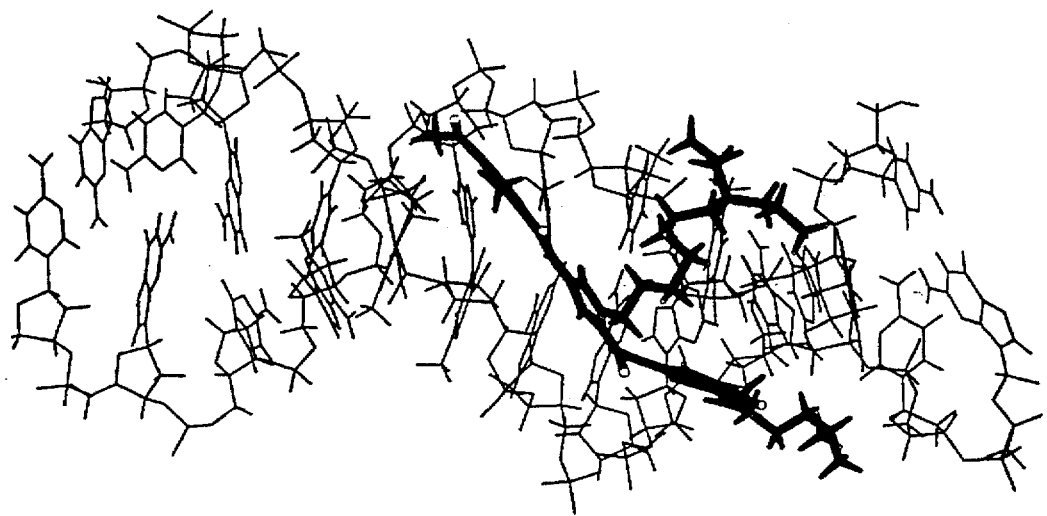
Figure 13A:
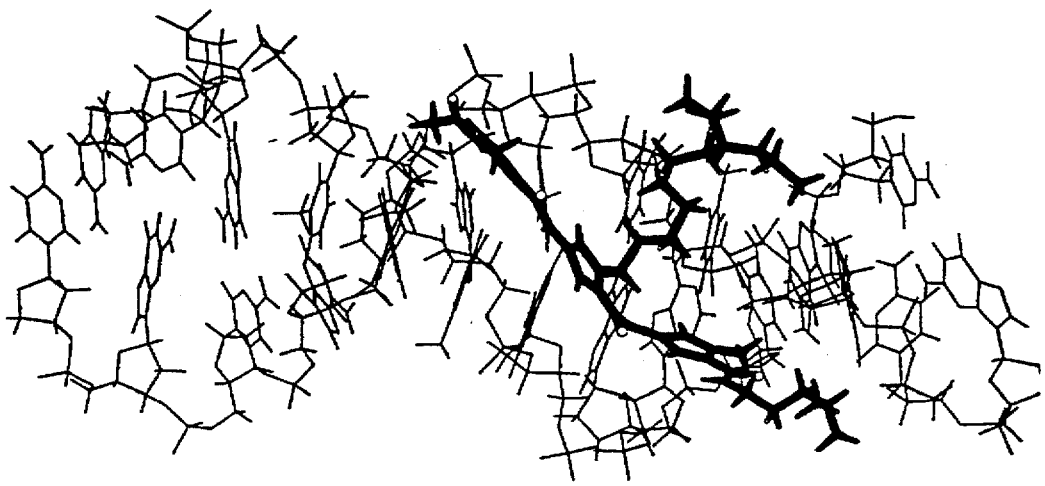
Figure 13D:
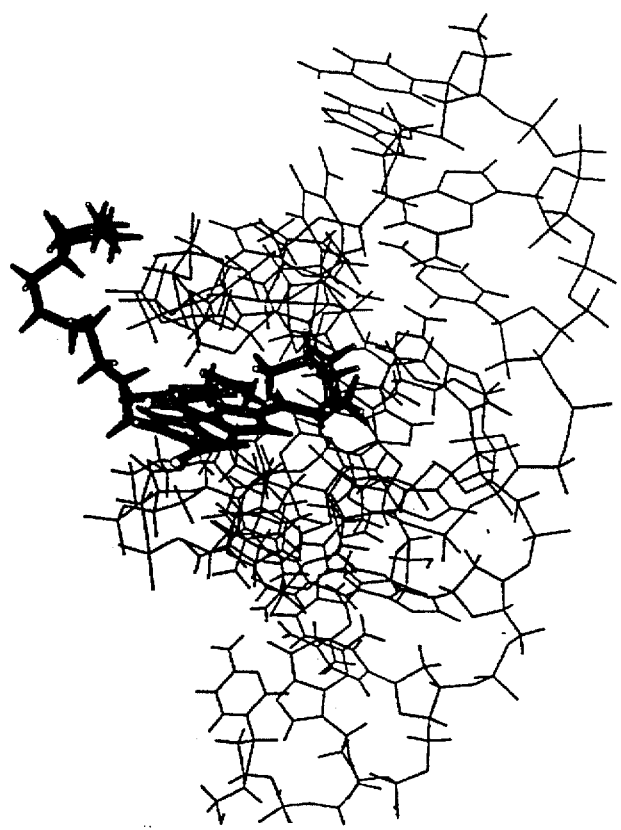
Figure 13C:
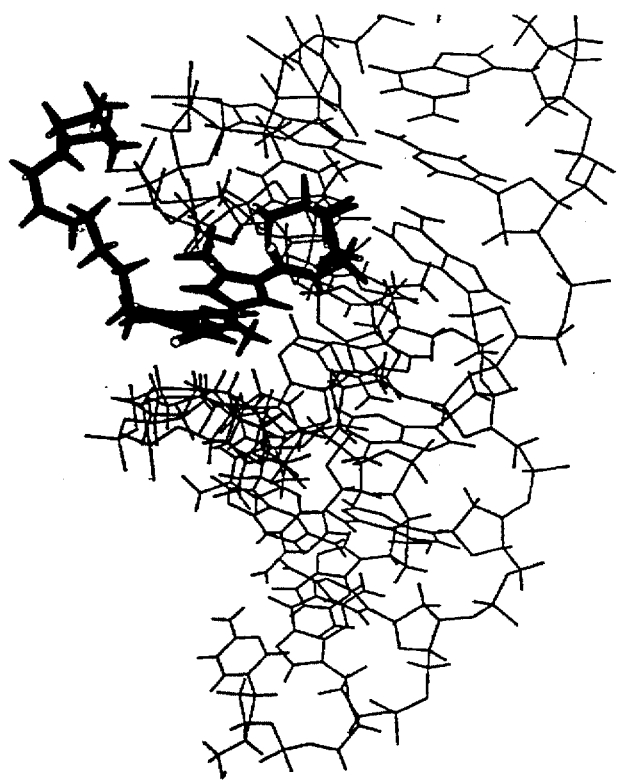
Figure 13F:
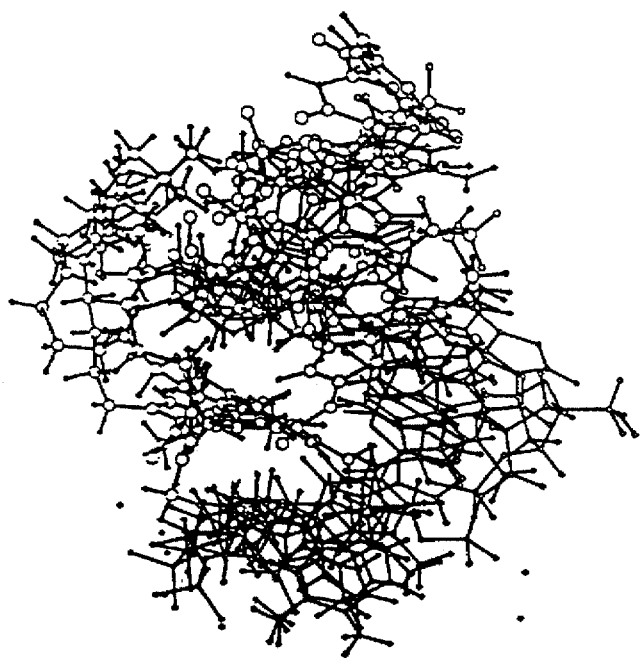
Figure 13E:
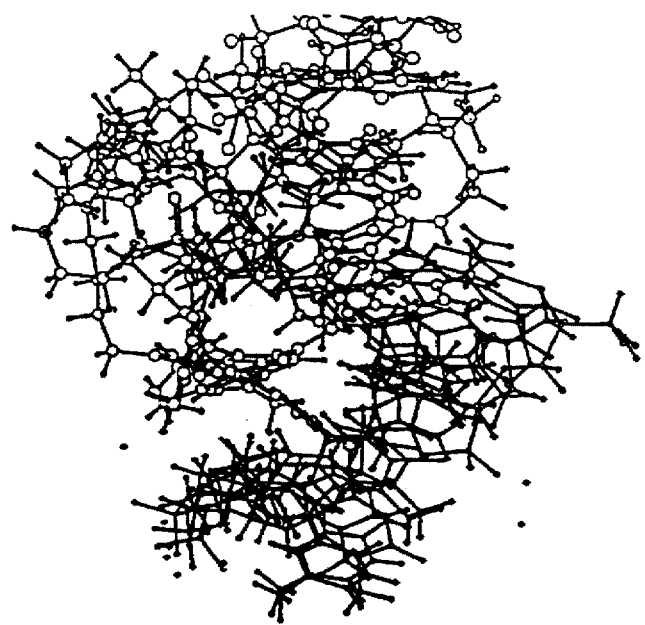
Figure 14A:
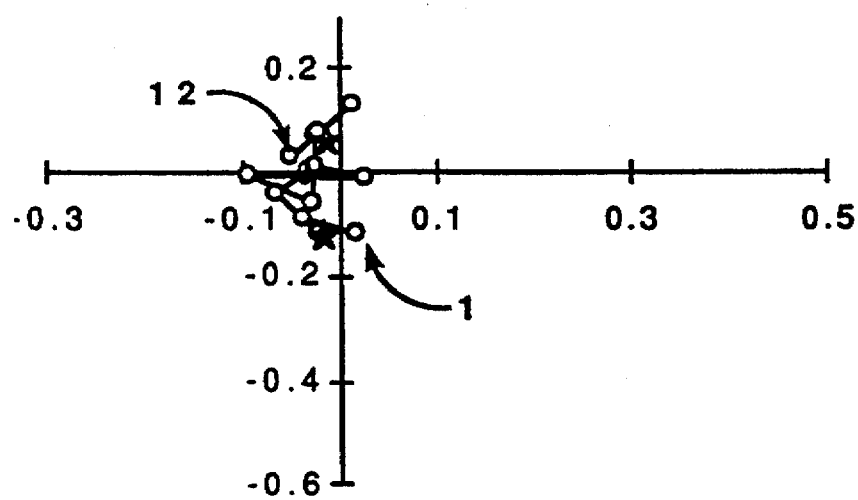
Figure 14B:
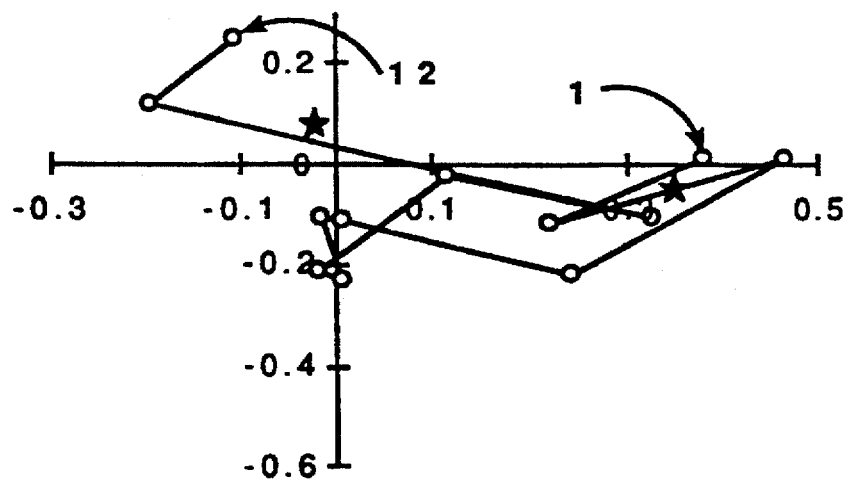
Figure 14C:
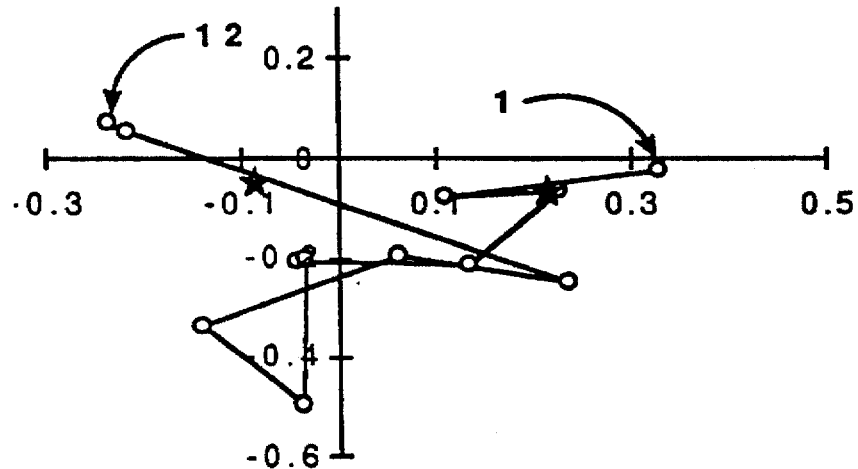
Figure 14D:
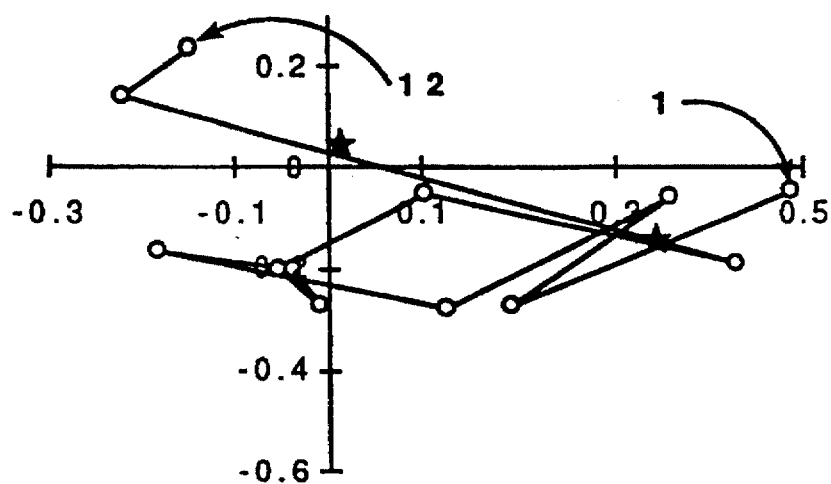
Figure 14E:
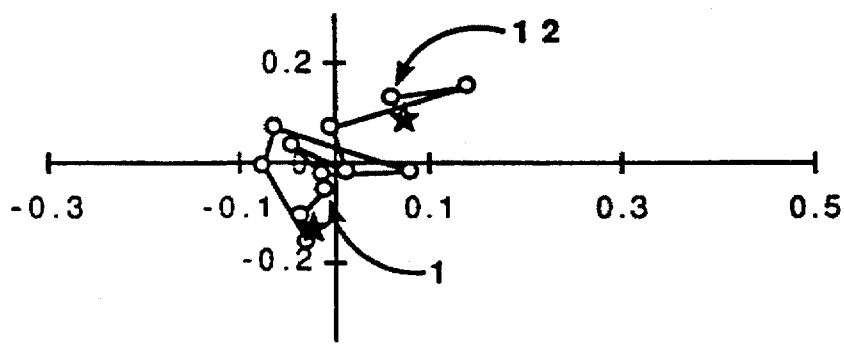
Figure 14F:
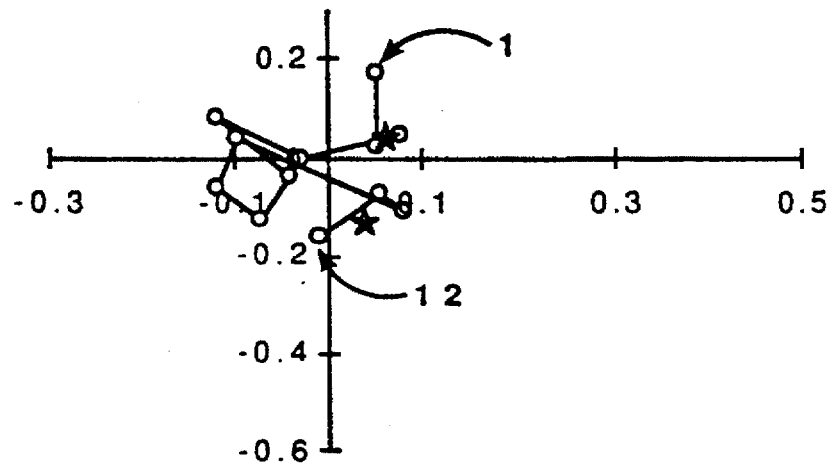

FIGS. 13a–13c. Stereo models of the D$_2$O solution structure of: (a,b) the 1:1 complex of d(CGCA$_3$T$_3$GCG (SEQ ID NO:3))$_2$ with 6b and (c) an overlay of two structures of the 1:1 complex of d(CGCA$_3$T$_3$GCG (SEQ ID NO:3))$_2$with 5c (Blasko, A.; Browne, K. A.; He, G.-X.; Bruice, T. C. J. Am. Chem. Soc. 1993, 115, 7080) and 6b.

FIG. 14. Normal vector plots to the mean plane of the base pairs for the d(CGCA$_3$T$_3$GCG (SEQ ID NO:3))$_2$: 6b complex and for previously described dodecamer structures showing the bending of the helical axes. The best DNA helix axis is perpendicular to the plane of the paper at the intersection of the x- and y-axes. The x- and y-axes are components of the changes in direction cosines of the normal vectors of the best helix axis to the best mean plane through each base pair projected onto the plane of the paper. The first and last base pairs are labeled in bold (1 and 12, respectively) with lines consecutively connecting the intervening base pairs. Bold star symbols (*) indicate the positions used to calculate the bending angles (α). (a) Crystal structure of d(CGCA$_3$T$_3$GCG (SEQ ID NO:3))$_2$ (α=10.8°) (Blaskó, A., et al., 1993, supra). (b) NOE refined solution structure of d(CGCA$_3$T$_3$GCG (SEQ ID NO:3))$_2$ (α=21.4°) (Blaskó, A., et al., 1993, supra). (c) NOE refined solution structure of d(CGCA$_3$T$_3$GCG (SEQ ID NO:3))$_2$: 5c (α=17.2°) (Blaskó, A., et al., 1993, supra). (d) NOE refined solution structure of d(CGCA$_3$T$_3$GCG (SEQ ID NO:3))$_2$: 6b (α=22.2°). (e) Crystal structure of d(CGCA$_3$T$_3$GCG (SEQ ID NO:3))$_2$: Dm (α=13.9°)(Coll, M.; Frederick, C. A.; Wang, A. H.-J.; Rich, A. Proc. Natl. Acad. Sci. (USA) 1987, 84, 8385). (f) NOE refined solution structure of d(CGCA$_3$T$_3$GCG (SEQ ID NO:3))$_2$: Dm$_2$ (α=11.3°) (Pelton, J. G.; Wemmer, D. E. J. Am. Chem. Soc. 1990, 112, 1393).

Figure 15:
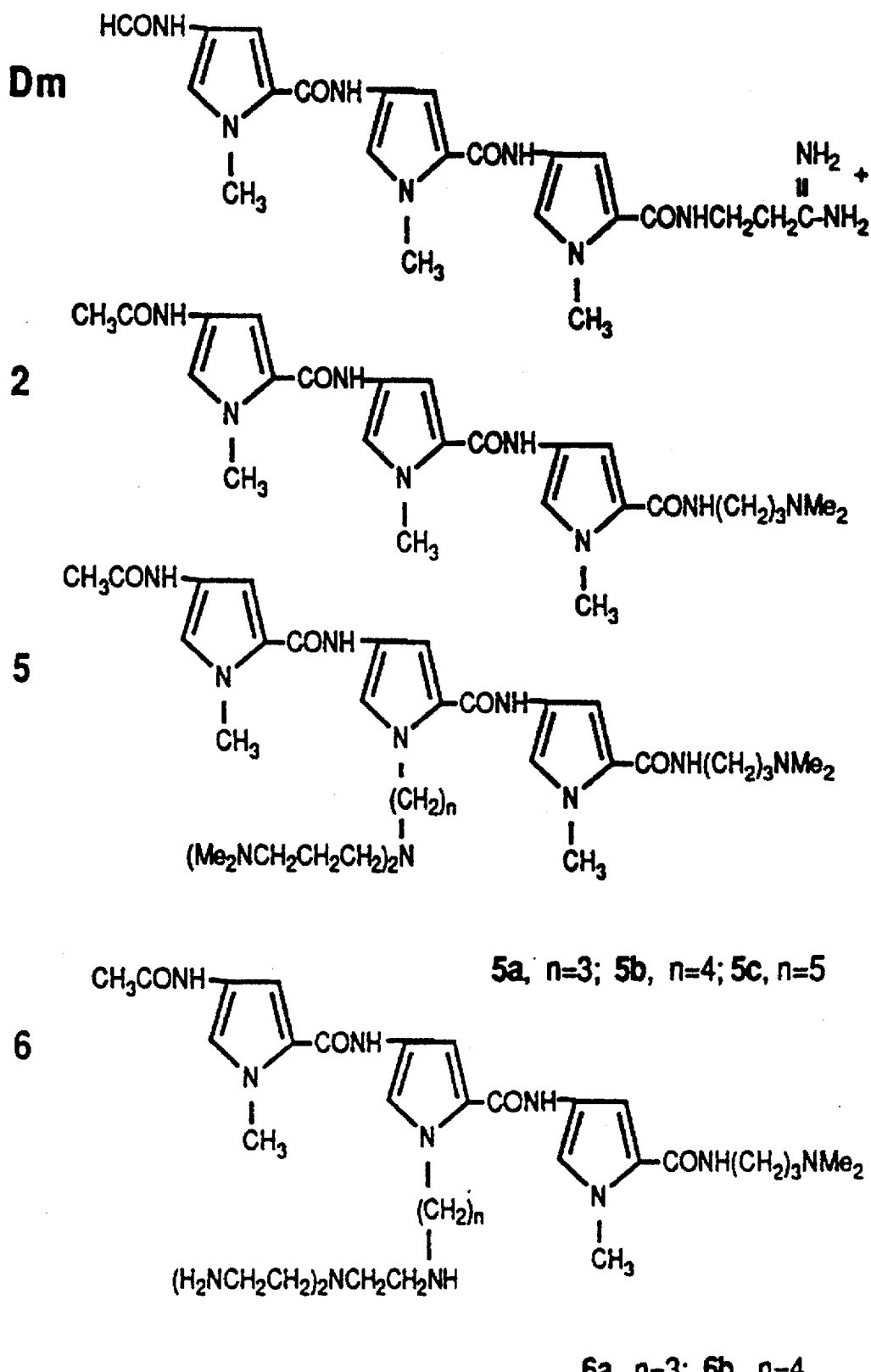

FIG. 15. A diagram showing the structure of Distamycin (designated Dm), microgonotropens (designated 2), dien-microgonotropens (designated 5), and tren-microgonotropens (designated 6).

Figure 16A:
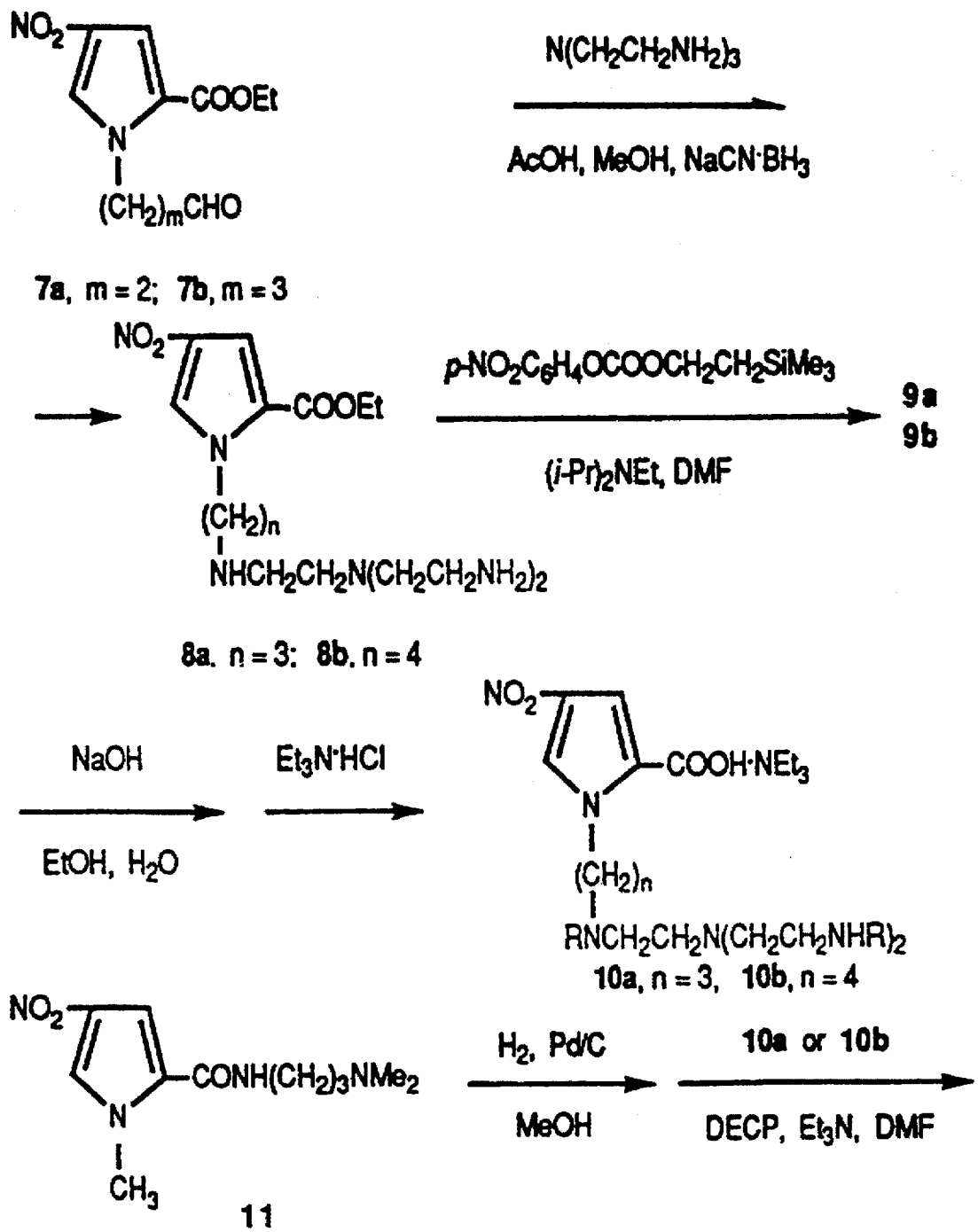
Figure 16B:
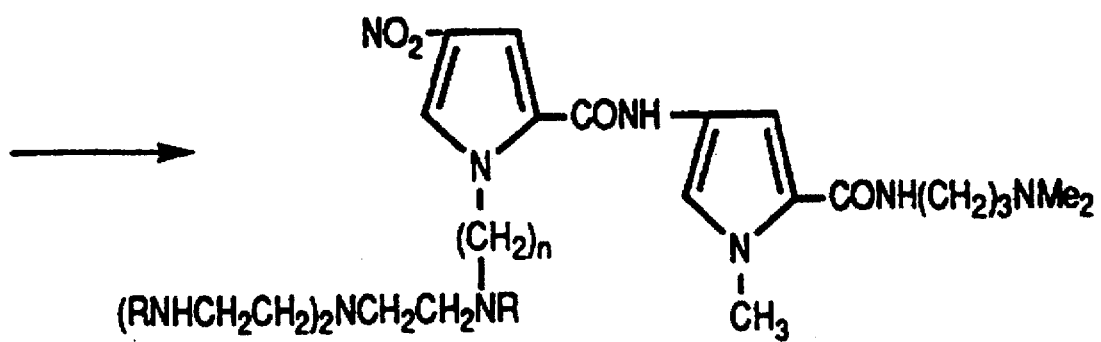
Figure 16C:
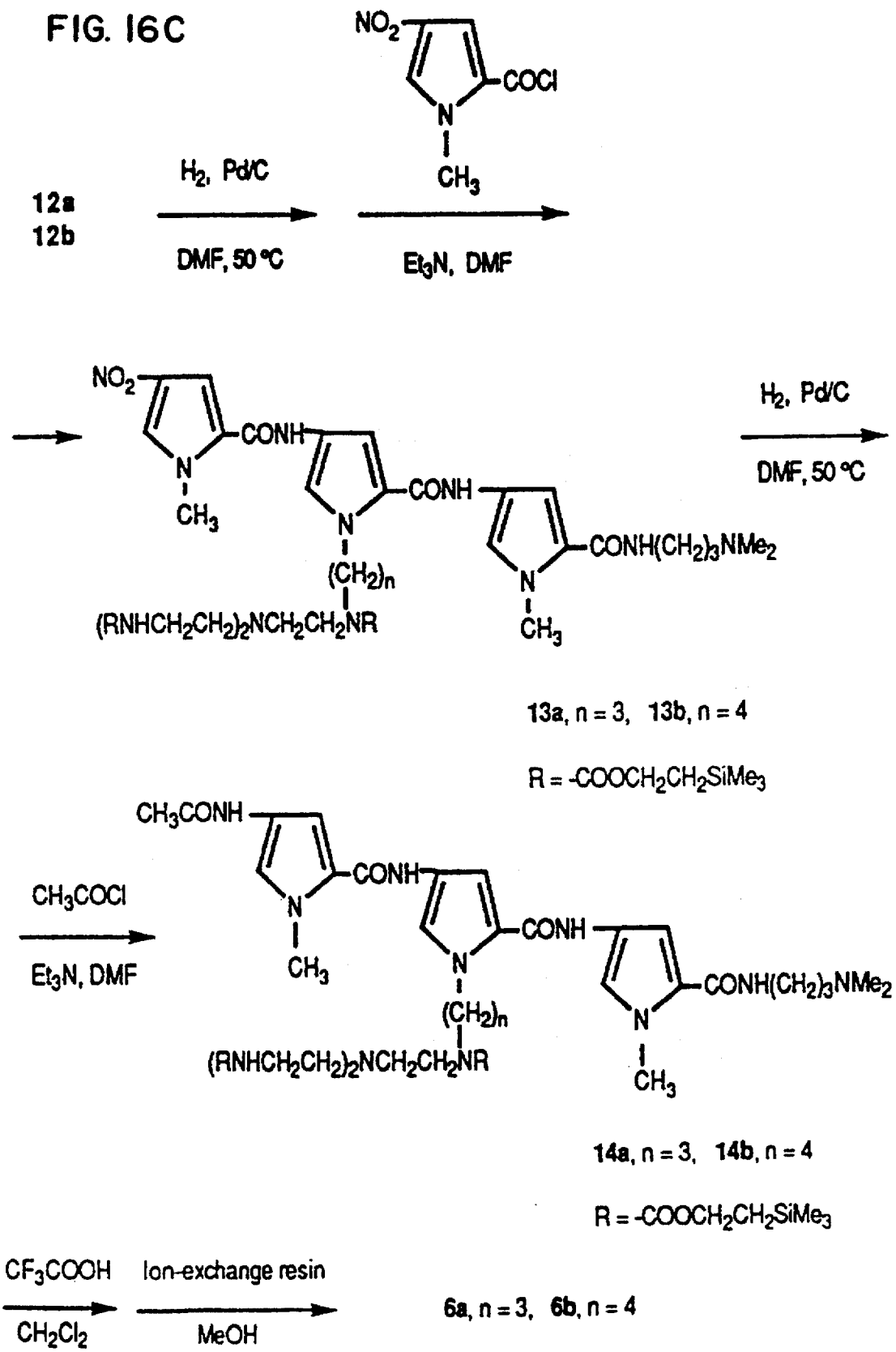

FIG. 16. A schematic diagram of the synthesis of 6a,b which began with the preparation of the central pyrrole units (8a,b) in which the tren group was attached to the pyrrole through the desired linker arms.

Figure 17:
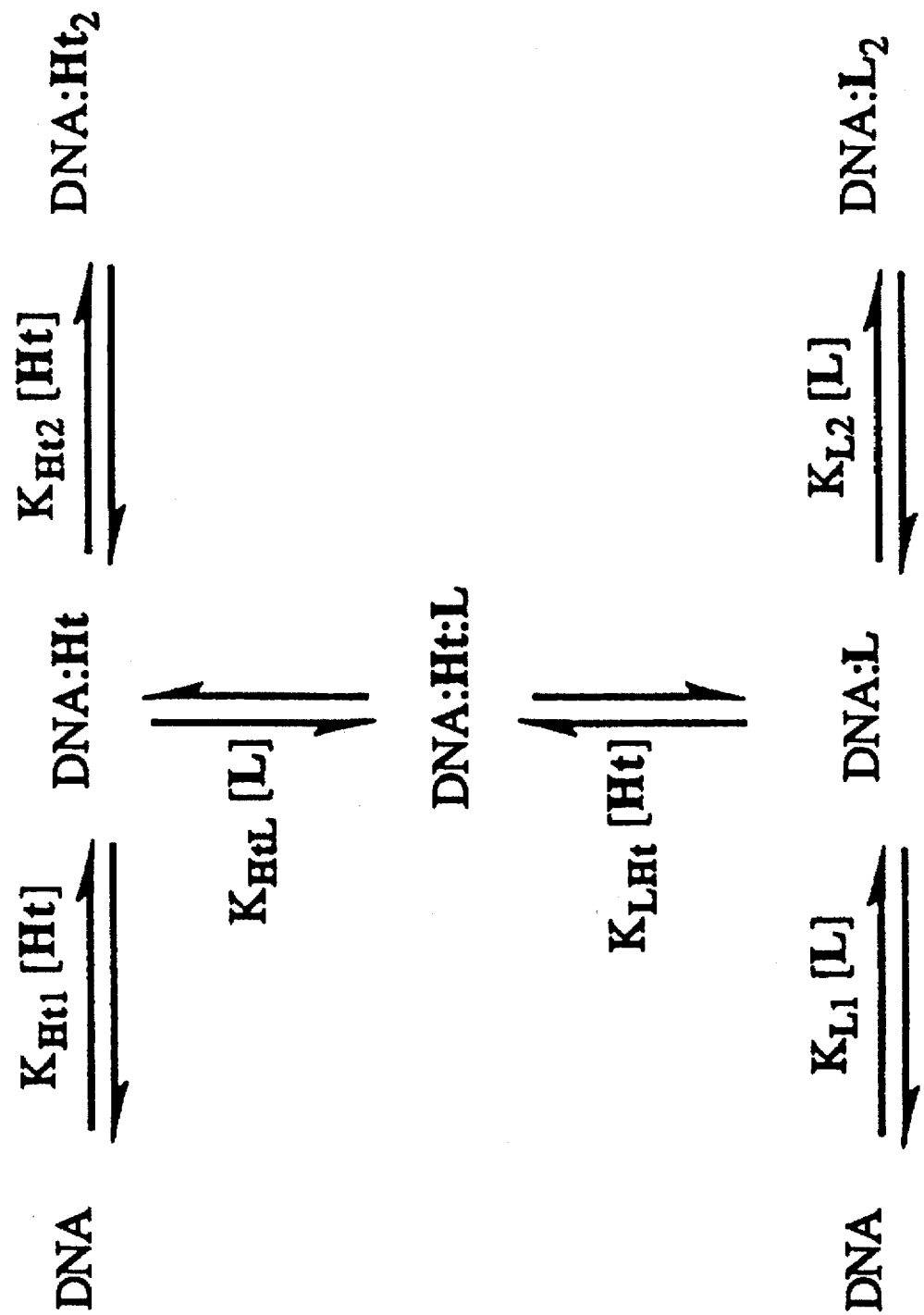

FIG. 17. A schematic diagram showing that equilibrium constants for the complexing of one and two Ht species to the hexadecamer with one and two L (where L equals 6a or 6b) binding to the hexadecamer, plus equilibrium constants for the simultaneous binding of one Ht and one L at the same site.

Figure 18:
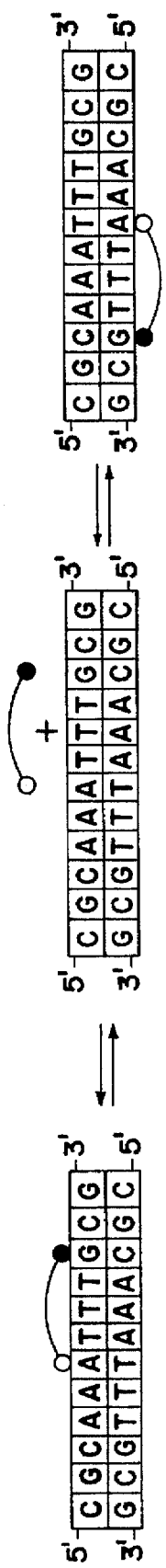

FIG. 18. A diagram showing that exchanges between two equivalent binding site is governed by a "flip-flop" mechanism (SEQ ID NOS: 3 and 6).

Figure 19:
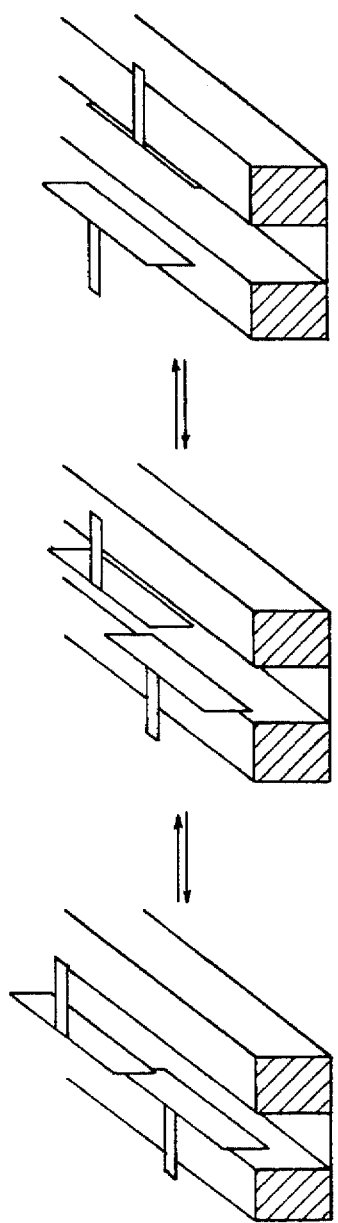

FIG. 19. A line drawing showing that the broadening of the A.T resonances of the 2:1 complex of 6b/d (CGCA₃T₃GCG (SEQ ID NO:3))₂ could be due to an asymmetric 2:1 rigid binding mode in which 6b exchanges between two equivalent sites of the dsDNA or a symmetrical 2:1 binding mode in which two molecules of 6b exchange.

Figures 20A, 20B:
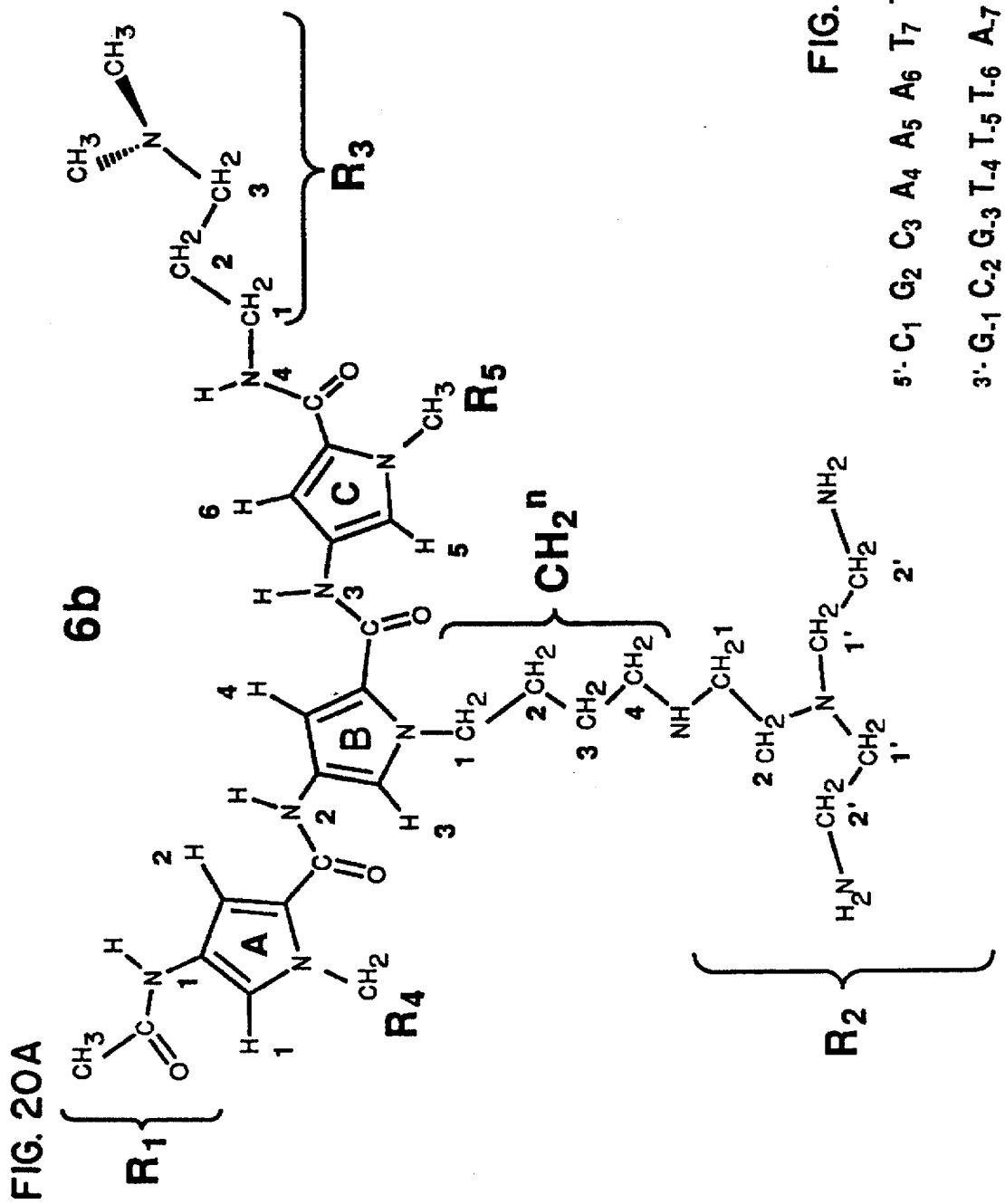

FIGS. 20a/b (a) A diagram showing the structure of a tren-microgonotropen (6b from FIG. 15) and the location of proton-labelling for NMR procedure. (b) The labeling sequence of the oligonucleotide sequence and its complementary strand (SEQ ID NO:3).

Figure 21:
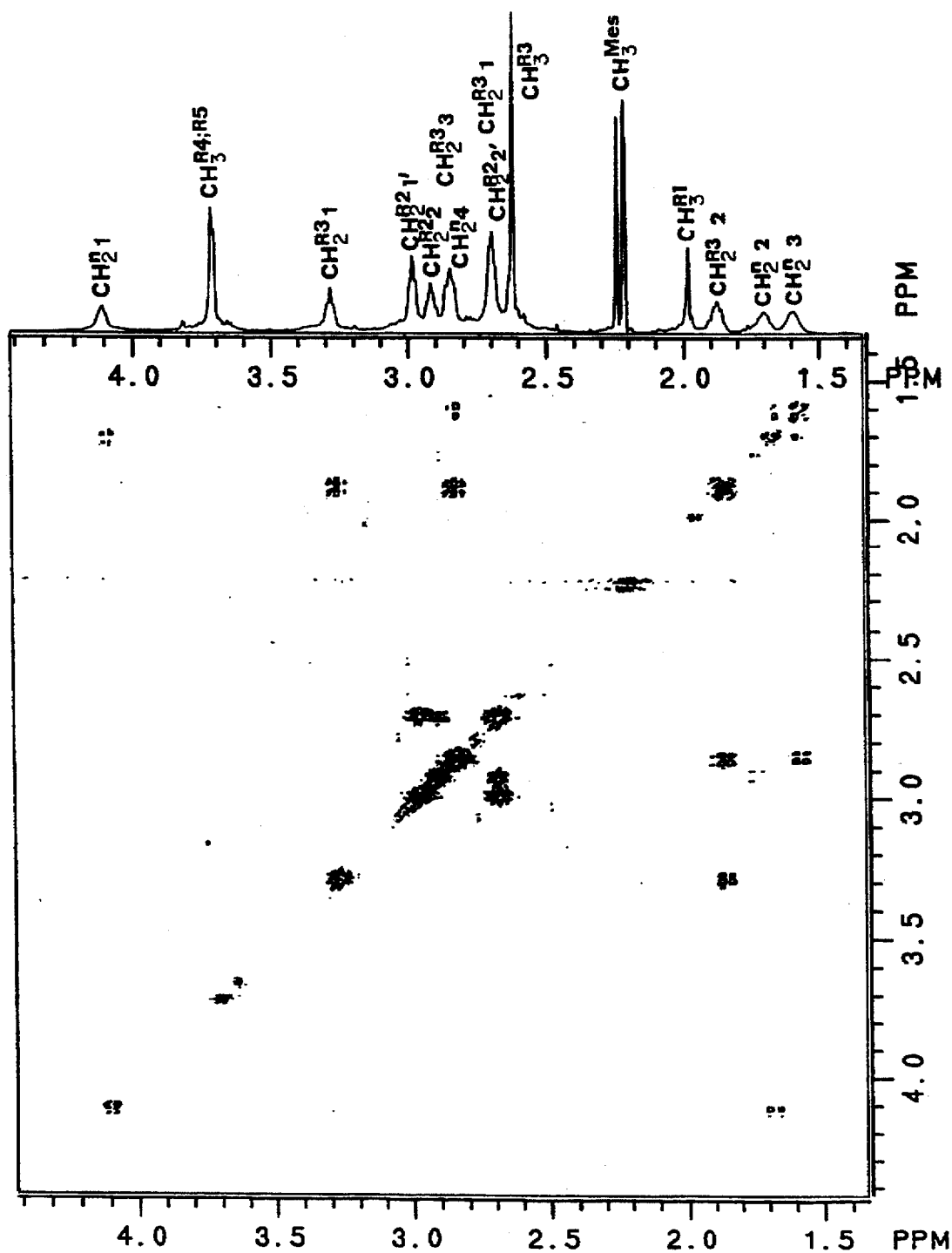

FIG. 21. DQF-COSY spectrum of 6b, $2.5 \times 10^{-3}$M in 10 mM phosphate buffer, pH 7.0, 10 mM NaCl at 10° C.

Figure 22:
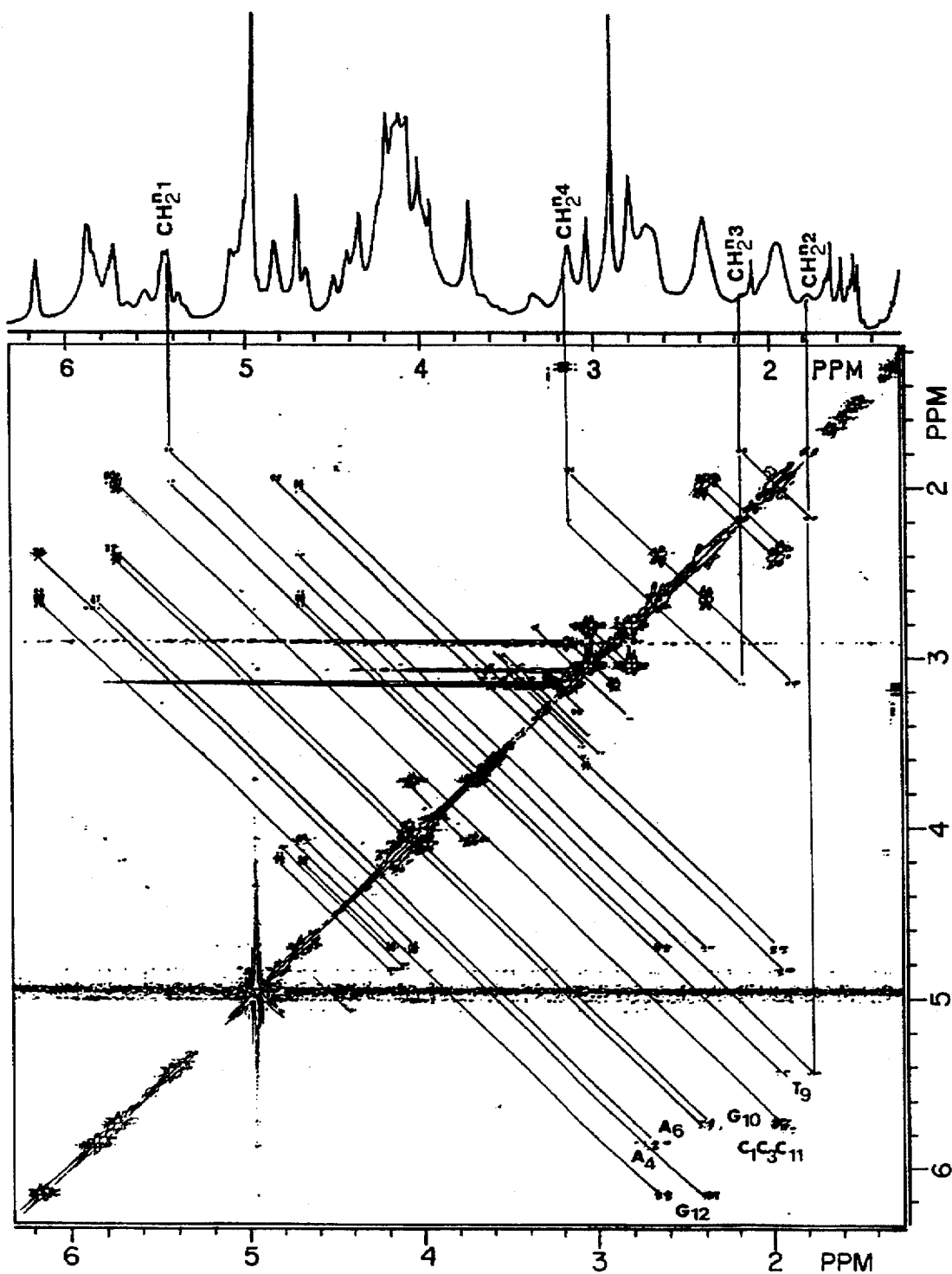

FIG. 22. Expansion of the DQF-COSY spectrum of the 6b: d(CGCAAATTTGCG (SEQ ID NO:3))₂ complex in the (1.2–6.4)×(1.2–6.4) ppm region.

Figure 23:
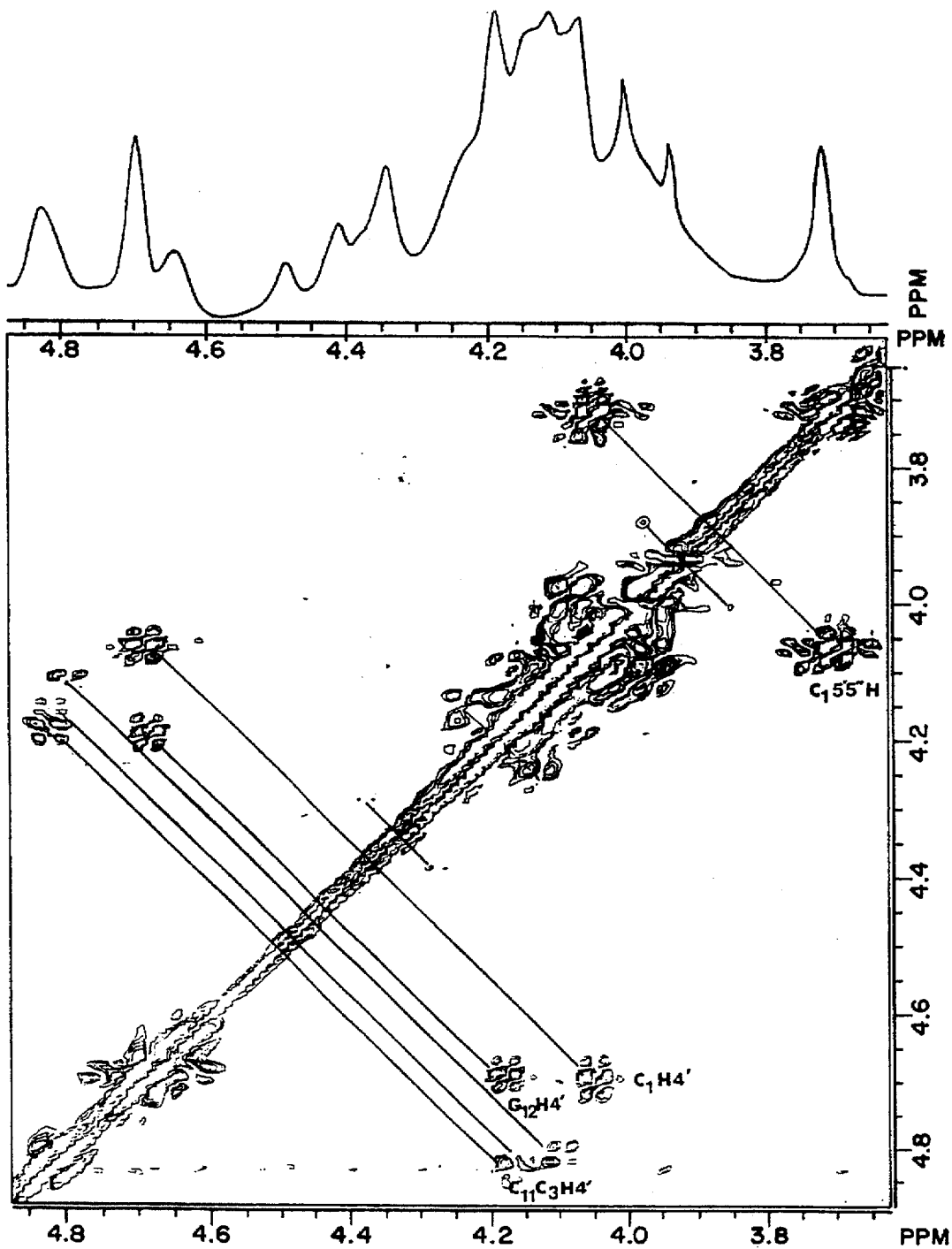

FIG. 23. Expansion of the DQF-COSY spectrum of the 6b: d(CGCAAATTTGCG (SEQ ID NO:3))₂ complex in the (3.6–4.9)×(3.6–4.9) ppm region.

Figure 24:
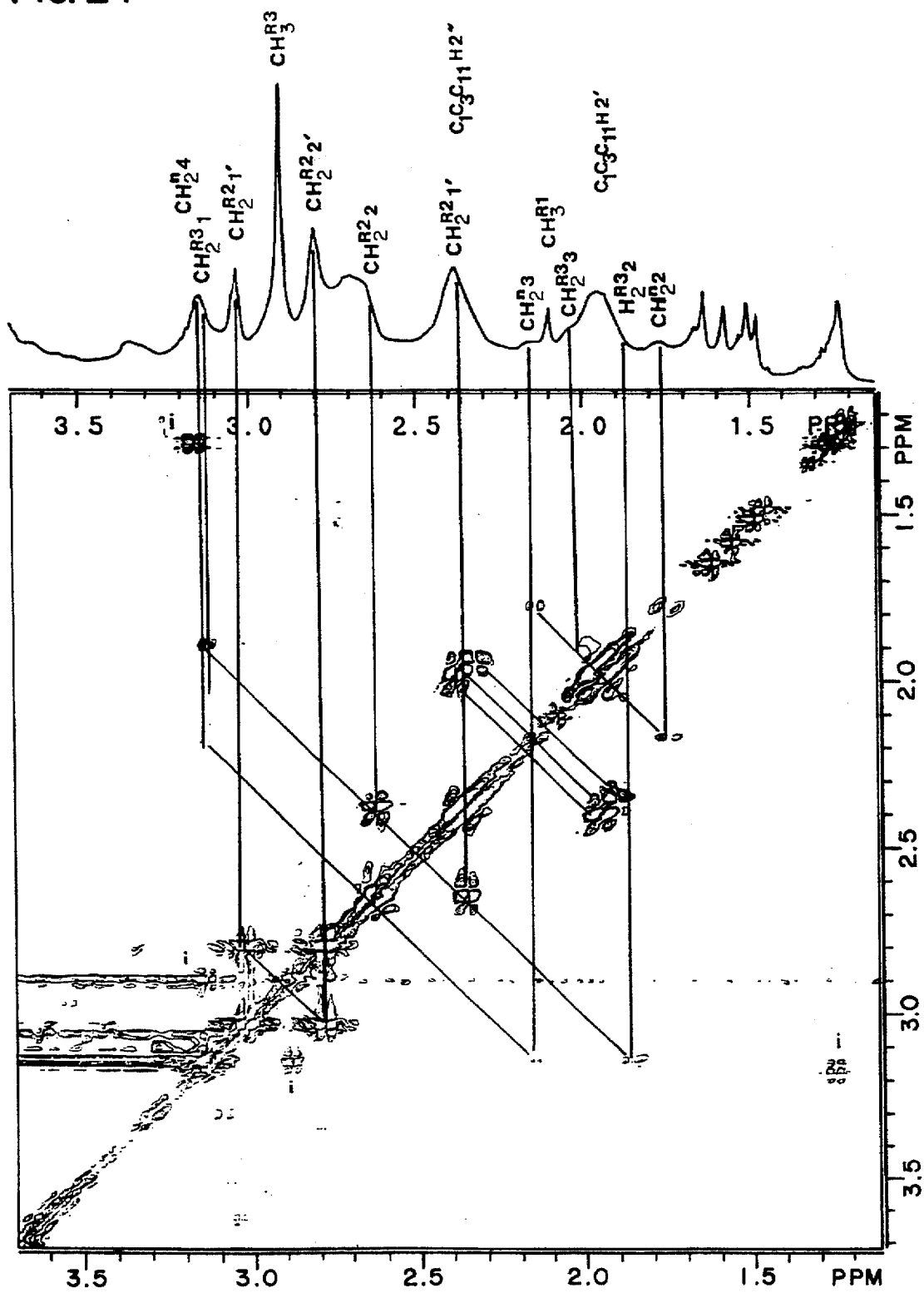

FIG. 24. Expansion of the DQF-COSY spectrum of the 6b: d(CGCAAATTTGCG (SEQ ID NO:3))₂ complex in the (1.1–3.7)×(1.1–3.7) ppm region.

Figure 25:
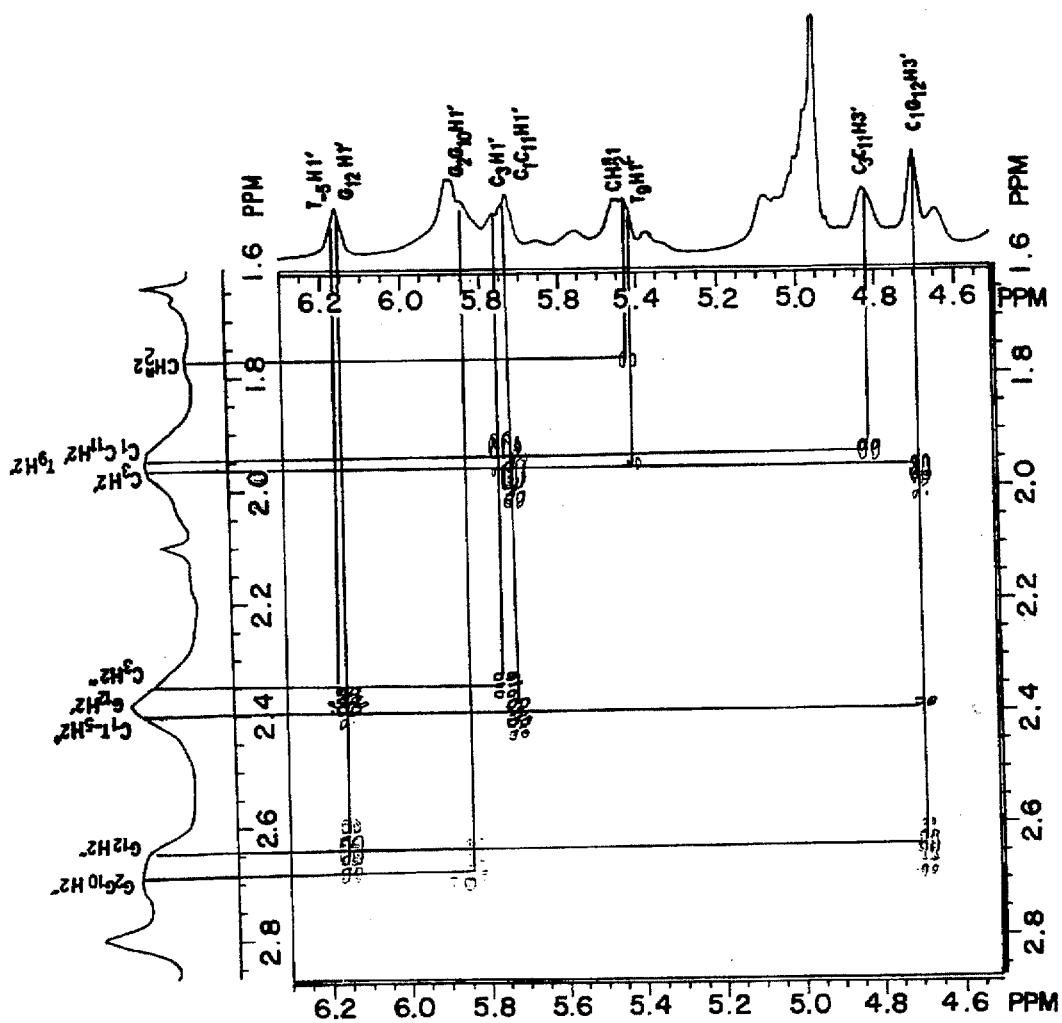

FIG. 25. Expansion of the DQF-COSY spectrum of the 6b: d(CGCAAATTTGCG (SEQ ID NO:3))₂ complex in the (4.5–6.3)×(1.6–2.9) ppm region.

Figure 26:
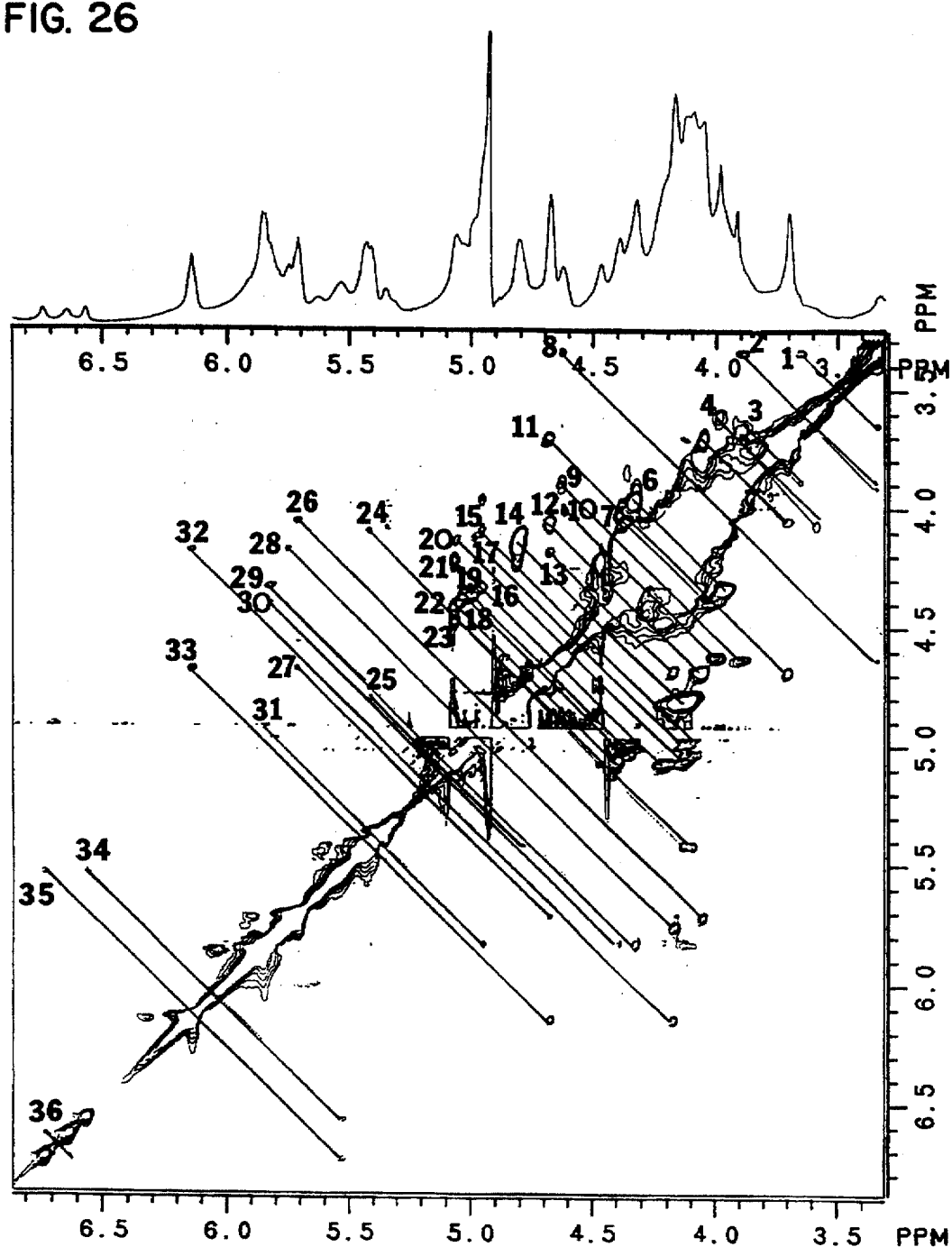

FIG. 26. Expansion of the NOESY spectrum of the 1:1 complex in the (3.3–6.9)×(3.3–6.9) ppm region. 1. $T_8H4'$-$T_8H5'$; 2. $T_8H5'$-$T_8H5''$; 3. $T_8H4'$-$T_8H5''$; 4. $CH_3^{R5}$-$T_8H4'$; 5. $C_1H5'$-$C_1H5''$; 6. $G_{-3}H5'$-$G_{-3}H5''$; 7. $G_{10}H4'$-$G_{10}H5'$; 8. $T_8H3'$-$T_8H5''$; 9. $T_8H3'$-$T_8H5'$; 10. $T_7H3'$-$T_7H5''$; 11. $C_1H3'$-$C_1H5'$; 12. $C_1H3'$-$C_1H5'$, $G_{12}H3'$-$G_{12}H5''$; 13. $G_{12}H3'$-$C_{12}H5'$; 14. $C_3H3'$-$C_3H5'5''$, $C_{11}H340$ -$C_{11}H5'5''$; 15. $G_{-3}H3'$-$G_{-3}H5''$;16. $G_{-3}H3'$-$G_{-3}H5'$, $G_2H3'$-$G_2H5''$; 17. $G_{10}H3'$-$G_{10}H5''$; 18. $G_{10}H3'$-$G_{10}H5'$; 19. $A_5H3'$-$A_5H5''$; 20. $A_6H3'$-$A_6H5''$; 21. $A_4H3'$-$A_4H5''$; 22. $A_6H3'$-$A_6H5'$; 23. $A_4H3'$-$A_4H5'$; 24. $C_3C_{11}H5$-$C_3C_{11}H5''$; 25. $C_3C_{11}H5$-$C_3C_{11}3'$; 26. $C_1C_{11}H1'$-$C_1C_{11}H4'$; 27. $C_1H1'$-$C_1H3'$; 28. $C_3H1'$-$C_3H4'$; 29. $G_2H1'$-$G_2H4'$; 30. $A_4A_6H1'$-$A_4A_6H4'$; 31. $G_2H1'$-$G_2H3'$; 32. $G_{12}H1'$-$G_{12}H4'$; 33. $G_{12}H1'$-$G_{12}H3'$; 34. $H6$-$A_{-8}H1'$; 35. $H4$-$A_{-8}H1'$; 36. $H4$-$H2$.

Figure 27:
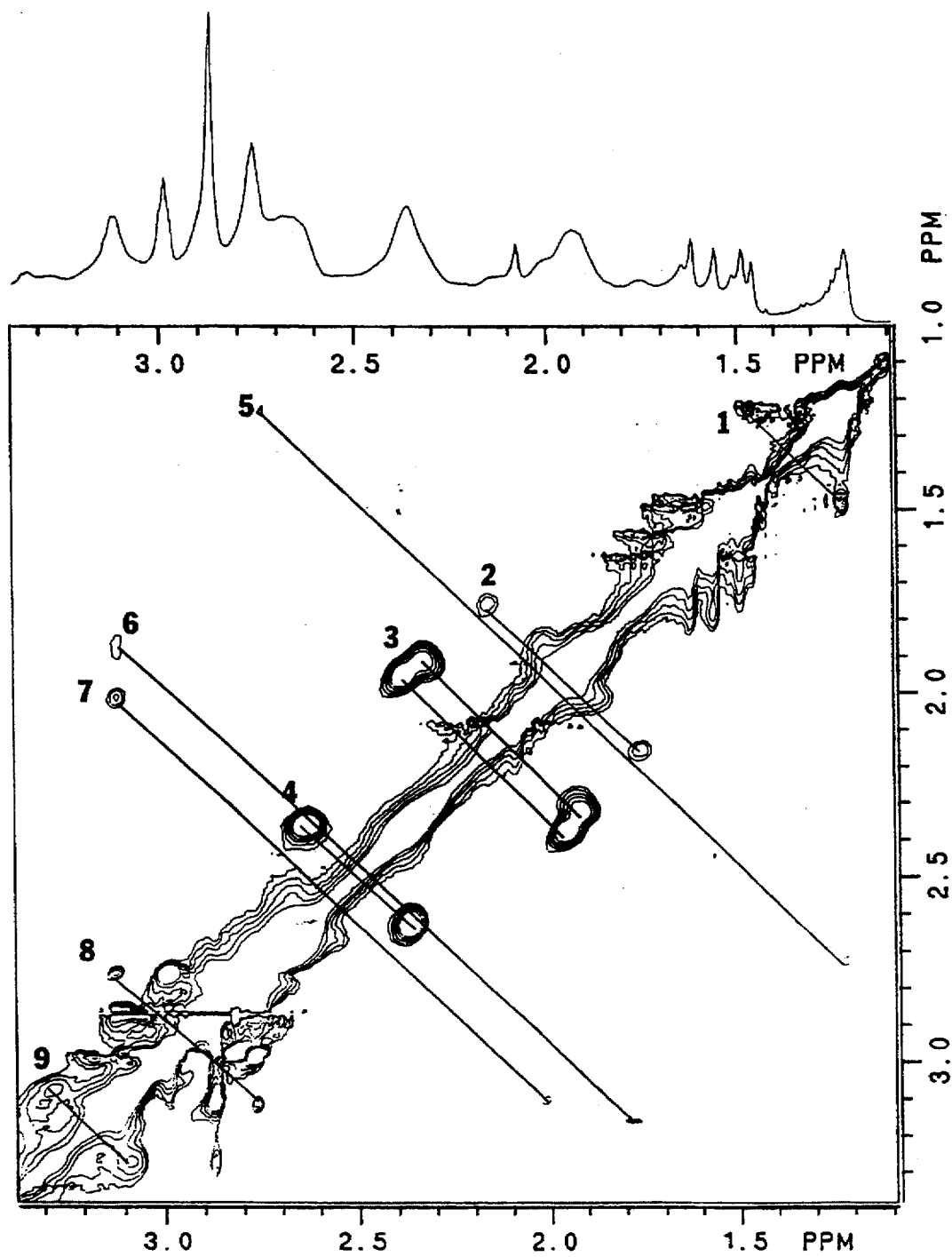

FIG. 27. Expansion of the NOESY spectrum of the 1:1 complex in the (1.0–3.4)×(1.1–3.4) ppm region. 1. $T_7CH_3$—$T_8CH_3$, $T_{-5}CH_3$_$T_{-5}CH_3$; 2. $CH_2^n$ (3)-$CH_2^n$(2); 3. $T_7T_8T_9H2'$-$T_7T_8T_9H2''$; 4. $CH_2^{R2}$(2)-$CH_2^{R2}$(1); 5. $T_{-6}CH_3$-$A_6H2''$; 6. $CH_2^{R3}$(1)-$CH_2^{R3}$(2); 7. $CH_2^{R3}$(1)-$CH_2^{R3}$(3); 8. $CH_2^{R2}$(2')-$CH_2^n$(4); 9. $T_8H5''$-$CH_2^n$(4).

Figure 28:
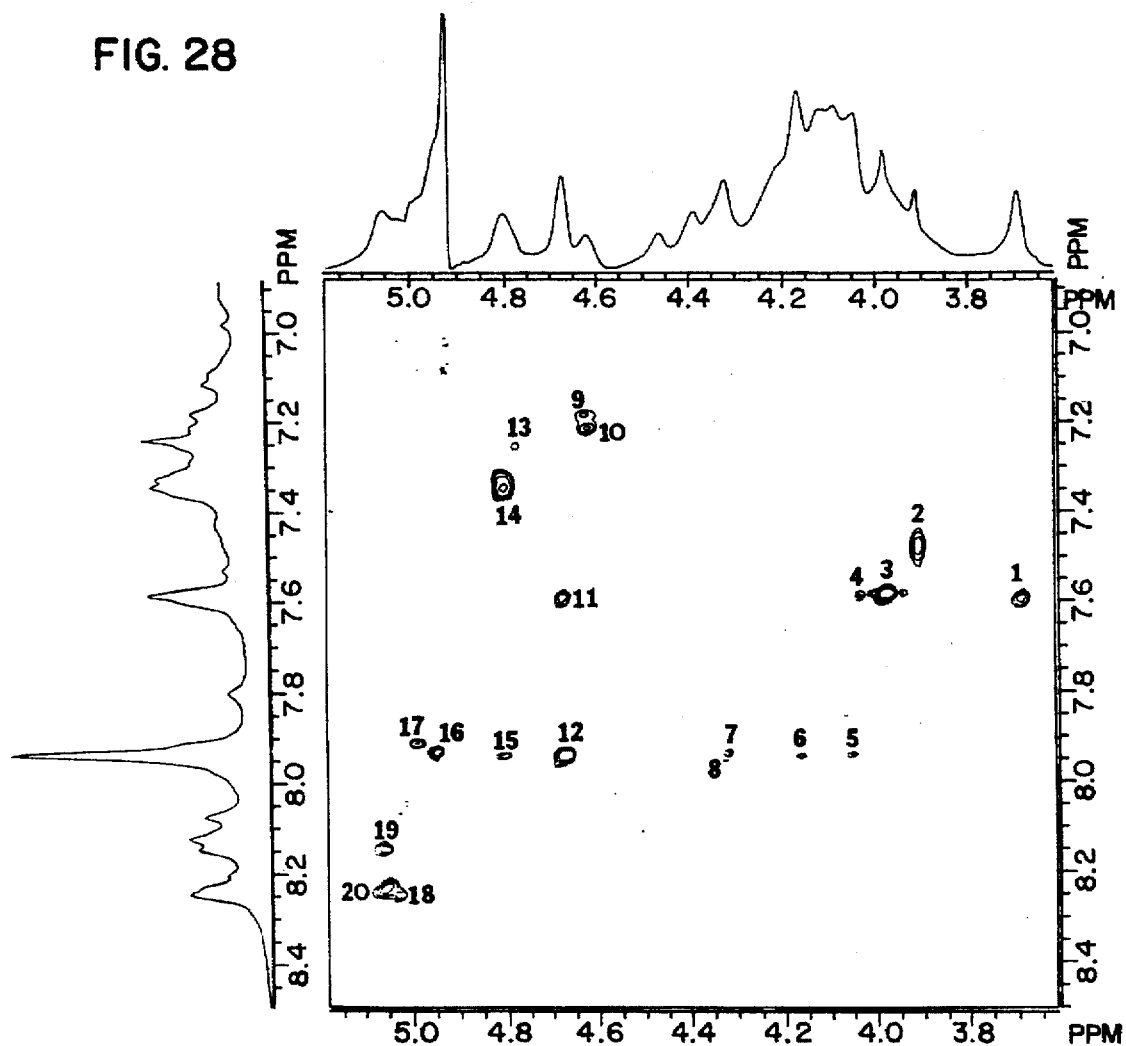

FIG. 28. Expansion of the NOESY spectrum of the 1:1 complex in the (3.6–5.2)×(6.9–8.5) ppm region. 1. $C_1H6$-$C_1H5'$; 2. $T_7H5''$-$A_6H2$; 3. $C_{-12}H6$-$C_{-12}H5'$; 4. $C_1H6$-$C_1H5'$; 5. $G_{-3}G_{12}H8$-$G_{-3}G_{12}H5''$; 6. $G_{12}H8$-$G_{12}H5'$; 7. $G_{-3}H8$-$G_{-3}H5'$; 8. $G_2H8$-$G_2H5''$; 9. $T_8H6$-$T_8H3'$; 10. $T_{-5}H6$-$T_{-5}H3'$; 11. $C_1H6$-$C_1H3'$; 12. $G_{12}H8$-$G_{12}H3'$; 13. $T_{-4}H6$-$T_{-4}H3'$; 14. $C_3C_{11}H6$-$C_3C_{11}H3'$; 15. $G_{12}H8$-$C_{11}H3'$; 16. $G_2H8$-$G_2H3'$; 17. $G_{-3}H8$-$G_{-3}H3'$; 18. $A_5H8$-$A_5H3'$; 19. $A_6H8$-$A_6H3'$; 20. $A_4H8$-$A_4H3'$, $A_{-8}H8$-$A_{-8}H3'$.

Figure 29:
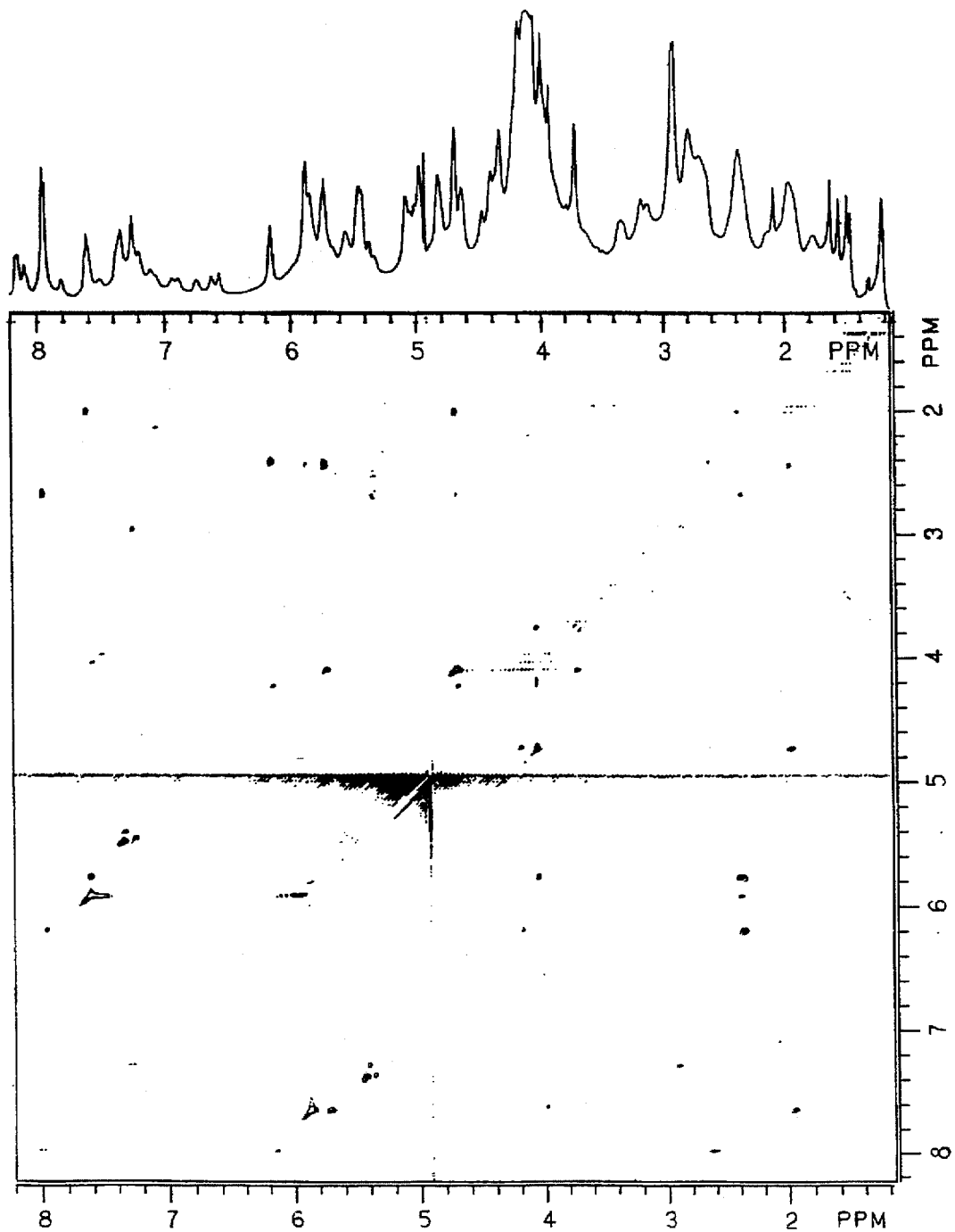

FIG. 29: ROESY spectrum of the 1:1 complex at a mixing time of 50 ms and a spin locking field strength of 2.5 kHz.

Figure 30A:
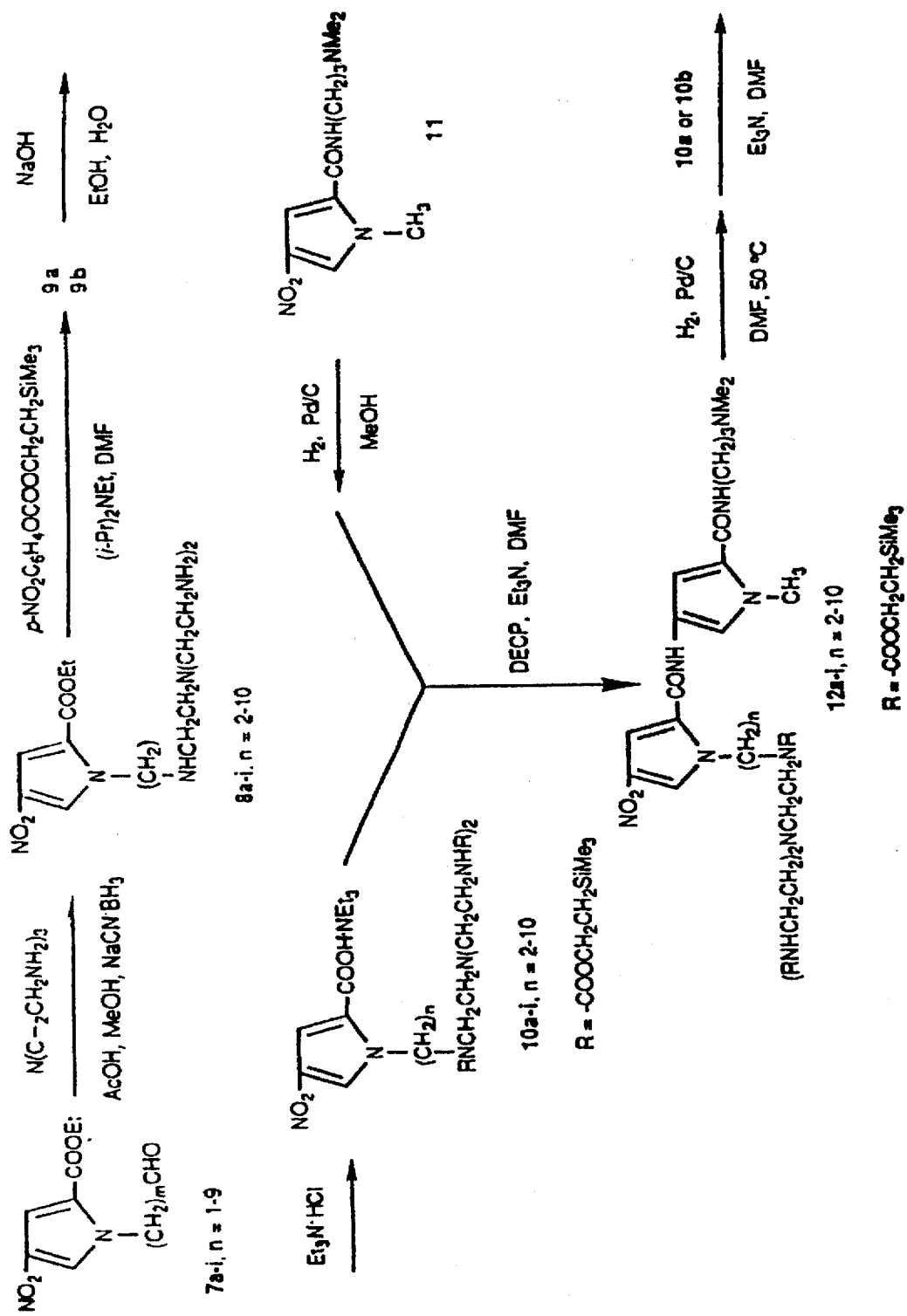
Figure 30:
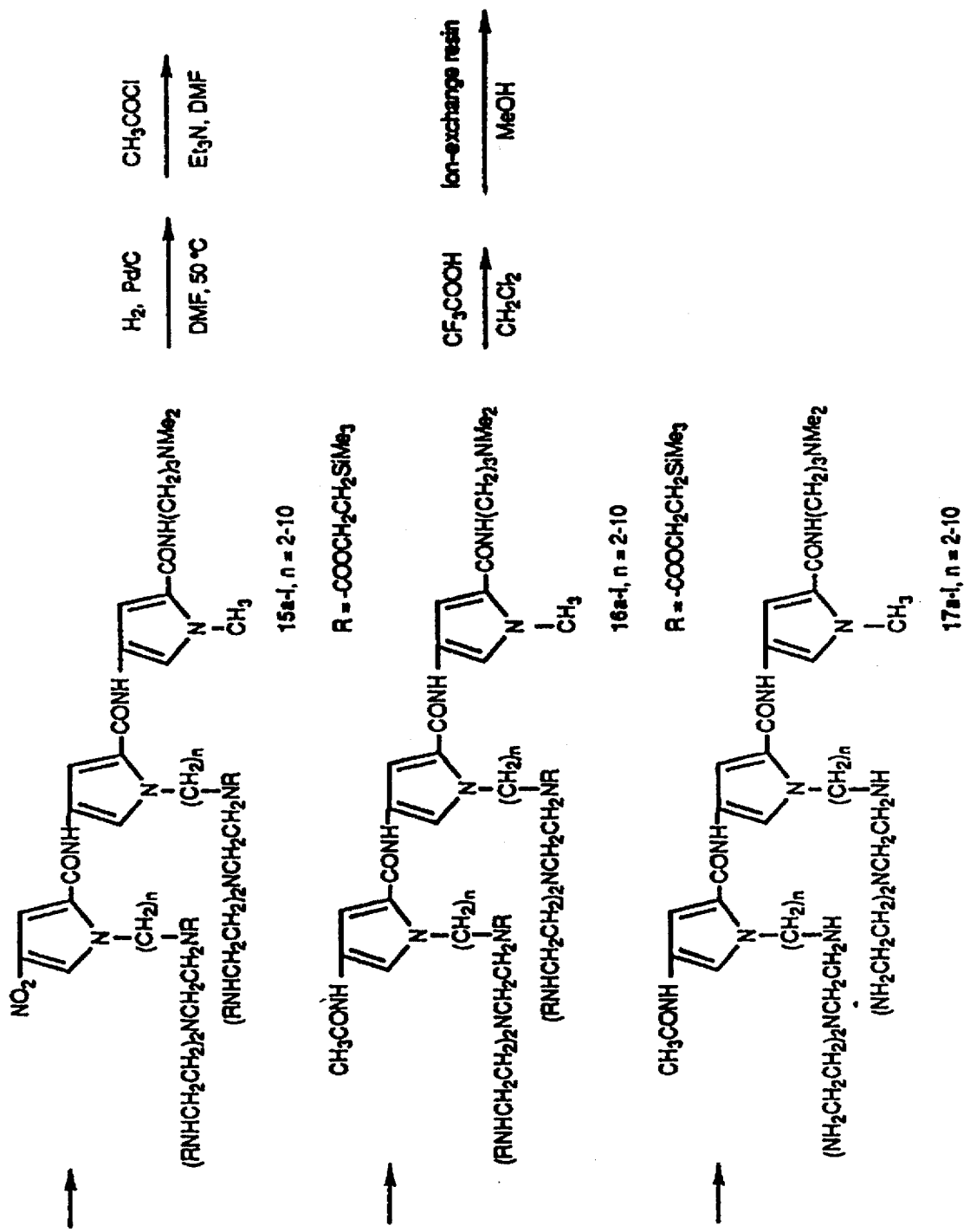

FIG. 30. A schematic diagram showing the synthesis of a microgonotropen molecule having two polyamine groups. The first polyamine group is located on the ring N of the first pyrrole ring. The second polyamine group is located on the ring N of the second pyrrole ring.

DETAILED DESCRIPTION OF THE INVENTION

PEPTIDES OF The INVENTION

The present invention provides five-membered triheterocyclic peptides useful for binding DNA. The five-membered triheterocyclic peptides include first, second, and third heterocyclic moieties. Each of the first, second, and third heterocyclic moieties can be a pyrrole, a furan, a thiophene, an imidazole, an oxazole, a thiazole or a pyrazole, (J. Am. Chem. Soc. 1988, 110, 3641–3649; J. Am. Chem. Soc. 1992, 114, 5911–5919; J. Am. Chem. Soc. 1933, 115, 7061–7071).

The heterocyclic moieties of the triheterocyclic peptide may be the same or different, i.e., the first heterocyclic compound may be the same or different from the second or third heterocyclic moiety. Alternatively, the second heterocyclic compound may be the same or different from the first or third heterocyclic moiety. Further alternatively, the third heterocyclic compound may be the same or different from the first or second heterocyclic moiety.

A polyamine group is attached to the first, second, and/or third heterocyclic moieties of the triheterocyclic peptide. The polyamine group comprises a methylene linker which extends up from a ring nitrogen, towards the phosphate backbone and major groove of DNA and a ligand to which the methylene linker is attached. The ligand binds metal ions, phosphate substituents, and/or the floor of the major groove of DNA. At least one but no more than three polyamine groups are present on the triheterocyclic peptides of the invention.

In one embodiment of the present invention, the triheterocyclic peptide is a tripyrrole peptide having first, second, and third pyrrole rings having the following formula:

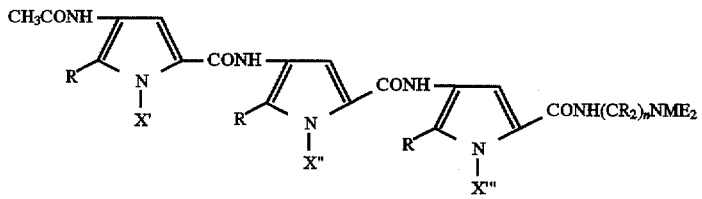

The R group in the triheterocyclic peptide is a hydrogen (H) atom, a lower alkyl group, or halogen atom. A lower alkyl group includes aliphatic hydrocarbons having between one to five carbon atoms.

Each of X', X", and X"' is $CR_3$, $(CR_2)_n$-NRY, or $(CR_2)_n$-$CR_2$Y. At least one of X', X", or X"' is other than $CR_3$. n is an integer from 2 to 10. Y is a polyamine group.

In accordance with the practice of the invention, when the five membered heterocyclic moiety is a pyrrole, imidazole, pyrazole, 3-pyrroline, or pyrrolidine, the polyamine linkers extend from the ring nitrogen(s) towards the phosphate backbone and major groove. Typically, the peptide of the invention is a tripyrrole peptide.

Preferably, the peptide of the invention is capable of binding DNA. As a result of such binding, the peptides of the invention prevent or inhibit the binding of DNA with an enzyme important in DNA replication and/or genetic expression.

The peptide of the invention has a polyamine group attached to the nitrogen atom of the second pyrrole of the tripyrrole peptide. Further, it has the following characteristics. In one embodiment, the peptide of the invention is capable of binding the minor groove of DNA with an equilibrium constant of $\geq 10^9 M^{-1}$. Further, the peptide of the invention is incapable of alkylating the enzyme or DNA.

In one embodiment of the invention, the tripyrrole peptide has a first, second, and third pyrrole ring. Moreover, the peptide is capable of binding the minor and major grooves of DNA. This binding alters the conformation of DNA. In this embodiment, the peptide having a polyamine group attached to the nitrogen atom of the second pyrrole of the tripyrrole peptide, the peptide having the formula:

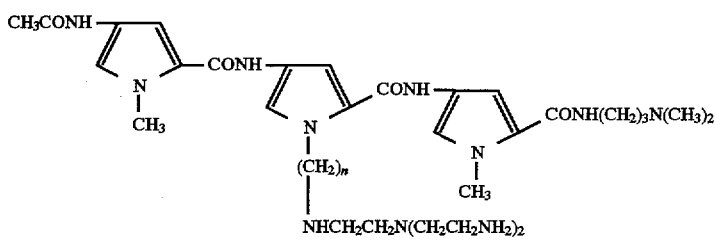

In accordance with the practice of the invention, $(CH_2)_n$ is an alkyl linker of varied chain length. Preferably, n is 2, 3, 4, 5, 6, 7, 8, 9, or 10. R is hydrogen, a lower alkyl, or a halogen such as fluorine, chlorine, bromine, and iodine.

In one embodiment, the tripyrrole peptide is a tren-microgonotropen molecule. For example, the tren-microgonotropen molecule comprises a polyamine group having the formula $-(CH_2)_3NHCH_2CH_2N(CH_2CH_2NH_2)_2$. This polyamine group is attached to the molecule at the second pyrrole of the tripyrrole peptide.

In another embodiment, the polyamine group of tren-microgonotropen has the formula $-(CH_2)_4NHCH_2CH_2N(CH_2CH_2NH_2)_2$. This polyamine group is attached to the molecule at the second pyrrole of the tripyrrole peptide.

In one embodiment, the polyamine group of the triheterocyclic peptide is a molecule which binds the major groove of DNA through the phosphodiester linkage and is a lower alkyl group substituted with least one nitrogen atom. An example includes cyclen derivative such as 1,4,7,10-tetraazacyclododecane.

The structures of two cyclen derivatives are as follows:

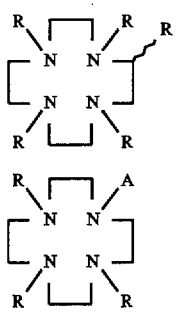

A is the attachment site to the heterocyclic compound.

Another suitable polyamine group includes derivatives of 1,4,7-triazacyclononane having the following structures:

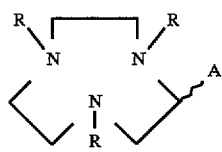

A is the attachment site to the heterocyclic compound.

Additionally, trpn derivatives are suitable polyamine groups of the invention. For example, tris(3-aminopropyl) amine is a suitable trpn derivative having the following structure:

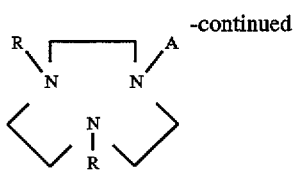

A is the attachment site to the heterocyclic compound.

Further, suitable examples of polyamine groups include derivatives of 1,5,9-triazacyclododecane. Some chemical structure of such derivative are as follows.

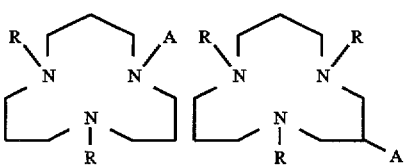

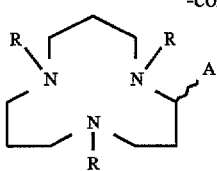

A is the attachment site to the heterocyclic compound.

Additionally, other polyamine groups include the following:

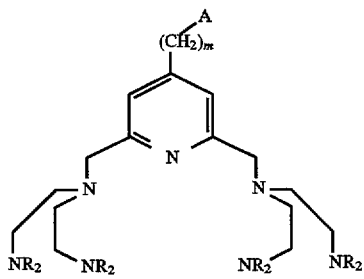

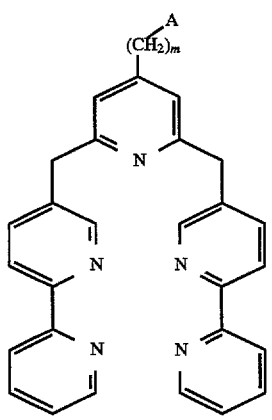

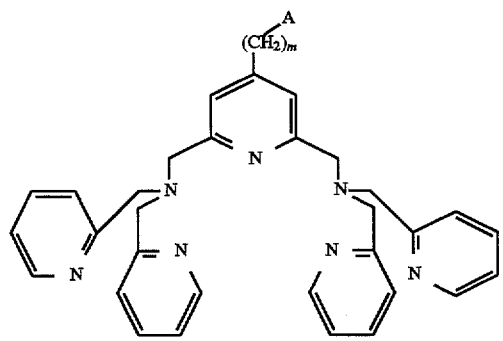

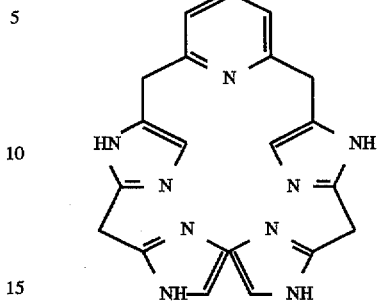

A is the attachment site to the heterocyclic compound.

In the above-described polyamine groups, A indicates the attachment site and the wavy line indicates that the substituent could have either a R or a S chiral center. Further, m is an integer of 1 to 5.

In another embodiment of the invention, the peptide of the invention exhibits nonintercalative binding to DNA. In this case, the polyamine group is capable of forming a complex with a metal ion. Alternatively, or additionally, the polyamine group includes four aliphatic amino groups. Two of the aliphatic amino groups may be primary amino groups. Alternatively, or additionally, one of the aliphatic amino groups may be a secondary amino group. Further, in one embodiment of the invention, one of the aliphatic amino groups is a tertiary amino group.

In another embodiment of the invention, the amino terminus of the peptide is acetylated.

In yet another embodiment of the invention, the carboxyl terminus of the peptide has an amide linkage to β-(N,N-dimethylamino)propylamine.

In a further embodiment, the ring nitrogen of the first and third pyrrole rings are N-methylated.

Additionally, in yet a further embodiment, the peptide of the invention binds the minor groove of DNA at A+T-rich regions of DNA.

The present invention further provides a tren-microgonotropen having the formula

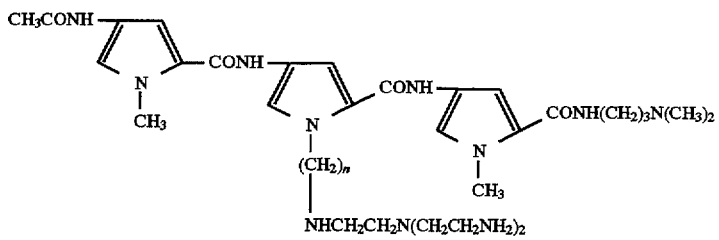

wherein n represents an alkyl linker of varied chain length. Preferably, n represents 2, 3, 4, 5, 6, 7, 8, 9, or 10. In one embodiment, the tren-microgonotropen is designated 6b as shown in FIG. 15. 6b binds into the minor groove at A+T-rich regions of DNA.

Microgonotropen 6b possesses five aliphatic amino groups: two primary, one secondary and one tertiary in the tren substituent (—$CH_2CH_2CH_2CH_2NHCH_2CH_2N$ ($CH_2CH_2NH_2)_2$) and one tertiary in the dimethyl propylamino tail (—$CH_2CH_2CH_2N(CH_3)_2$). The extent of their protonation when 6b is lodged in the minor groove is not certain.

Further, as shown above, when compared with 5c and distamycin, only 6b is able to effectively compete with the enzyme topoisomerase I (topoI) once the enzyme is bound. Apparently, binding of 6b to DNA alters the conformation of DNA. Such an altered DNA conformation could inhibit topoI by either preventing enzyme binding to or "tracking" along DNA, or by generating conformationally uncleavable sites.

The three primary amines of 6b's tren amino substituent are located within 1.75 Å of two phosphodiester oxyanions while the fourth amine (tertiary) is 3.0 Å from the same two adjacent phosphodiester oxyanions.

The increased binding affinity of 6b over distamycin is likely due to the electrostatic interactions of the polyamino side chain with the phosphodiester linkages. The central polyamino groups of 6b are significant to its binding affinity.

6b binds to the A+T-rich region of dsDNA involving one G.C residue flanking the A.T binding sites. Unlike 5c, the —$CH_2CH_2CH_2N(CH_3)_2$ tail of 6b is completely within the minor groove. This also contributes to its increased binding affinity to DNA.

The tren substituent of 6b (—$(CH_2)_4NHCH_2CH_2N$ ($CH_2CH_2NH_2)_2$) interacts with two adjacent phosphates; this increases 6b's affinity for DNA. The efficiency of binding of the tren substituent of 6b (as seen by the embedding of the tripyrrole peptide in the minor groove) when compared with the dien substituent of 5c can be ascribed to the smaller steric effect around the terminal amino groups of the tren allowing a better pairing with the phosphate backbone of dsDNA.

Tren-microgonotropen-b, 6b, (i) penetrates deeper into the minor groove of dsDNA than 5c, (ii) exhibits a stronger interaction with the phosphate backbone as compared to 5c, and (iii) has a hydrocarbon linker between the tripyrrole peptide and the tren substituent that is shorter than the linker in 5c.

METHODS OF MAKING THE PEPTIDES OF THE INVENTION

FIG. 16 is a schematic diagram showing the organic synthesis of tren-microgonotropen as described in Example I.

In the embodiment when R is a halogen, attachment of the halogen to pyrrole carbons is by methods known in the art (J. Org. Chem. 1987 52, 3493–3501). Further, attachment of aliphatic groups on the carbons of pyrrole groups is by methods known in the art (J. Org. Chem. 1987, 52, 3493–3501).

Further, attachment of alkyl groups, e.g., a propyl group (Cold Spring Harbor Symp. Quant. Biol. 1983, 47, 367–378) or an isoamyl (Bioorg. Khim. 1982, 8, 1070–1076) group, to the ring nitrogen of a pyrrole compound is by methods known to those skilled in the art. Additionally, the methylene tail of the dimethylamine carboxy terminus may be of various lengths (J. Am. Chem. Soc. 1988, 110, 3641–3649). Moreover, other positively charged groups may replace the dimethylamine terminus (i.e., amidine (J. Am. Chem. Soc. 1988, 110, 3641–3649)).

In another embodiment, FIG. 30 is a schematic diagram showing the organic synthesis of a microgonotropen molecule having two polyamine groups to bind DNA.

METHODS OF USING THE PEPTIDES OF THE INVENTION

The invention provides a method for inhibiting the replication of DNA. This method comprises contacting the peptide of the invention (for example, tren-microgonotropen) with DNA so that the peptide and DNA form a peptide-DNA complex. The complex binds tightly and/or induces a conformational change in the DNA so complexed.

The peptide of the invention prevents binding of an enzyme necessary for DNA replication with the peptide-DNA complex so as to inhibit the replication of DNA so complexed.

In one embodiment, the enzyme is a topoisomerase. The topoisomerase may be mammalian topoisomerase I.

The present invention provides a composition comprising an effective amount of the peptide of the invention and a suitable pharmaceutical carrier.

Compositions of the invention can be administered using conventional modes of administration including, but not limited to, intravenous, intraperitoneal, oral, intralymphatic or administration directly into the tumor.

Alternatively, the compositions of the invention may be applied topically, like distamycin A, a related compound, in the form of a 1% ointment or paste for cutaneous or mucocutaneous infections produced by herpes simplex, varicella-zoster, and vaccinia viruses.

In accordance with the practice of this invention, the composition of the invention may be administered to a subject such as human, equine, porcine, bovine, murine, canine, feline, and avian subjects. Other warm blooded animals may also be administered with the peptide of the invention.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient.

An effective dose of the compositions of this invention may be in the range of from about 1 to about 2000 mg/m$^2$. Additionally, as a guideline for determining dosages of the triheterocyclic peptide of the invention, it is important to keep in mind that the LD$_{50}$ of distamycin A in mice is 75 mg/kg i.v. and 500 mg/kg i.p.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the location of the tumor being treated, the severity and course of the cancer, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. Cancer Chemother., Rep. 50 (4): 219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation.

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a non-ionic detergent. Examples of non-ionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

The present invention further provides a method for inhibiting the growth of tumor cells. This method comprises contacting tumor cells with an effective tumor growth-inhibiting amount of the composition of the invention.

The peptide of the invention has many diagnostic in vitro uses. For example, since the peptide binds the major and minor grooves of DNA, the peptide may be used to detect the presence of DNA. Frequently, assays require DNA free samples. The presence of DNA can often cause false positives to increase. Alternatively, the presence of DNA may prohibit the proper binding of the reagents. Therefore, no binding occurs. Further, in some assays the detection of DNA or RNA, e.g., viral DNA or RNA may be useful.

For example Creuzfeld-Jakob disease is a neurodegenerative disease caused by transmissible agents that cause slow, progressive neuronal loss. Even after extensive efforts no viral DNA or RNA has been demonstrated as infectious material. Moreover, no one has ever determined whether an immune response to the virus has been exhibited.

The neuropathology of Creuzfeld-Jakob is characterized by formation of amyloid plaques (insoluble protein deposits), spongiform encephalopathy (the appearance of prominent vacuoles in cells), and gliosis (reaction proliferation of glia).

It would be useful to develop a routine screening assay for detecting the presence of viral DNA or RNA in infectious material. The DNA or RNA so detected may be isolated and identified as a marker for the disease. The peptides of the invention would be useful in making this determination.

Another example of a situation in which the detection of trace amounts of nucleic acid is useful arises from the purification of a protein produced on a large scale by genetic engineering. Typically, these proteins are purified by affinity chromatography or other chromatographic procedures; the presence of small quantities of nucleic acid remaining from the purification procedure would be unwelcome. It would therefore be highly desirable to have a test by which the presence of small quantities of nucleic acid in such preparations could be detected, without having to rely on hybridization or another sequence-specific assay for nucleic acid.

Detection of DNA or RNA can be accomplished using various methods by direct or indirect labeling methods. For example, using the peptides of the invention, a label is attached directly to the peptide by a covalent bond, or the label intercalates noncovalently between the double strand of the peptide:target complex. The latter method, indirect labeling, employs a specific binding partner (e.g., biotin) attached to the nucleic acid probe. The hapten is detected using a labeled specific binding protein (e.g., antibiotin, avidin, or streptavidin). A slightly more complex format uses an intermediate binding protein to bridge between the hapten and the labeled binding protein. Alternatively, a binding protein specific for double-stranded DNA can be used (e.g., monoclonal anti-dsDNA) and complexes are then detected using a labeled antispecies antibody.

ADVANTAGES OF THE INVENTION

The present invention has advantages over distamycin and analogs thereof.

Tren-microgonotropens provide a 2-fold greater binding to DNA than generated by the dien-microgonotropens. Further, tren-microgonotropens are about twice as effective in inducing structural changes in DNA as are the dien-microgonotropens and at least four times as effective in inducing structural changes as is Distamycin (Dm). The structure of tren-microgonotropen is as follows.

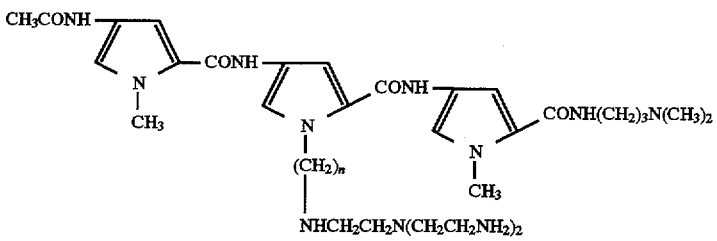

Further, the microgonotropens of the present invention are advantageous over distamycin and analogs thereof since microgonotropens bind tightly to the minor groove of DNA since they are tripeptides of 3-aminopyrrole-2-carboxylic acid.

Also, in one embodiment, the ring nitrogens of two of the three pyrrole rings are N-methylated. Moreover, the ring nitrogen of the second pyrrole carries the ligand such as —(CH$_2$)$_3$NH(CH$_2$)$_2$N{(CH$_2$)$_2$NH$_2$}$_2$ (6a) and —(CH$_2$)$_4$NH(CH$_2$)$_2$N{(CH$_2$)$_2$NH$_2$}$_2$ (6b).

Another advantage is that the electrophoretic mobilities of φX-174-RF DNA HaeIII restriction fragments complexed to 6a or 6b revealed a much greater conformational change in the DNA fragments when compared to distamycin (Dm) bound to the same fragments. Further, the result of this greater conformational change is about a 2-fold greater binding to DNA than generated by the dien-microgonotropens.

For example, complete inhibition of mammalian topoisomerase I with 30 μM 6b was observed while dien-microgonotropen-b and Dm only partially inhibited topoisomerase I at 150 μM.

Evidence from equilibrium constants for complexation, electrophoretic mobilities, and topoisomerase I assays suggests that 6b alters the conformation of DNA in a manner that is not directly related to the affinity of complexation. Further, the ability to alter the conformation of DNA with small organic molecules at selected sites may have profound consequences on influencing DNA modifying enzymes and on controlling regulation of genetic expression.

In order that the invention described herein may be more fully understood, the following examples are set forth. It should be understood that these examples are for illustrative purposes only and are not to be construed as limiting the scope of this invention in any manner.

EXAMPLE I

Experimental Section
Organic Synthesis Materials

Reagent grade chemicals were used without purification unless otherwise stated. Methanol was refluxed and distilled from CaH$_2$. Dimethylformamide (DMF) was dried by CaH$_2$ overnight and distilled under reduced pressure. Triethylamine was dried by KOH and distilled. Methanol, DMF, and trimethylamine were stored over 4A molecular sieves. Tetrahydrofuran (THF) was refluxed with sodium (Na) metal and distilled before use. Tris(2-aminoethyl)amine, diisopropylethylamine, and diethyl cyanophosphonate (DECP) were purchased from Aldrich (Milwaukee, Wis.).

2-(Trimethylsilyl)ethyl p-nitrophenyl carbonate and t-butyl S-4,6-dimethyl-pyrimid-2-yl thiocarbonate were purchased from Fluka (Ronkonkoma, N.Y.). After treatment with 1M NaOH, ion-exchange resin (Aldrich) was washed with distilled water and methanol before using.

Ethyl 1-(3-propal)-4-nitro-2-pyrrole-carboxylate (7a), ethyl 1-(4-butal)-4-nitro-2-pyrrolecarboxylate (7b), and dimethyl 3-(1-methyl-4-nitro-2-pyrrolecarboxamido)-propionamine (11) were synthesized (He, G.-X.; Browne, K. A.; Groppe, J. C.; Blaskó, A.; Mei, H.-Y.; Bruice, T. C. J. Am. Chem. Soc. 1993, 115, 7061).

1-Methyl-4-nitro-2-pyrrolecarbonyl chloride was synthesized from reaction of 1-methyl-4-nitro-2-pyrrolecarboxylic acid, prepared by nitration of 1-methyl-2-pyrrolecarboxylic acid (Aldrich) ((a) Bialer, M.; Yagen, B.; Mechoulam, R. Tetrahedron 1978, 34, 2389; (b) Lown, J. W.; Krowicki, K. J. Org. Chem. 1985, 50, 3774; (c) Youngquist, R. S. Ph. D. Dissertation, California Institute of Technology, 1988), and thionyl chloride according to the published methods (Lown, J. W., et al., supra; Rao, K. E.; Bathini, Y.; Lown, J. W. J. Org. Chem. 1990, 55, 728).

General organic synthesis methods

Infrared (IR) spectra were obtained in KBr or neat on a Perkin-Elmer monochromator grating spectrometer (Model 1330). Low-resolution mass spectra (LRMS) were recorded on a VG Analytical spectrometer (Model VGII-250) by fast atom bombardment (FAB) using m-nitrobenzyl alcohol (NBA) as a matrix. High-resolution mass spectrometry (HRMS) was performed at the Midwest Center for Mass Spectrometry Laboratory at the University of Nebraska (Lincoln, Nebr.) using FAB technique and NBA matrix. $^1$H NMR spectra were obtained in CDCl$_3$ or in DMSO-d$_6$ with a General Electric GN-500 spectrometer (Blaskó et al., 1993, supra). Chemical shifts are reported in sigma (ppm) (sigma means units of chemical shifts) relative to CHCl$_3$ (7.24 ppm) or to DMSO (2.49 ppm) with s, d, t, q, and m signifying singlet, doublet, triplet, quartet, and multiplet; coupling constants (J) are reported in hertz (Hz).

Chromatographic Silica Gel (Fisher Chemical, 200–425 mesh) was used for flash chromatography and glass-backed plates of 0.25-mm SiO$_2$ 60-F$_{254}$ (Merck, Darmstadt, Germany) were used for thin-layer chromatography (TLC). All nonaqueous reactions were run under argon with rigorous exclusion of water unless otherwise noted.

The methods described hereinafter are shown in the schematic diagram of FIG. 16.

(8a) To a solution of tris(2-aminoethyl)amine (5.0 g, 34 mmol) and acetic acid (5.0 g, 83 mmol) in 200 mL MeOH, ethyl 1-(3-propal)-4-nitro-2-pyrrolecarboxylate (7a) (1.3 g, 5.4 mmol) in 100 mL MeOH was added dropwise over 30 min at 0° C.

After addition the solution was stirred at room temperature for 72 h. The reaction was followed by TLC (SiO$_2$, hexane:EtOAc=3:1). After complete disappearance of 7a, the solution was concentrated and the residue obtained was dissolved in 300 mL CH$_2$Cl$_2$. The CH$_2$Cl$_2$ solution was washed with 50 mL 1N aqueous NaOH and dried over K$_2$CO$_3$.

Removal of the solvent gave crude 8a which contained <5% impurity as shown by $^1$H NMR, and 8a thus obtained was used in the next reaction without further purification.

8a: 1.7 g, 85%; pale yellow oil; $^1$H NMR(CDCl$_3$): δ1.34(t, J=7, —COO—C—CH$_3$, 3H), 1.87(bs, —NH+

$H_2O$), 1.95(m, —C—$CH_2$—C—, 2H), 2.49–2.76(m, —C—$CH_2$—N—, 14H), 4.28(q, J=7, —COO$CH_2$—C, 2H), 4.44(t, J=7, pyrrole N—$CH_2$—C—, 2H), 7.41(d, J=2, pyrrole Ar—H, 1H), 7.72(d, J=2, pyrrole Ar—H, 1H); LRMS (FAB): 371 (M+H$^+$).

(8b) The procedure used for the synthesis of 8b was much the same as employed for 8a.

8b: 3.1 g, 97%; pale yellow oil; $^1$H NMR(DMSO-$d_6$): δ1.28(t, J=7, —COO—C—$CH_3$, 3H), 1.32–1.60(m, —C—$CH_2$—C—, 2H), 1.65–1.78(m, —C—$CH_2$—C—, 2H), 2.38–2.60(m, —C—$CH_2$—N—, 14H), 3.04(bs, —NH+$H_2O$), 4.25(q, J=7, —COO$CH_2$—C, 2H), 4.34(t, J=7, pyrrole N—$CH_2$—C—, 2H), 7.33(d, J=2, pyrrole Ar—H, 1H), 8.32(d, J=2, pyrrole Ar—H, 1H); LRMS(FAB): 385 (M+H$^+$).

(9a) A solution of 8a (1.7 g, 5 mmol), diisopropylethylamine (5 mL), and 2-(trimethylsilyl)ethyl p-nitrophenyl carbonate in 100 mL MeOH was stirred at 60° C. for 10 h. TLC ($SiO_2$, hexane:EtOAc=1:1) showed complete disappearance of the reactant. After cooling, the solution was concentrated and the residue obtained was dissolved in 300 mL $CH_2Cl_2$.

The organic solution was washed with 100 mL 5% $Na_2CO_3$ aq. and 100 mL sat. aqueous NaCl, and dried over $Na_2SO_4$. Removal of the solvent gave a yellow-oil product mixture which was loaded on $SiO_2$ column, and elution with a solvent mixture of hexane:EtOAc:$Et_3N$=20:10:3 gave pure 9a as a pale yellow viscous oil.

9a: 2.1 g, 52%; TLC ($SiO_2$, hexane:EtOAc:$Et_3N$= 30:10:3): $R_f$=0.37; $^1$H NMR(DMSO-$d_6$): δ–0.10(s, —$SiCH_3$, 27H), 0.82–0.90(m, —$CH_2$Si—, 6H), 1.25(t, J=7, —COO—C—$CH_3$, 3H), 1.85–1.95(m, —C—$CH_2$—C—, 2H), 2.39–2.51(m, —C—$CH_2$—N—, 6H), 2.94–3.18(m, —OCON—$CH_2$—C—, 8H), 3.93–4.00(m, —NCOO—$CH_2$—C—, 6H), 4.22(q, J=7, —COO$CH_2$—C, 2H), 4.30 (bs, pyrrole N—$CH_2$—C—, 2H), 6.77(bs, —OCONH—, 2H), 7.28, 8.29(2s, pyrrole Ar—H, 2H); LRMS(FAB): 803 (M+H$^+$).

(9b) The procedure used for the synthesis of 9b was much the same as employed for 9a.

9b: 4 g, 61%; TLC ($SiO_2$, hexane:EtOAc:$Et_3N$=30:10:3): $R_f$=0.37; IR(Neat): $v_{N-H}$=3300–3500 cm$^{-1}$, $v_{C=O}$= 1680–1720 cm$^{-1}$, $v_{N-O}$=1320, 1510 cm$^{-1}$; $^1$H NMR (DMSO-$d_6$): δ–0.11(s, —$SiCH_3$, 27H), 0.85–0.92(m, —$CH_2$Si—, 6H), 1.26(t, J=7, —COO—C—$CH_3$, 3H), 1.39–1.43(m, —C—$CH_2$—C—, 2H), 1.64–1.67(m, —C—$CH_2$—C—, 2H), 2.41–2.51(m, —C—$CH_2$—N—, 6H), 2.94–3.17(m, —OCON—$CH_2$—C—, 8H), 3.97–4.02 (m, —NCOO—$CH_2$—C—, 6H), 4.25(q, J=7, —COO$CH_2$—C, 2H), 4.36(t, J=7, pyrrole N—$CH_2$—C—, 2H), 6.79(bs, —OCONH—, 2H), 7.31, 8.30(2s, pyrrole Ar—H, 2H); LRMS(FAB): 817 (M+H$^+$).

(10a) NaOH (0.32 g, 8 mmol) in 20 mL $H_2O$ was added to a solution of 9a (2.0 g, 2.5 mmol) in 20 mL EtOH. The resulting solution was stirred at room temperature for 10 h. $Et_3N$·HCl (2.2 g, 16 mmol) was added to the solution when TLC ($SiO_2$, hexane:EtOAc:$Et_3N$=20:10:3) showed disappearance of the reactant. The color of the solution turned from orange to pale yellow.

The solution was concentrated to dryness under reduced pressure and the residue was dissolved in 200 mL $CH_2Cl_2$. The pale yellow organic phase was washed with 30 mL $H_2O$ and dried over $Na_2SO_4$. Removal of the solvent gave the product as a yellow viscous oil.

10a: 1.6 g, 73%; $^1$H NMR(DMSO-d6): δ–0.10(s, —$SiCH_3$, 27H), 0.86–0.92(m, —$CH_2$Si—, 6H), 1.13(t, J=7, —N—C—$CH_3$, 9H), 1.89–1.95(m, —C—$CH_2$—C—, 2H), 2.40–2.48(m, —C—$CH_2$—N—, 6H), 2.94–3.18(m, —OCON—$CH_2$—C—+—$CH_2$N$^+$—, 14H), 3.33(bs, —NH$^+$—+$H_2O$), 3.97–4.03(m, —NCOO—$CH_2$—, 6H), 4.38(bs, pyrrole N—$CH_2$—C—, 2H), 6.86(bs, —OCONH—, 2H), 7.03, 8.06(2s, pyrrole Ar—H, 2H); LRMS(FAB): 775 (M-$Et_3$N+H$^+$).

(10b) The procedure used for the synthesis of 10b was much the same as employed for 10a.

10b: 4 g, 92%; IR(KBr): $v_{N-H}$=3400–3700 cm$^{-1}$, $v_{N^+-H}$ =2600–2900 cm$^{-1}$, $v_{C=O}$=1680–1720 cm$^{-1}$, $v_{N-O}$=1260, 1520 cm$^{-1}$; $^1$H NMR(DMSO-$d_6$): δ–0.10(s, —$SiCH_3$, 27H), 0.84–0.92(m, —$CH_2$Si—, 6H), 1.14(t, J=7, —N—C—$CH_3$, 9H), 1.35–1.45(m, —C—$CH_2$—C—, 2H), 1.60–1.70(m, —C—$CH_2$—C—, 2H), 2.40–2.48(m, —C—$CH_2$—N—, 6H), 2.95–3.15(m, —OCON—$CH_2$—C—+—$CH_2$N$^+$—, 14H), 3.38(bs, —NH$^+$—+$H_2O$), 3.97–4.03(m, —NCOO—$CH_2$—C—, 6H), 4.43(t, J=7, pyrrole N—$CH_2$—C—, 2H), 6.86(bs, —OCONH—, 2H), 7.02, 8.03(2s, pyrrole Ar—H, 2H); LRMS(FAB): 789 (M-$Et_3$N+H$^{3O}$).

(12a) A solution of 11 (0.46 g, 1.8 mmol) in 100 mL MeOH was hydrogenated at atmospheric pressure over 10% palladium on charcoal (0.5 g) at room temperature. The catalyst was removed by filtration and the filtrate was concentrated. To the residue, 10a (1.6 g, 1.8 mmol) in dry DMF (100 mL) was added. After cooling to 0° C., DECP (0.33 g, 2.0 mmol) and $Et_3$N (1.0 g, 10 mmol) were added dropwise to the solution.

The solution was stirred at 0° C. for 2 h and at room temperature for another 10 h. Solvent was evaporated to dryness in vacuo, and the resulting residue was dissolved in 400 mL $CH_2Cl_2$. The organic phase was washed with 80mL 5% $Na_2CO_3$ aq. and dried over $K_2CO_3$. The crude product was purified with a flash column ($SiO_2$, EtOAc:MeOH:$Et_3N$=50:10:3) to give 12a as a yellow glassy solid.

12a: 1 g, 64%; TLC ($SiO_2$, EtOAc:MeOH:$Et_3N$= 50:10:3): $R_f$=0.59; $^1$H NMR (DMSO-$d_6$): δ–0.17(s, —$SiCH_3$, 27H), 0.84–0.92(m, —$CH_2$Si—, 6H), 1.55–1.62 (m, —CON—C—$CH_2$—C—, 2H), 1.92–2.00(m, —C—$CH_2$—C—, 2H), 2.12(s, —$NCH_3$, 6H), 2.23(t, J=7, —$CH_2$NMe, 2H), 2.43–2.48(m, —C—$CH_2$—N—, 6H), 2.95–3.02(m, Ar—CON—$CH_2$—C—, 2H), 3.12–3.23(m, —OCON—$CH_2$—C—, 8H), 3.79(s, pyrrole N—$CH_3$, 3H), 3.97–4.03(m, —NCOO—$CH_2$—C—, 6H), 4.40(bs, pyrrole N—$CH_2$—C—, 2H), 6.78(bs, —OCONH—, 2H), 6.79, 7.19, 7.59, 8.22(4s, pyrrole Ar—H, 4H); 8.04, 10.21(2bs, —CO—NH—, 2H); LRMS(FAB): 981 (M+H$^+$).

(12b) The procedure used for the synthesis of 12b was much the same as employed for 12a.

12b: 2.7 g, 60%; TLC ($SiO_2$, EtOAc:MeOH:$Et_3N$= 50:10:3): $R_f$=0.59; IR(KBr): $v_{N-H}$=3200–3600 cm$^{-1}$, $v_{C=O}$=1650–1720 cm$^{-1}$, $v_{N-O}$=1310, 1520 cm$^{-1}$; $^1$H NMR (DMSO-$d_6$): δ–0.17(s, —$SiCH_3$, 27H), 0.84–0.92(m, —$CH_2$Si—, 6H), 1.38–1.45(m, —C—$CH_2$—C—, 2H), 1.57–1.64(m, —CON—C—$CH_2$—C—, 2H), 1.65–1.73(m, —C—$CH_2$—C—, 2H), 2.14(s, —$NCH_3$, 6H), 2.24(t, J=7, —$CH_2$NMe, 2H), 2.43–2.47(m, —C—$CH_2$—N—, 6H), 2.96–3.00(m, Ar—CON—$CH_2$—C—, 2H), 3.10–3.20(m, —OCON—$CH_2$—C—, 8H), 3.79(s, pyrrole N—$CH_3$, 3H), 3.97–4.04(m, —NCOO—$CH_2$—C—, 6H), 4.42(t, J=7, pyrrole N—$CH_2$—C—, 2H), 6.79(bs, —OCONH—, 2H), 6.80, 7.19, 7.58, 8.19(4s, pyrrole Ar—H, 4H); 8.09, 10.20(2bs, —CO—NH—, 2H); LRMS(FAB): 995 (M+H$^+$).

(13a) A solution of 12a (1.0 g, 1.0 mmol) in 100 mL DMF was hydrogenated at atmospheric pressure over 10% palladium on charcoal (0.5 g) at 50° C. The catalyst was removed by filtration, the filtrate was concentrated, and the resulting residue was dissolved in dry DMF (100 mL). After cooling down to 0° C., 1-methyl-4-nitro-2-pyrrolecarbonyl chloride (0.2 g, 1.1 mmol) and $Et_3N$ (0.3 g, 3 mmol) were added. The solution was stirred at 0° C. for 2 h and at room temperature for another 10 h. The solution was concentrated to dryness in vacuo, and the resulting residue was dissolved in 300 mL $CH_2Cl_2$.

The organic phase was washed with 50 mL aqueous 5% $Na_2CO_3$ and dried over $K_2CO_3$. The crude product was purified with a flash column ($SiO_2$, EtOAc:MeOH:$Et_3N$= 50:10:5) to give 13a as a pale yellow glassy solid.

13a: 0.6 g, 54%; TLC ($SiO_2$, EtOAc:MeOH:$Et_3N$= 50:5:5): $R_f$=0.33; $^1H$ NMR (DMSO-$d_6$): δ–0.18(s, —SiCH$_3$, 27H), 0.84–0.91(m, —CH$_2$Si—, 6H), 1.56–1.63(m, —CON—C—CH$_2$—C—, 2H), 1.86–1.92(m, —C—CH$_2$— C—, 2H), 2.14(s, —NCH$_3$, 6H), 2.24(t, J=7, —CH$_2$NMe, 2H), 2.43–2.48(m, —C—CH$_2$—N—, 6H), 2.94–3.00(m, Ar—CON—CH$_2$—C—, 2H), 3.12–3.20(m, —OCON— CH$_2$—C—, 8H), 3.79, 3.95(2s, pyrrole N—CH$_3$, 6H), 3.97–4.04(m, —NCOO—CH$_2$—C—, 6H), 4.29(t, J=7, pyrrole N—CH$_2$—C—, 2H), 6.78(bs, —OCONH—, 2H), 6.80, 7.01, 7.19, 7.33, 7.59, 8.18(6s, pyrrole Ar—H, 6H); 8.05, 9.93, 10.28(3bs, —CO—NH—, 3H); LRMS(FAB): 1103 (M+H$^+$).

(13b) The procedure used for the synthesis of 13b was much the same as employed for 13a.

13b: 2 g, 66%; TLC ($SiO_2$, EtOAc:MeOH:$Et_3N$=50:5:5): $R_f$=0.33; IR(KBr): $v_{N-H}$=3100–3500 cm$^{-1}$, $v_{C=O}$= 1650–1720 cm$^{-1}$, $v_{N-O}$=1310, 1520 cm$^{-1}$; $^1H$ NMR (DMSO-$d_6$): δ–0.16(s, —SiCH$_3$, 27H), 0.85–0.94(m, —CH$_2$Si—, 6H), 1.38–1.43(m, —C—CH$_2$—C—, 2H), 1.58–1.63(m, —CON—C—CH$_2$—C—, 2H), 1.60–1.65(m, —C—CH$_2$—C—, 2H), 2.13(s, —NCH$_3$, 6H), 2.24(t, J=7, —CH$_2$NMe, 2H), 2.43–2.48(m, —C—CH$_2$—N—, 6H), 2.95–3.02(m, Ar—CON—CH$_2$—C—, 2H), 3.12–3.20(m, —OCON—CH$_2$—C—, 8H), 3.79, 3.95(2s, pyrrole N—CH$_3$, 6H), 3.97–4.05(m, —NCOO—CH$_2$—C—, 6H), 4.31(t, J=7, pyrrole N—CH$_2$—C—, 2H), 6.78(bs, —OCONH—, 2H), 6.81, 7.00, 7.18, 7.32, 7.58, 8.18(6s, pyrrole Ar—H, 6H); 8.06, 9.92, 10.28(3bs, —CO—NH—, 3H); LRMS(FAB): 1117 (M+H$^+$).

(14a) A solution of 13a (0.6 g, 0.6 mmol) in 100 mL DMF was hydrogenated at atmospheric pressure over 10% palladium on charcoal (0.5 g) at 60° C. The catalyst was removed by filtration, the filtrate was concentrated, and the resulting residue were dissolved in dry DMF (100 mL). After cooling down to 0° C., $CH_3COCl$ (0.08 g, 1.0 mmol) and $Et_3N$ (0.3 g, 3.0 mmol) were added dropwise.

The solution was stirred at 0° C. for 2 h and at room temperature for another 10 h. The solution was concentrated to dryness in vacuo, and the resulting residue was dissolved in 300 mL $CH_2Cl_2$. The organic phase was washed with 50 mL aqueous 5% $Na_2CO_3$ and dried over $K_2CO_3$. The crude product was purified with a flash column ($SiO_2$, EtOAc:MeOH:$Et_3N$=50:20:5) to give 14a as a pale yellow glassy solid.

14a: 0.3 g, 45%; TLC ($SiO_2$, EtOAc:MeOH:$Et_3N$= 50:20:5): $R_f$=0.27; $^1H$ NMR (DMSO-$d_6$): δ–0.15(s, —SiCH$_3$, 27H), 0.86–0.90(m, —CH$_2$Si—, 6H), 1.58–1.63 (m, —CON—C—CH$_2$—C—, 2H), 1.86–1.92(m, —C—CH$_2$—C—, 2H), 1.96(s, CH$_3$CON—, 3H), 2.17(s, —NCH$_3$, 6H), 2.28(t, J=7, —CH$_2$NMe, 2H), 2.43–2.48(m, —C—CH$_2$—N—, 6H), 2.94–3.00(m, Ar—CON—CH$_2$— C—, 2H), 3.15–3.22(m, —OCON—CH$_2$—C—, 8H), 3.79, 3.82(2s, pyrrole N—CH$_3$, 6H), 3.98–4.06(m, —NCOO— CH$_2$—C—, 6H), 4.27(t, J=7, pyrrole N—CH$_2$—C—, 2H), 6.79(bs, —OCONH—, 2H), 6.81, 6.86, 7.02, 7.14, 7.18, 7.31(6s, pyrrole Ar—H, 6H); 8.06, 9.82, 9.88, 9.90(4bs, —CO—NH—, 4H); LRMS(FAB): 1115 (M+H$^+$).

(14b) The procedure used for the synthesis of 14b was much the same as employed for 14a.

14b: 1.5 g, 74%; TLC ($SiO_2$, EtOAc:MeOH:$Et_3N$= 50:20:5): $R_f$=0.27; $^1H$ NMR (DMSO-$d_6$): δ–0.13(s, —SiCH$_3$, 27H), 0.86–0.90(m, —CH$_2$Si—, 6H), 1.40–1.48 (m, —C—CH$_2$—C—, 2H), 1.58–1.65(m, —C—CH$_2$—C— +—CON—C—CH$_2$—C—, 4H), 1.96(s, CH$_3$CON—, 3H), 2.16(s, —NCH$_3$, 6H), 2.27(t, J=7, —CH$_2$NMe, 2H), 2.43–2.48(m, —C—CH$_2$—N—, 6H), 2.96–3.00(m, Ar—CON—CH$_2$—C—, 2H), 3.11–3.22(m, —OCON— CH$_2$—C—, 8H), 3.79, 3.82(2s, pyrrole N—CH$_3$, 6H), 3.98–4.06(m, —NCOO—CH$_2$—C—, 6H), 4.29(t, J=7, pyrrole N—CH$_2$—C—, 2H), 6.79(bs, —OCONH—, 2H), 6.81, 6.85, 7.00, 7.13, 7.17, 7.28(6s, pyrrole Ar—H, 6H); 8.05, 9.79, 9.86, 9.88(4bs, —CO—NH—, 4H); LRMS(FAB): 1129 (M+H$^+$).

(6a) Ten mL of $CF_3COOH$ was cooled in an ice-bath before slowly being added to a solution of 14a (0.18 g, 0.15 mmol) in 10 mL $CH_2Cl_2$ with stirring at 0° C. The solution was stirred at 0° C. for 2 h and at room temperature for another 2 h. $CF_3COOH$ and $CH_2Cl_2$ was removed by evaporation and the resulting residue was dissolved in 50 mL MeOH. After addition of 20 g ion-exchange resin (HO$^-$ form) the mixture was stirred for 30 min at room temperature. The resin was removed by filtration and the filtrate was concentrated under vacuum to give pure 6a as a pale yellow glassy solid.

6a: 0.1 g, 98%; $^1H$ NMR (DMSO-$d_6$): δ1.58–1.63(m, —CON—C—CH$_2$—C—, 2H), 1.78–1.82(m, —C—CH$_2$— C—, 2H), 1.96(s, CH$_3$CON—, 3H), 2.12(s, —NCH$_3$, 6H), 2.23(t, J=7, —CH$_2$NMe, 2H), 2.34(t, J=7, —C—CH$_2$—N, 4H), 2.42–2.46(m, —C—CH$_2$—N—, 6H), 2.54–2.64(m, —C—CH$_2$—N—, 6H), 3.16–3.20(m, Ar—CON—CH$_2$— C—, 2H), 3.25(bs, —C—NH$_2$+H$_2$O), 3.79, 3.82(2s, pyrrole N—CH$_3$, 6H), 4.32(t, J=7, pyrrole N—CH$_2$—C—, 2H), 6.82, 6.85, 7.00, 7.14, 7.17, 7.27(6s, pyrrole Ar—H, 6H); 8.11(t, J=5.5, Ar—CO—NH—C—, 1H), 9.80(s, —CO— NH—, 1H), 9.90(bs, —CO—NH—, 2H); LRMS(FAB): 683 (M+H$^+$); HRMS(FAB): 683.4467 (calculated for $C_{33}H_{55}N_{12}O_4$(M+H$^+$) 683.4469).

(6b) The procedure used for the synthesis of 6b was much the same as employed for 6a.

6b: 0.65 g, 96%; $^1H$ NMR (DMSO-$d_6$): δ1.33–1.40(m, —C—CH$_2$—C—, 2H), 1.56–1.64(m, —CON—C—CH$_2$— C—, 2H), 1.64–1.71(m, —C—CH$_2$—C—, 2H), 1.96(s, CH$_3$CON—, 3H), 2.13(s, —NCH$_3$, 6H), 2.23(t, J=7, —CH$_2$NMe, 2H), 2.38(t, J=7, —C—CH$_2$—N, 4H), 2.42–2.46(m, —C—CH$_2$—N—, 6H), 2.54–2.64(m, —C—CH$_2$—N—, 6H), 3.15–3.20(m, Ar—CON—CH$_2$— C—, 2H), 3.22(bs, —C—NH$_2$+H$_2$O), 3.79, 3.82(2s, pyrrole N—CH$_3$, 6H), 4.28(t, J=7, pyrrole N—CH$_2$—C—, 2H), 6.81, 6.86, 7.00, 7.14, 7.17, 7.28(6s, pyrrole Ar—H, 6H); 8.08(t, J=5.5, Ar—CO—NH—C—, 1H), 9.82, 9.89, 9.92 (3s, —CO—NH—, 3H); LRMS(FAB): 697 (M+H$^+$); HRMS (FAB): 697.4631 (calcd for $C_{34}H_{57}N_{12}O_4$(M+H$^+$) 697.4625).

Discussion

Synthesis

Our synthesis of 6a,b (FIG. 15) began with the preparation of the central pyrrole units (8a,b) (FIG. 16) in which the tren group was attached to the pyrrole through the desired linker arms. Attempts at purification of 8a,b through column chromatography failed.

Very poor separation was obtained over an $Al_2O_3$ column. In addition, use of a $SiO_2$ column led to the hydrolysis of the ester group in 8.

Compound 8 (5%) was obtained only as a mixture of the methyl ester (5%) and the carboxylate (20%) with $SiO_2$ column chromatography by elution with MeOH:conc. $NH_3$ (aq.)=80:20. It seems that the polyamino group can complex trace amounts of metal ion from the $SiO_2$ which consequently catalyzes the hydrolysis of the ester group. Due to these complexities in attempted purification, crude 8, which by $^1$H NMR showed only ~5% impurity, was used in the next reaction without purification.

Attempts to employ t-butyl S-4,6-dimethylpyrimid-2-yl thiocarbonate as an agent to deliver the t-butyl carbamate (Nagasawa, T.; Kuroiwa, K.; Narita, K.; Isowa, Y. *Bull. Chem. Soc. Jpn.* 1973, 46, 1269) (Boc) as a protecting group for the primary and secondary amines of 8 provided but ~30% yields of product. Changing the synthetic methodology by using 2-trimethylsilylethyl carbamate ((a) Carpino, L. A.; Tsao, J.-H. *J. Chem. Soc., Chem. Commun.* 1978, 358; (b) Rosowsky, A.; Wright, J. E. *J. Org. Chem.* 1989, 54, 5551) (Teoc) for the protection of the tren polyamino group on 8 provided 9 in a 52–61% yield after separation by $SiO_2$ column chromatography (FIG. 16).

Additional factors in favor of the choice of this protecting group included its stability toward the conditions of hydrogenation over Pd/C and other harsh conditions employed in the synthetic steps, including the last step of the synthesis.

Compound 6, like 8, was difficult to purify since it did not migrate on $SiO_2$ TLC even with the elution solvent mixture of MeOH:conc. $NH_3$ (aq.)=60:40. Fortunately, the deprotection reaction of 14 (acid catalyzed removal of the Teoc group with $CF_3COOH$) produces only the desired product (6) and volatile compounds ((a) Carpino, et al., 1978, supra). Subsequent treatment of the crude 14 product with $HO^-$ exchange resin gave very pure 6 as shown by $^1$H NMR. DNase I footprint analysis of 6a and 6b.

DNase I was employed as the DNA cleaving agent for footprint generation (Galas, D. J.; Schmitz, A. *Nucleic Acids Res.* 1978, 5, 3157) in the comparative analysis of the interactions of 6a, 6b, and distamycin with the 167 bp EcoRI/Rsa I pBR322 restriction fragment.

Four A+T-rich distamycin (Harshman, K. D.; Dervan, P. B. *Nucleic Acids Res.* 1985, 13, 4825), bromoacetyldistamycin (Baker, B. F.; Dervan, P. B. *J. Am. Chem. Soc.* 1989, 111, 2700), and dien-microgonotropen (He, G.-X., 1993, supra) binding sites have been previously identified (bold typeface, FIG. 1), making this an ideal DNA fragment for the comparative study of the tren-microgonotropens with distamycin.

DNase I has an advantage over Tullius' HO. (Burkhoff, A. M., Tullius, T. D. *Cell,* 1987, 48, 935) and Dervan's MPE.Fe (II) (Van Dyke, M. W.; Hertzberg, R. P.; Dervan, P. B. *Proc. Natl. Acad. Sci. USA* 1982, 79, 5470) in that it cleaves precisely at the 5' edge of an agent's minor groove binding site, producing a protected region with a sharp, well-defined 5' border ((a) Dabrowiak, J. C.; Goodisman, J. *In Chemistry & Physics of DNA-Ligand Interactions*; Kallenbach, N. R., Ed.; Adenine Press: New York, 1989; pp 143–174; (b) Goodisman, J.; Dabrowiak, J. C. *Biochemistry* 1992, 31, 1058).

Thus, even though DNase I cleavage at the 3' edge of the binding site is not precisely defined, complementary strand analysis provides sharply defined 5' borders on both DNA strands (FIG. 1), and, hence, precisely defined binding sites that correspond closely to those previously defined (He, et al., 1993, supra).

Figure 2A:
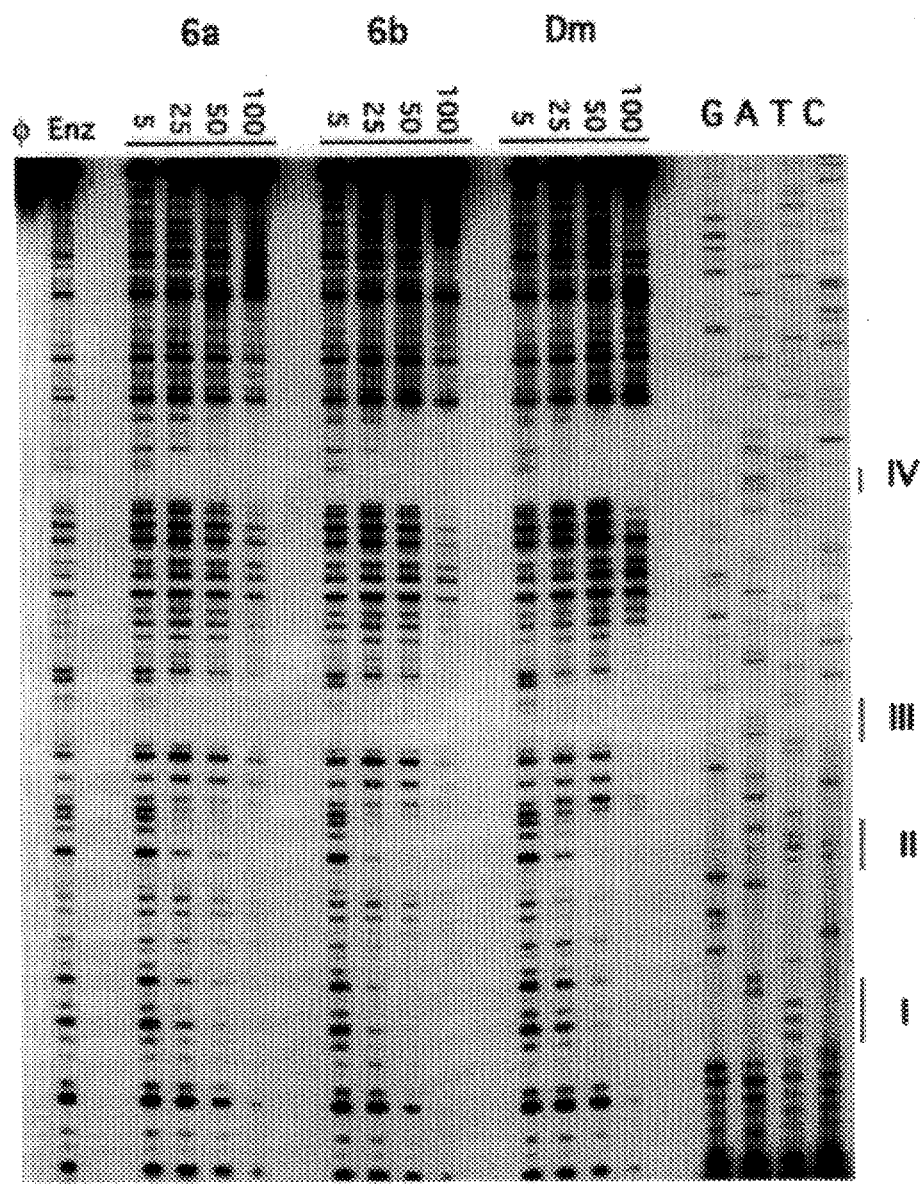
FIGS. 2a/b. DNase I footprint analysis of the binding of the tren-microgonotropens and distamycin (Dm) to (a) the 5'-labeled 167 bp EcoRI/RsaI restriction fragment and (b) the 3'-labeled 167 bp EcoRI/RsaI restriction fragment. In lane 1, the greek letter phi indicates intact DNA; lane 2, Enz is the abbreviation for DNase I cleavage of unprotected DNA; lanes 3 to 14, DNase I footprinting reactions containing 6a (FIG. 15), 6b (FIG. 15), and Dm, respectively, are at the concentrations indicated in µM. Products of the four dideoxynucleotide sequencing reactions (GATC) were synthesized by extension of the 5'-labeled oligonucleotide primer depicted in FIG. 1. The same sequencing reactions were used for the 3' sequence ladder by exchanging the complementary base pairs (G with C; C with G; A with T; T with A. The four A+T-rich binding sites depicted in FIG. 1 are indicated adjacent to the DNA sequence ladder.
Figure 2B:
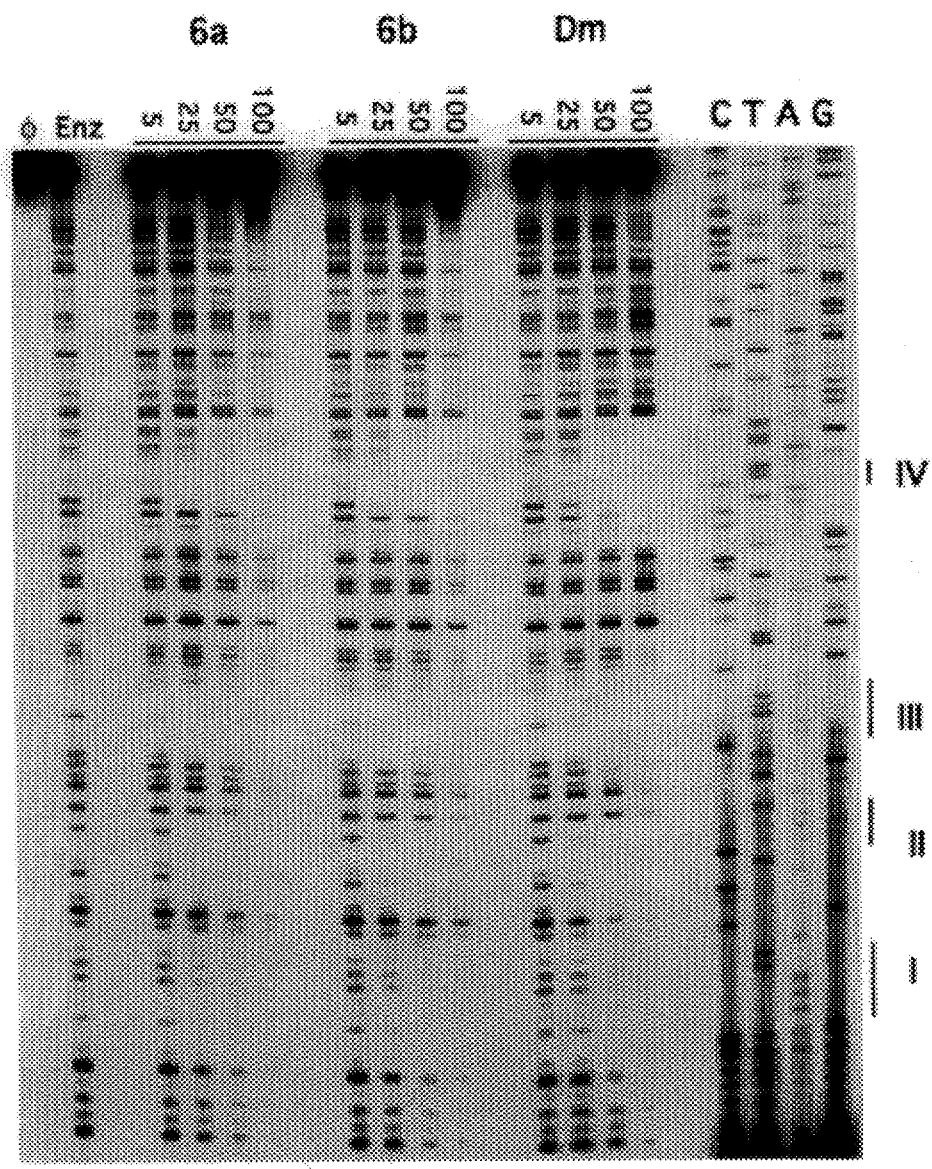

DNase I footprinting analysis of the 3'-[$^{32}$P] labeled 167 bp EcoRI/RsaI restriction fragment with 6a and 6b (FIG. 2b), when coupled with results from the 5'-labeled material (FIG. 2a), defined binding sites similar to those for distamycin. Pre-incubation of the 167 bp 3'- and 5'-[$^{32}$P] labeled restriction fragments with 5 μM 6a, 6b, or distamycin (0.05 ligand/bp DNA) did not produce detectable inhibition of DNase I cleavage at any of the four A+T-rich binding sites (FIGS. 2a/b).

In contrast, specific inhibition of cleavage was observed at three of the four sites (FIG. 1 at sites II, III, IV) after pre-incubation with 25 and 50 μM 6a, 6b, or distamycin (0.25 and 0.5 ligand/bp DNA). Site I could only be distinguished at 100 μM, and even then, site definition was vague.

Pre-incubation of the restriction fragment with 100 μM ligand (1.0 ligand/bp DNA) resulted in additional protection from DNase I cleavage within the spacer regions which flank the A+T-rich binding sites. Dervan and co-workers have observed a similar binding isotherm for distamycin on the 516 bp RsaI/EcoRI restriction fragment of pBR332 (Van Dyke et al., 1982, supra). At higher concentrations of distamycin (3.1 ligand/bp DNA), spacer regions which flanked A+T-rich binding sites coalesced into a single, broad, protected zone (Van Dyke, et al., 1982, supra).

Analysis of the 5' footprint edges of the binding sites of 50 μM 6a, 6b, and distamycin shows cleavage patterns that are very similar to those seen previously for the dien-microgonotropens (He, et al., 1993, supra). Closer scrutiny reveals small changes for sites II and III while site IV is unchanged. Site III is one base smaller on the 3' strand and site II is two bases smaller on the 3' strand than was found for the dien-microgonotropens (He, et al., 1993, supra) (FIG. 1).

Even at the highest concentrations of 6a and 6b, enhancements in or increased rates of DNase I cleavage were not observed at specific sequences for the 5'- and the 3'-[$^{32}$P] labeled restriction fragments (Dm showed enhancements similar to those found previously) (He, et al., 1993, supra).

Equilibrium constants for the association of 6a and 6b with oligomeric DNA were assessed by the complexing of tren-microgonotropen-a and -b to the hexadecamer d(GGCGCAAATTTGGCGG)(SEQ ID NO:1)/d(CCGCCAAATTTGCGCC)(SEQ ID NO:2) in aqueous solutions at 35° C. (2.8 mL solutions containing 0.01M phosphate buffer, pH 7.0, and 0.01M NaCl).

These reactions were followed by the competition of the dye Hoechst 33258 (Ht) with 6a and 6b for the $A_3T_3$ minor groove binding site (an extension of Ht alone binding to dsDNA). The concentrations of 6a and 6b were confirmed by $^1$H NMR peak integration of resonances with those of an equivalent concentration of mesitoate.

As shown previously (Browne, K. A.; He, G.-X.; Bruice, T. C. *J. Am. Chem. Soc.* 1993, 115, 7072), monitoring the increase in fluorescence intensity as the association of Ht with the hexadecamer displaces prebound nonfluorescent ligands is an excellent method for determining equilibrium binding constants. FIG. 17 relates the equilibrium constants for the complexing of one and two Ht species to the hexadecamer with one and two L (where L=6a or 6b) binding to the hexadecamer, plus equilibrium constants for the simultaneous binding of one Ht and one L at the same site.

$$F = \frac{\Sigma \phi K_{Ht1}[Ht](0.5 + K_{Ht2}[Ht] + 0.5 K_{Ht_L}[L]Q^L)}{1 + K_{Ht1}[Ht] + K_{Ht1}K_{Ht2}[Ht]^2 + K_{Ht1}K_{Ht_L}[Ht][L] + K_{L1}L] + K_{L1}K_{L2}L]^2} \quad (1)$$

Eq 1, derived from FIG. 17, relates each of the equilibrium binding constants, the total fluorescence (Σθ), and [L] in terms of fluorescence (F) and [Ht]. The rationale behind FIG. 17 and the subsequent derivation of eq 1 have been described in considerable detail (Browne, et al., 1993, supra). The values of log $K_{Ht1}$=7.6 and log $K_{Ht2}$=9.1 used were determined from a reevaluation of data previously collected (Browne, et al., 1993, supra) and are very close to the previously determined values. A concentration independent static quenching term, Q', is included in eq 1 to account for the lessened fluorescent emission of the DNA:Ht:L complex compared to the DNA:Ht and DNA:Ht$_2$ complexes.

Figure 3A:
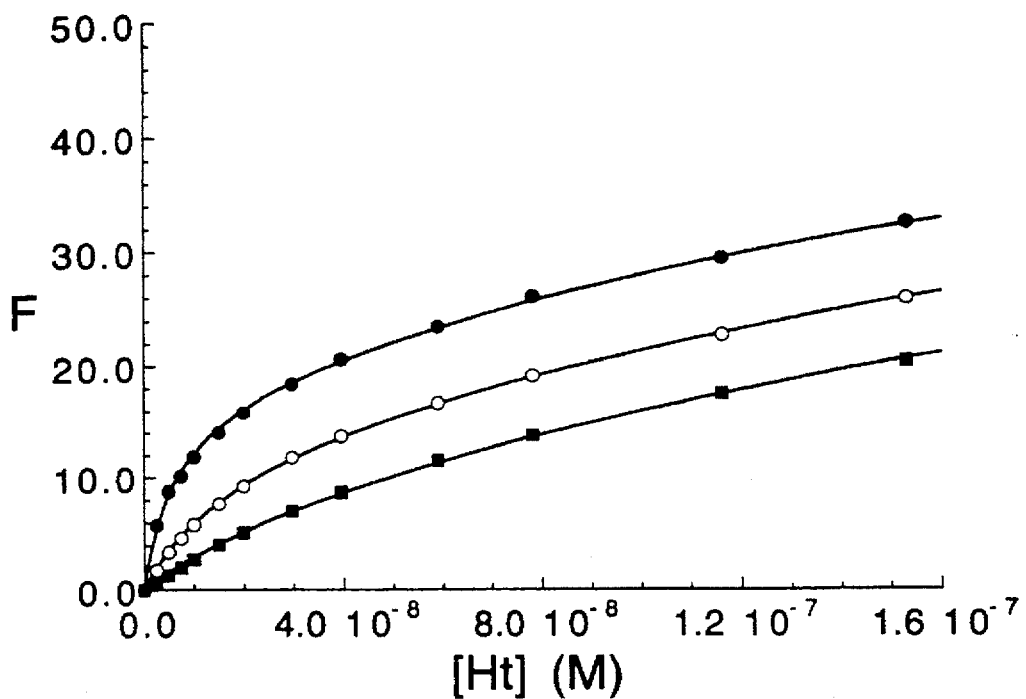
FIGS. 3a/b. Plot of fluorescence (F, in arbitrary units) vs. Hoechst 33258 (Ht) concentration at pH 7.0 and 35° C. for (a) 6a and (b) 6b at $8.0 \times 10^{-9}$M (____closed circle____), $1.0 \times 10^{-8}$M (____open circle____), and $1.2 \times 10^{-8}$M (____closed square____) in the presence of $5.0 \times 10^{-9}$M hexadecamer duplex. The theoretical curves which fit the points were computer generated by use of eq 1.
Figure 3B:
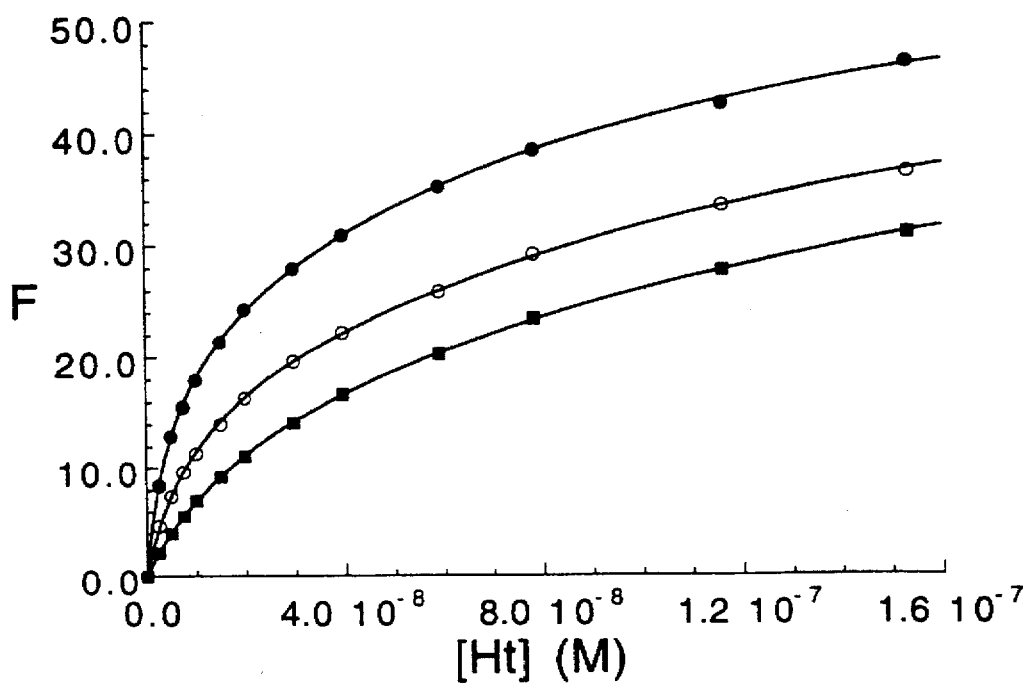

The equilibrium association constants calculated as best fits to the experimental data points for 6a and 6b with eq 1 are presented in Table I. Plots of F vs. [Ht] using these constants at $8.0 \times 10^{-9}$, $1.0 \times 10^{-8}$, and $1.2 \times 10^{-8}$ M ligand and $5.0 \times 10^{-9}$ M in hexadecamer duplex are shown in FIGS. 3a and 3b.

Inspection of Table I shows that the values of $K_{L1}$ ($1.6 \times 10^9$ and $7.9 \times 10^8 M^{-1}$ for 6a and 6b, respectively) and $K_{L2}$ ($1.6 \times 10^9$ and $1.0 \times 10^9 M^{-1}$ for 6a and 6b, respectively) have only a small, if any, cooperative effect for the binding of the tren-microgonotropens to d(GGCGCAAATTTGGCGG)(SEQ ID NO:1)/d(CCGCCAAATTTGCGCC)(SEQ ID NO:2).

A reevaluation of the previously studied dien-microgonotropens (5a,b,c) (Browne, et al., 1993, supra) indicates that the second association constants are more than 3-fold greater than the first (Table I). The complex association constants ($K_{L1}K_{L2}$) are greater for 6a,b than for 5a,b,c since both $K_{L1}$ and $K_{L2}$ are slightly greater for the tren- than for the dien-microgonotropens. This is as expected since there are 4 amines (including 2 primary amines) in the tren moiety verses 3 tertiary amines in the dien group. Primary amines have a higher p$K_a$ than tertiary amines (Perrin, D. D. "Dissociation Constants of Organic Bases in Aqueous Solution"; Butterworths: London, 1965) and are more prone to hydrogen bond to phosphate linkages.

In addition, there is little difference in the association constants of the different microgonotropens within a given series (tren- or dien-) even though the chain lengths of the linkers differ. This is likely due to the fact that binding ability is a function of both the minor groove binder and the polyamine, with all chain lengths being long enough to permit efficient electrostatic grasping of the phosphodiester backbone.

The degree of fluorescence quenching of Ht in the DNA:Ht:L complexes when L=6a and 6b was also found to be different than for the dien-microgonotropens while the mode of quenching (intracomplex) was the same for both sets of microgonotropens. From values of Q'=0.41 and 0.64 for 6a and 6b, respectively, quenching of Ht fluorescence was determined to be 59% and 36%.

In contrast, all three of the dien-microgonotropens quenched fluorescence to a constant degree (~45%). A small difference in the quenching terms within a given series (tren- or dien-) would be expected since a given series has a common polyamine. But, in fact, the fluorescence quenching that 6a causes is considerably more efficient than that due to any of the other microgonotropens. This difference in quenching is likely because of a special position that the 3 methylene linker of 6a confers upon its tren moiety such that the quenching amino groups are in greater intimate contact with the Ht fluorochrome than is the case with 5a,b,c or 6b.

The fluorescence of solutions containing (i) the hexadecameric DNA duplex plus Ht in the ratio of 1:2 or (ii) the hexadecameric DNA duplex, Ht, and 6b in the ratio of 1:1:1 did not change on titration with a solution of tris(2-aminoethyl)amine. Thus, as for the dien-microgonotropens (Browne, et al., 1993, supra) amine quenching is not bimolecular but, rather, to intracomplex quenching within the DNA:Ht:L complex.

TABLE I

Mean values of the association and quenching constants for Ht, Dm, 2, 5a, 5c, and the new ligands 6a and 6b to d(GGCGCAAATTTGGCGG)(SEQ ID NO: 1) /d(CCGCCAAATTTGCGCC) (SEQ ID NO: 2) {in H$_2$O, 10 mM phosphate buffer, pH 7.0; and 10 mM NaCl at 35° C}.

| Ligand | log $K_{L1}$ | log $K_{L2}$ | log $K_{L1}K_{L2}$ | log $K_{HtL}$ | log $K_{LHt}$ | Q' |
|---|---|---|---|---|---|---|
| Ht[a,b] | 7.6 ± 0.1 | 9.1 ± 0.2 | | | | |
| Dm[a,c] | 7.6 ± 0.09 | 8.4 ± 0.08 | 16.0 | 8.8 ± 0.09 | 8.8 | |
| 2[a,d] | 6.8 ± 0.1 | 6.2 ± 0.5 | 13.0 | −1.2 ± 0.1 | −1.3 | |
| 5a[a,c] | 8.5 ± 0.3 | 8.9 ± 0.02 | 17.4 | 10.0 ± 0.07 | 8.9 | 0.53 ± 0.2 |
| 5b[a,c] | 8.3 ± 0.2 | 8.8 ± 0.2 | 17.1 | 10.0 ± 0.06 | 9.2 | 0.57 ± 0.064 |
| 5c[a,c] | 8.2 ± 0.2 | 8.8 ± 0.05 | 17.0 | 9.9 ± 0.02 | 9.2 | 0.55 ± 0.081 |
| 6a[e] | 9.2 ± 0.1 | 9.2 ± 0.1 | 18.4 | 10.7 ± 0.01 | 8.8 | 0.41 ± 0.11 |
| 6b[e] | 8.9 ± 0.08 | 9.0 ± 0.2 | 17.9 | 10.3 ± 0.1 | 8.8 | 0.64 ± 0.046 |

[a]A recalculation of previously determined association constants with the curve fitting program SigmaPlote ® (Jandel Scientific). [b]The constants were calculated from the mean values of 3 titration experiments of the hexadecamer with Ht. [c]The standard deviations are $\sigma_n$, are from the mean values of the constants calculated at $8.0 \times 10^{-9}$, $1.0 \times 10^{-8}$, $1.2 \times 10^{-8}$, and $1.4 \times 10^{-8}$ M ligand. [d]The standard deviations, $\sigma_n$, are from the mean values of the constants calculated at $5.0 \times 10^{-8}$ and $1.0 \times 10^{-7}$ M 2. [e]The standard deviations, $\sigma_n$, are from the mean values of the constants from 2 experiments calculated at $8.0 \times 10^{-9}$, $1.0 \times 10^{-8}$, and $1.2 \times 10^{-8}$ M in 6a or 6b.

Figure 4:
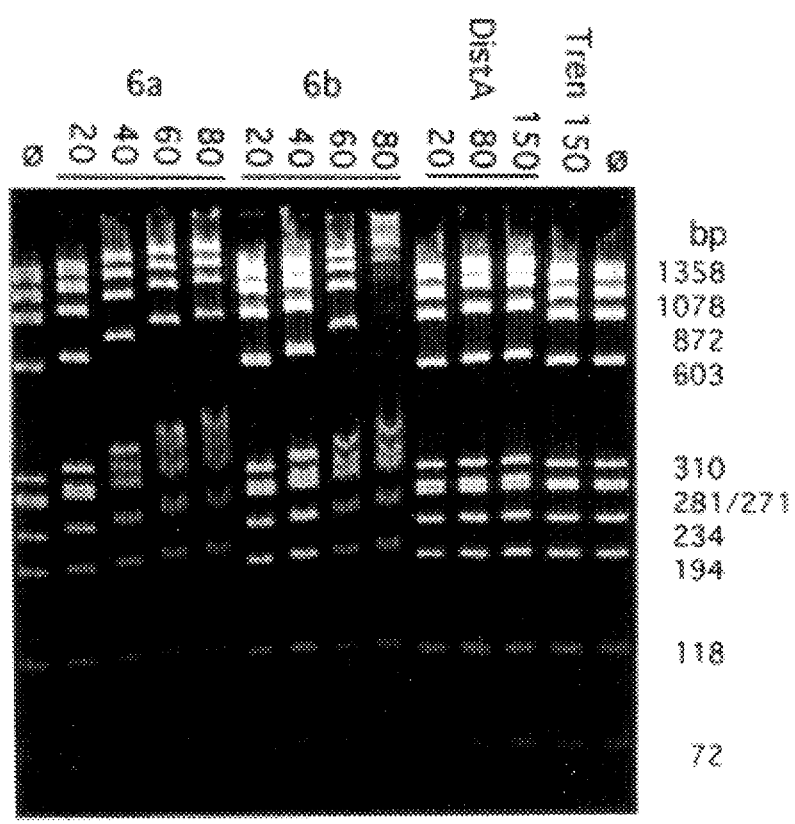
FIG. 4. A gel showing the effect of DNA binding on the electrophoretic mobility of φ-174-RF DNA HaeIII restriction digest fragments (sizes indicated to the right side of the figure). In lanes 1 and 14, the greek letter phi indicates control DNA; lanes 2 through 13, the indicated concentrations of 6a, 6b, distamycin (Dm), and tris(2-aminoethyl) amine (Tren) are in µM.
Figure 5A:
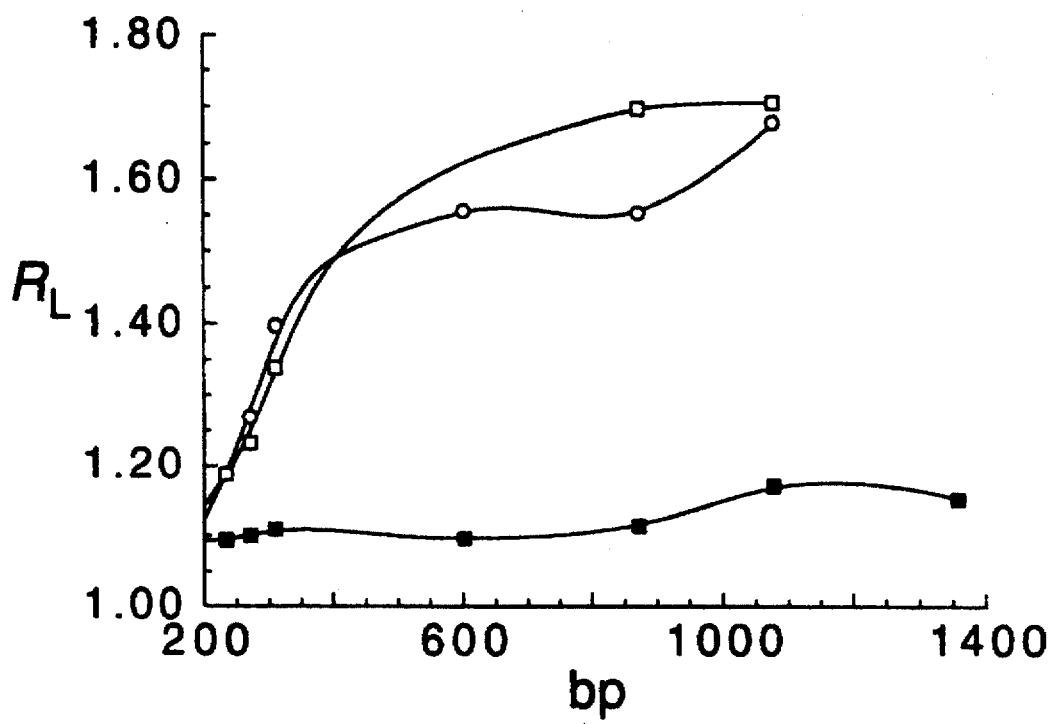
FIGS. 5a/b. (a) A plot of the ratio of apparent DNA length to real length ($R_L$) vs. the number of base pairs (bp) in the longest and intermediate sized DNA fragments in the presence of 80 µM 6a (____open circle____) or 6b (____open square____), and 150 µM distamycin (____closed square____).

Electrophoretic mobility shift assay for 6a and 6b. The effect of the binding of 6a and 6b to DNA on the electrophoretic migration has been investigated with φX-174-RF DNA HaeIII restriction digest fragments (FIG. 4). Our use of φX-174-RF DNA restriction digests in electrophoretic mobility shift assays (He, et al., 1993, supra) is predicated on the common use of this material as molecular weight size standards.

Applicants have calculated (He, et al., 1993, supra) 246 A-tracts (AAAA, AAAT, or TAAA; independent or overlapping) approximately evenly spaced throughout the restriction digest fragments. These are the most preferred binding sites for 6a and 6b (loc. cit.).

When increasing the concentrations of 6a and 6b from 20 to 40, 60, and 80 μM (0.088 to 0.176, 0.264, and 0.352 ligand/bp, respectively), the mobility of DNA restriction fragments decreases. Moreover, the decreases in the otherwise approximately logarithmic mobility of the DNA fragments are proportional to their lengths (largest effect seen with the largest fragments). This suggests that the conformation of the DNA is altered significantly by the binding of the tren-microgonotropens, especially in the largest fragments (1358, 1078, and 872 bp).

An alternative explanation of the decreased mobility that must be considered is a change in the charge to mass ratio of the DNA:ligand complex. This is unlikely, however, since the shortest fragments do not show the greatest change in mobility as dictated by the logarithmic nature of DNA fragments in an electric field on an agarose gel.

Meanwhile, a "smearing" of the bands is evident in the intermediate fragments (603, 310, 281/271, 234, and 194 bp), especially at 60 and 80 μM tren-microgonotropen. This indicates not simply a conformational change but a population of differing conformations of DNA:tren-microgonotropen complexes leading to a distribution of apparent electrophoretic molecular weights.

Distamycin brings about smaller changes at 150 μM (0.66 ligand/bp) than 6a or 6b at 40 μM. Tris(2-amino-ethyl)amine, the tren moiety of the tren-microgonotropens, produces no apparent change in electrophoretic behavior at 150 μM compared with the control lanes.

To gain a more quantitative appreciation for the magnitude of the DNA structural changes occurring with the association of the tren-microgonotropens, the migration data has been reduced to a graphical form.

The electrophoretic mobilities of the φX-174-RF DNA HaeIII restriction digest fragments have been calculated as the $R_L$ values when coelectrophoresed with 6a, 6b, Dm, and tris(2-aminoethyl)amine.

$R_L$ is the ratio of the apparent length to real length where apparent length is the length of uncomplexed dsDNA (interpolated or slightly extrapolated from the standards) with same mobility (Wu, H.-M.; Crothers, D. M. *Nature* 1984, 308, 509).

The representative plot of $R_L$ vs. bp at 80 μM 6a and 6b, or 150 μM distamycin (FIG. 5a) shows that as the size of the fragment increases, the effect of these agents is to increase the apparent size of DNA fragments (decrease the mobility) relative to the control (φX-174-RF DNA with no added agent).

The order of effectiveness in increasing the apparent length of φX-174-RF DNA HaeIII restriction digest fragments is 6a~6b>>distamycin>tren. The $R_L$ value does not vary as a simple function with increasing DNA fragment size. Instead, variation in migration patterns is probably contingent on the number of A+T-rich sequences in each fragment, the relative positions of the A+T-rich sequences within a given fragment (Levene, S. D.; Wu, H.-W.; Crothers, D. M. *Biochemistry* 1986, 25, 3988), and the porosity of the gel (Thompson, J. F.; Landy, A. *Nucleic Acids Res.* 1988, 16, 9687).

Figure 5B:
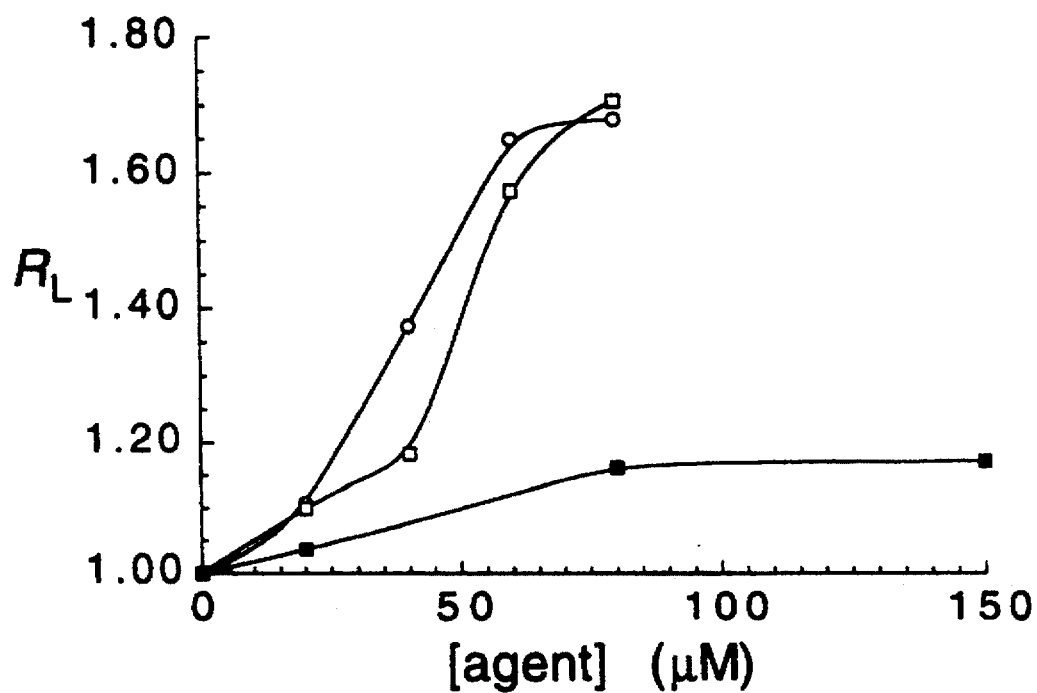

In addition, the plot of $R_L$ vs. agent for the 1078 bp fragment in FIG. 5b shows that tren-microgonotropen-a and -b's influence on the DNA conformation is quite concentration dependent and sigmoidal in response.

Distamycin does not demonstrate very marked changes even at the highest concentrations examined. In fact, the effect of distamycin on these fragments is nearly concentration independent over the concentration ranges examined.

As is evident from the above discussion and previous work from this laboratory (He, et al., 1993, supra), the tren-microgonotropens are about twice as effective in inducing structural changes in DNA as are the dien-microgonotropens (nearly the same decrease in electrophoretic mobility is seen for 6a,b at ca. half of the concentration that was used for 5a,b,c) and at least four times as effective in inducing structural changes as is Dm.

The fact that the tren-microgonotropens are only approximately twice as effective as the dien-microgonotropens in retarding gel electrophoretic migration of DNA fragments is somewhat surprising considering the fact that the complex equilibrium association constants ($K_{L1}K_{L2}$, Table I) for 6a (i.e., $2\times10^{18}M^{-2}$) and 6b (i.e., $8\times10^{17}M^{-2}$) are considerably higher than those of the dien-microgonotropens (i.e., $1\times10^{17}$ to $2\times10^{17}M^{-2}$).

This suggests that the mode of inhibition of DNA mobility in an electrophoretic field is not simply a function of how tight the ligand binds to the DNA. Instead, the degree of inhibition is likely due to a less well understood quality of the microgonotropen which induces a DNA conformational change upon association.

Topoisomerase I inhibition by 6b

Mammalian topoisomerase I (topoI) is an enzyme that relaxes both positive and negative superhelical turns in covalently closed circular DNA. It performs this ATP-independent reaction by transiently breaking the phosphodiester linkage of one strand of DNA, passing the intact strand through the break, and then religating the gap. In this manner, the enzyme effectively decreases the superhelical density by changing the linking number of the closed circular DNA by integral values (Lewin, B. *Genes*, 2nd Edition, John Wiley & Sons, New York, 1985).

Inhibition of topoI's action on supercoiled pBR322 by 6b was compared to inhibition by Dm and 5b (dien-microgonotropen-b). In the first set of experiments, each agent was allowed to incubate with the DNA for 1 hr prior to the 18 hr topoI reaction period. The topoI (+) control (Enz, 18h) shows the extent of superhelical relaxation found in the absence of added 5b, 6b, or Dm while the (−) control (φ) shows the spontaneous background relaxation.

The amount of relaxation seen in the (+) control is roughly the same amount seen in the presence of 150 μM 5b (4.95 molecules of 5b/bp). With 150 μM Dm, a continuous family of topological isomers separated by single linking numbers is generated from supercoiled to completely relaxed circular pBR322 indicating partial inhibition (the number of topological isomers is somewhere between the (+) and the (−) controls). At 10 μM 6b (0.33 molecules of 6b/bp) a considerable number of the same topological isomers as for Dm at 150 μM can be seen even though the predominant isomer is the fully supercoiled species. By 30 μM 6b (0.99 molecules of 6b/bp), complete inhibition of topoI takes place.

Figure 6:
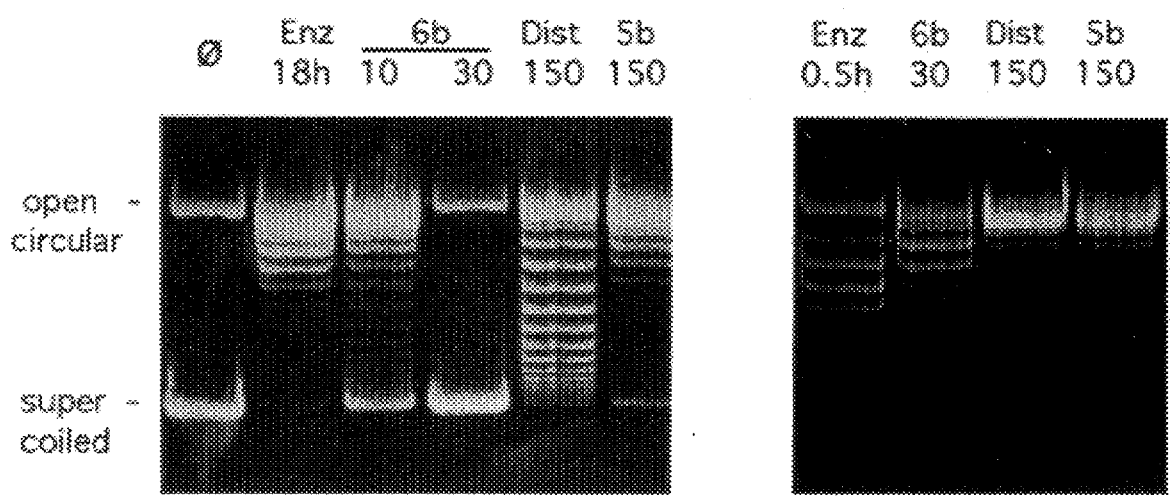

In closely related experiments, the mode of inhibition of topoI was examined. This was accomplished by allowing the supercoiled DNA to be partially relaxed for 0.5 hr with topoI before any other DNA ligands were added (FIG. 6). The 0.5 hr control shows the state of unwinding at the time 5b, 6b, and Dm were added. While 150 μM 5b and Dm demonstrated no effect (compare with the topoI (+) control), 30 μM 6b inhibited topoI even after pBR322 was considerably unwound.

This indicates that of the three compounds surveyed, only 6b is able to effectively compete with topoI once the enzyme is bound. Extrapolating from experiments with the hexadecamer d(GGCGCAAATTTGGCGG)(SEQ ID NO:1)/d (CCGCCAAATTTGCGCC)(SEQ ID NO:2) (Table I), one might anticipate the binding affinity of 6b to pBR322 to be in the range of 2- to 4-fold greater than the binding affinity of 5b to the same hexadecamer. The 2- to 4-fold difference in binding does not explain the inhibition data (FIG. 6).

This suggests that, as with the electrophoretic mobility shift assay, binding of 6b to DNA alters the conformation of DNA. Such an altered DNA conformation could inhibit topoI by either preventing enzyme binding to or "tracking" along DNA, or by generating conformationally uncleavable sites.

Reagents and methods for DNA binding studies were exactly the same as used previously (He, et al., 1993, supra; Browne, et al., 1993, supra) unless stated otherwise. The values for the equilibrium constants for 2, 5a,b,c, Dm, and Ht were recalculated from previously collected data (Browne, et al., 1993, supra) using the curve fitting program SigmaPlot® 4.1.4 (Jandel Scientific, San Rafael, Calif.). The equilibrium constants for 6a and 6b were calculated with SigmaPlot® 4.1.4 using the reevaluated constants for Ht ($K_{Ht1}$ and $K_{Ht2}$).

Topoisomerase I inhibition assays

The buffer for all of the 50 µL reactions was composed of 50 mM Tris-HCl, pH 7.5, 50 mM KCl, 10 mM $MgCl_2$, and 1 mM EDTA that was filtered through a sterile 0.45µ Gelman Sciences Acrodisc. Every reaction mixture contained 1 µg of supercoiled pBR322 plasmid (Pharmacia) and, except for the supercoiled control, every reaction mixture included 10 units of calf thymus topoisomerase I (Bethesda Research Laboratories).

For the supercoil relaxation assays, no added agent, 10 µM or 30 µM 6b, or 150 µM distamycin (Dm) or dien-microgonotropen-b (5b) (He, et al., 1993, supra) were pre-incubated with the supercoiled DNA for 60 min before topoisomerase I was added. These reactions were allowed to run for 18 h at 37° C. at which time the reactions were stopped with the addition of 2 µL of 250 mM EDTA, pH 7.5.

For the supercoil partial relaxation assays, topoisomerase I was incubated with the supercoiled DNA for 30 min at 37° C. before the addition of 30 µM 6b, or 150 µM Dm or 5b. These reactions were allowed to run for an additional 18 h at 37° C. after which time they were stopped as described above.

The supercoil partial relaxation control was stopped after the initial 30 min at 37° C. All reactions were extracted twice with water-saturated phenol, extracted once with chloroform, and precipitated with ammonium acetate and ethanol.

After the DNA pellets were dissolved in 9 µL of 10 mM Tris-HCl, pH 8.0, and 1 mM EDTA, 1.0 µL of loading buffer (Sambrook, J.; Fritsch, E. F.; Maniatis, T. *Molecular Cloning, A Laboratory Manual;* 2nd Edition, Cold Spring Harbor, N.Y., 1989) (10% (w/v) glycerol, 0.1% (w/v) sodium dodecyl sulfate, and 0.1% (w/v) bromophenol blue) was added to each sample.

The different helical forms of pBR322 created by the relaxation assays were electrophoretically separated through a 4% NuSieve 3:1 (hydroxyethylated) agarose gel (vertical, 0.8 mm) in 40 mM Tris-acetate, pH 8.0 and 1 mM EDTA for 8 hr at 2 V/cm. The gel was stained with a 0.5 µg/mL solution of ethidium bromide in deionized water for 30 min, destained for 15 min in deionized water, and photographed on a UV (302 nm) transilluminator with Polaroid type 667 film.

EXAMPLE II

MATERIALS AND METHODS

The synthesis of 6b was described in Example I. The self complementary d(CGCAAATTTGCG (SEQ ID NO:3))$_2$ was obtained by annealing (Browne et al., 1993, supra) the single stranded DNA oligomer prepared and purified at the Biomolecular Resource Center, University of California, San Francisco.

The NMR samples contained either 0.38 or 2.5 mM (µ=0.079 and 1.2, respectively) d(CGCA$_3$T$_3$GCG (SEQ ID NO:3))$_2$ in 10 mM potassium phosphate buffer and 10 mM NaCl at pH 7.0 with 0.1% DSS in 0.4 mL $D_2O$. Concentrations of ssDNA were determined from the absorbance at 260 nm ($\epsilon_{260}$,single-stranded=$1.36 \times 10^5 M^{-1}$ cm$^{-1}$, 60° C.)

One equivalent of 6b was added to 0.4 mL of 2.5 mM oligomer and this sample was lyophilized twice from 99.9% $D_2O$, once from 99.96% $D_2O$, and finally dissolved in 0.4 mL of 99.96% $D_2O$ (Aldrich) under a nitrogen atmosphere. (The titration sample was dried in an analogous manner in the absence of 6b.) The solution was kept refrigerated at 4° C. between uses. All NMR spectra were recorded at 500 MHz on a GN-500 (General Electric) spectrometer at 10° C., unless otherwise specified. Chemical shifts were referenced to the signal of DSS (0 ppm).

1D NMR.

The titration experiment was performed in $D_2O$ at 21° C. in 0.25 mole equiv. steps of 6b/d(CGCA$_3$T$_3$GCG (SEQ ID NO:3))$_2$ at $3.8 \times 10^{-4}$M of d(CGCA$_3$T$_3$GCG (SEQ ID NO:3))$_2$. Mesitoate (2,4,6-trimethylbenzoate) was present at $3.8 \times 10^{-4}$M as an internal standard. The melting study of dsDNA was performed at $3.8 \times 10^{-4}$M of d(CGCA$_3$T$_3$GCG (SEQ ID NO:3))$_2$ between 20° and 60° C. with DSS (2,2-dimethyl-2-silapentane-3,3,4,4,5,5-d$_6$-5-sulfonate) as an internal standard.

2D NMR.

NOESY experiments were recorded in the phase sensitive mode using the hypercomplex NOE pulse sequence (States, D. J.; Haberkorn, R. A.; Ruben, D. J. *J. Magn. Reson.*, 1982, 48,286) with mixing times of 50, 100 and 180 ms for the d(CGCA$_3$T$_3$GCG (SEQ ID NO:3))$_2$: 6b complex. Spectra were collected into 4K complex points for 512 $t_1$ increments with a spectral width of 5681 Hz in both dimensions.

The data matrix was zero filled to 2K and appodized with a gaussian function to give a line broadening of 1 Hz in both frequency domains. The ROESY experiment was recorded at 10° C. using the Kessler pulse sequence (Kessler, H.; Griesinger, C.; Kerssebaum, R.; Wagner, E.: Ernst, R. *J Am. Chem. Soc.* 1987, 109, 607) with a mixing time of 50 ms and a locking field strength of 2.5 kHz.

Notations

Here, as elsewhere (Blaskó et al., 1993, supra; (a) Patel, D. J.; Shapiro, L. *Biochimie* 1985, 67, 887, (b) Patel, D. J.; Shapiro, L. *J. Biol. Chem.* 1986, 261, 1230, (c) Patel, D. J.; Shapiro, L.; Hare, D. *Q. Rev. Biophys.* 1987, 20, 35, (d) Gao, X.; Patel, D. J. *Q. Rev. Biophys.* 1989, 22, 93), the numbering of DNA protons follows the rule that the sugar protons will be denoted by prime and double prime superscripts and preceded by the name of the residue to which they belong.

When reference is made to the same proton of more than one residue, all residues are listed followed by the proton type (e.g. $A_6T_7T_8$H2" means the H2" (sugar) protons which belong to the $A_6$, $T_7$, and $T_8$ residues; $G_2G_{10}G_{12}$H8 means the H8 (base) protons of the $G_2$, $G_{10}$ and $G_{12}$ residues). When both H2' and H2" protons are involved in discussion, we used the H2'2" abbreviation.

Distance calculations were made by measuring the volume integrals of the NOE enhancements from the 180 ms NOESY spectrum which were then related to interproton distances by eq 2 where $r_a$ and $$r_a = r_b(NOE_b/NOE_a)^{1/6}, Å \qquad \text{eq (2)}$$

$r_b$ are the distances corresponding to the unknown and known (C$_1$H5-C$_1$H6, 2.45 Å) interactions of a pair of protons with their corresponding NOE$_a$ and NOE$_b$ (Zhang, X.; Patel, D. J. *Biochemistry* 1990, 29, 9451).

The linearity of the NOE build-up with $t_m$ was checked for most of the dsDNA proton interactions between 50 and 180 ms and a 5–20 fold increase was found in the NOE volume integrals from the 50 to 180 ms mixing times. The exchange rate ($k_{ex}$) was calculated from eq 3 as follows:

$$k_{ex}=\ln((1+R)/2\tau_m(1-R)), s^{-1} \qquad eq(3)$$

using the ratio of peak intensities (R), expressed in number of contour levels (off diagonal/diagonal) from a short mixing time ($\tau_m$) ROESY spectrum (Ernst, R. R.; Bodenhausen, G.; Wokaun, A. "Principles of Nuclear Magnetic Resonances in One and Two Dimensions", Clarendon Press, Oxford, 1987).

The free energy of activation, $\Delta G^*$, for this exchange process at a certain temperature, T (K), was calculated from eq 4 (Günther, H. "NMR Spectroscopy: An Introduction", John Wiley, New York, 1980, p. 241).

$$\Delta G^*=19.14T(10.32-\log(k_{ex}/T)), J/\text{mol} \qquad eq(4)$$

Computational Analysis and Restrained Molecular Modeling were performed on a Silicon Graphics (Mountain View, Calif,) Iris 4D/340GTX workstation using CHARMm (Brooks, B. R.; Bruccoleri, R. E.; Olafson, B. D.; States, D. J.; Swaminathan, S.; Karplus, M. *J. Comp. Chem.* 1983, 4, 187) (version 21.3) and QUANTA (version 3.3.1) programs (Molecular Simulations, Waltham, Mass.).

The solution structure of 5c in a complex with d(CGCA$_3$T$_3$GCG)$_2$ was used as initial coordinates for 6b (Blaskó, et al., 1993, supra). The aliphatic chain and dien polyamino group on the central pyrrole nitrogen of 5c was replaced with a (CH$_2$)$_4$ methylene chain and a tren moiety {—NHCH$_2$CH$_2$N(CH$_2$CH$_2$NH$_2$)$_2$} using 3D Molecular Editor (QUANTA).

Atomic partial charges of the atoms in 6b and d(CGCA$_3$T$_3$GCG (SEQ ID NO:3))$_2$ were generated from CHARMm's force field's parameter files. Primary, secondary, and tertiary amines were modeled as fully protonated with a total charge of +5 for 6b (partial charge of +0.35 for each protonated amine of 6b).

To the solution structure of the dodecamer (Blaskó, et al., 1993, supra) 6b was docked into the minor groove to initiate structural refinement of the 1:1 complex of d(CGCA$_3$T$_3$GCG (SEQ ID NO:3))$_2$: 6b. CHARMm minimization was subsequently conducted exactly as previously described for 5c (Blaskó, et al., 1993, supra) with the following exception: only 2 Na$^+$ gegenions were removed from vicinity of the phosphates nearest to where the protonated polyamine sidechain and dimethylamine tail of 6b were initially located.

Molecular and helical parameters were also measured exactly as before (Blaskó, et al., 1993, supra; NEWHEL93 was generously provided by R. E. Dickerson. The program was run on a VAXstation 3100 with coordinates in Brookhaven's Protein Data Bank format. The best helicies were generated from the sugars' C1', the pyrimidine's N1, and the purine's N9 atoms. For more information on an earlier version of this program, see Prive, G. G.; Yanagi, K.; Dickerson, R. E. *J. Mol. Biol.* 1991, 217, 177). Dihedral angle constraints were not included in the simulations.

The distances of 6b to the DNA (−) and (+) strands were measured from the pyrrolic nitrogens to P$_{-4}$P$_{-5}$P$_{-6}$ and P$_8$P$_9$P$_{10}$, respectively. The depth of 6b binding was defined by measuring the distances from the amide nitrogens N1, N2, and N3 to the lines connecting T$_{-6}$O2 and A$_6$H2, A$_{-7}$H2 and T$_7$O2, and A$_{-8}$H2 and T$_8$O2 atoms, respectively.

Results

Titration of d(CGCAAATTTGCG (SEQ ID NO:3))$_2$ with 6b

All changes in the imino proton region (12–15 ppm) occur prior to reaching a 1:1 ratio of d(CGCA$_3$T$_3$GCG (SEQ ID NO:3))$_2$ and 6b when recording the $^1$H NMR spectra in 9:1 H$_2$O:D$_2$O solvent. The titration of d(CGCA$_3$T$_3$GCG (SEQ ID NO:3))$_2$ (3.8×10$^{-4}$M) with 6b was carried out in 0.25 mole equiv. steps in D$_2$O at 21° C. (FIG. 7).

In contrast with the H$_2$O experiment, the nonexchangeable proton signals continue to change after reaching a mole ratio of 1:1 in 6b/d(CGCA$_3$T$_3$GCG (SEQ ID NO:3))$_2$ when titrating in D$_2$O (vide infra). In these titrations we employed mesitoate (2,4,6-trimethylbenzoate), at a 1:1 mole ratio with respect to dsDNA, as an internal standard. The mesitoate CH$_3$ protons resonate at 2.22 ppm (2,6-position) and 2.24 ppm (4-position) while the aromatic protons (3,5-position) are at 6.90 ppm. The titration was followed up to a 2.5 mole ratio of 6b to d(CGCA$_3$T$_3$GCG (SEQ ID NO:3))$_2$.

The affected dsDNA resonances double at the 1:1 mole ratio and give line broadenings. At the 2:1 mole ratio, the resonances corresponding to the 1:1 ratio have collapsed and one observes only one set of equivalent resonances when monitoring the thymidine methyl signals (1.2–1.7 ppm). There is a downfield shift of the aromatic adenosine signals of d(CGCA$_3$T$_3$GCG (SEQ ID NO:3))$_2$ and an upfield shift of the pyrrole aromatic signals of 6b (FIG. 7a–c).

The assignment of the resonances of 6b in H$_2$O (DQF-COSY, FIG. 21) is shown in Table II. These assignments were used as a lead for the assignment of the resonances of 6b in the dsDNA: 6b 1:1 complex. The Double Quantum Filtered Homonuclear J-Correlated Spectroscopy (DQF-COSY) spectrum of the 1:1 complex (FIGS. 22–25) shows the connectivities in the R2 and R3 propylamine and tren-polyamine groups; their chemical shifts are summarized in Table II.

The H2, H4, and H6 pyrrole resonances of 6b (FIG. 19a) are found in the 6.5–6.8 ppm region. They give NOEs with the aromatic adenosine A$_{-7}$A$_{-8}$H2 protons of the (−) strand and with the sugar A$_5$H1' and A$_{-8}$H1' protons, respectively. The H1, H3, and H5 resonances of 6b were assigned using their intramolecular interactions with the CH$_2^n$(i) methylenes of the central hydrocarbon linker and with the CH$_3^{R1}$ group of the acetamide substituent (FIGS. 8 and 9). The assignment of the 6b resonances were confirmed by the NOE enhancements in the NOESY spectrum (FIGS. 8, 9, 10, 26 and 27).

Assignment of $^1$H chemical shifts of d(CGCAAATTTGCG (SEQ ID NO:3))$_2$ in the 1:1 complex with 6b The finding of two sets of Watson-Crick G≡C and A=T resonances and two sets of thymidine CH$_3$ resonances at the 1:1 mole ratio of 6b/d(CGCA$_3$T$_3$GCG (SEQ ID NO:3))$_2$ is indicative of an asymmetric, monomeric binding of the ligand to the DNA molecule, as was found in the case of the d(CGCA$_3$T$_3$GCG (SEQ ID NO:3))$_2$: 5c complex (Blaskó, A., et al., 1993, supra).

Expansion of the NOESY spectrum in the (1.1–3.0)× (6.7–8.5) ppm region (FIG. 9) shows the general pattern of NOESY interactions of H6/8-H2'2", H6/8-T$_i$CH$_3$, and T$_i$CH$_3$-T$_{i+1}$CH$_3$ used for the assignment of sugar H2'2" resonances (Table III).

A good point to initiate assignments of the dsDNA resonances is at the signals of T$_7$T$_{-6}$CH$_3$. This procedure was used in the case of free d(CGCA$_3$T$_3$GCG (SEQ ID NO:3))$_2$ and the d(CGCA$_3$T$_3$GCG (SEQ ID NO:3))$_2$: 5c complex (Blaskó, A., et al., 1993, supra). The T$_7$T$_{-6}$CH$_3$ signals were used for the assignment of A$_6$A$_{-7}$H8, $T_7T_8T_9H6$ and $T_{-4}T_{-5}T_{-6}H6$ proton resonances (FIG. 9). Here and elsewhere (Blasko, A., et al., 1993, supra), we use the convention that the (+) strand is the binding site side and the (−) strand is the complementary DNA strand.

The remaining aromatic resonances were assigned using the known resonances of cytidine H6/5 (DQF-COSY, FIG. 22) which give strong intraresidual NOEs (FIG. 8) and using the interactions between two adjacent $A_{n-1}A_nH8$ protons (8.05 and 8.25 ppm). We also used the proven fact that 6b binds into the minor groove at A+T-rich regions (He, G.-X., et al., 1993, supra). We saw NOE enhancements between $A_{-8}H8$ and $A_{-9}H8$ and also weak enhancements between $A_5H8$ and $A_6H8$. Both enhancements were used for the dsDNA sequential assignment.

The guanosine H8 resonances (7.8–8.0 ppm) were used to define the $C_1G_2G_{12}H1'$ and $T_{-4}H1'$ resonances (FIG. 8). We did not see NOE build-ups between $G_{10}H8$ and any of the H3' or H5'5" protons and no NOEs between adenosine H8 and H5'5" protons. Defining the position of $A_6H1'$ is important in the intracomplex interactions (vide infra). We found weak NOEs between $A_6H8$ and $A_6H1'$ (FIG. 8). The crowded region of H4' and H5'5" was resolved (where possible) using their NOEs with H1' protons (FIG. 26 and Table III).

Intracomplex interactions of d(CGCAAATTTGCG (SEQ ID NO:3))$_2$ and 6b

Tren-microgonotropen-b (6b) binds into the A+T-rich region of the minor groove of $d(CGCA_3T_3GCG$ (SEQ ID NO:3))$_2$ in 1:1 and noncooperative 2:1 mole ratios. These complexations also involve one G.C bp (vide supra). Expansion of the NOESY spectrum in the (5.3–8.3)×(5.3–8.3) ppm region reveals strong NOE interactions between the H2, H4 and H6 pyrrole protons and the $A_{-8}H2$ and $A_{-7}H2$ protons as well as a small NOE for H4 with the sugar $A_{-8}H1'$ proton (FIGS. 8 and 26). The acetamido $CH_3^{R1}$ methyl protons of 6b give NOEs with $T_{-4}H6$ and $A_6H1'$ (FIGS. 9 and 10) defining the orientation of the 6b molecule in the minor groove. The dimethylpropylamino substituent, R3, approaches the $G_{10}$ residue, defined by the NOE build-up between the $CH_3^{R3}$ and $G_{10}H1'$ (FIG. 10)

The tren polyamino substituent of the central pyrrole ring of 6b strongly interacts with the sugar protons of $T_8$ and $T_9$. We saw NOEs between $CH_2{''}(2)$ and $T_8T_9H3'$, between $CH_2{''}(3)$ and $T_9H3'$ (FIG. 10) and between $CH_2{''}(4)$ and $T_8H5"$ (FIG. 27). Other intracomplex interactions were seen between $CH_3^{R5}$ and $T_9H4'$ (FIG. 26) and between H5 and $A_{-8}H2"$ (FIG. 9). An inter-residual NOE was also seen between $T_7H5"$ and $A_6H2$ (FIG. 28).

TABLE II $^1$H Chemical Shifts for 6b, Free and in the 1:1 Complex with $d(CGCA_3T_3GCG(SEQ\ ID\ NO:\ 3))_2$ in $D_2O$.

| Residue | Proton | $d(CGCA_3T_3GCG(SEQ\ ID\ NO:\ 3))_2$:6b | $d(CGCA_3T_3GCG(SEQ\ ID\ NO:\ 3))_2$ | $\Delta\delta^b$ |
|---|---|---|---|---|
| pyrrole | H1 | 7.07 | 7.18 | −0.11 |
| pyrrole | H3 | 7.24 | 7.01 | 0.23 |
| pyrrole | H5 | 7.26 | 7.06 | 0.20 |
| pyrrole | H2 | 6.63 | 6.70 | −0.07 |
| pyrrole | H4 | 6.74 | 6.74 | 0.00 |
| pyrrole | H6 | 6.57 | 6.71 | −0.14 |
| R1 | methyl | 2.08 | 1.98 | 0.10 |
| R3 | methyl | 2.87 | 2.63 | 0.24 |
| R4 | methyl | 3.97 | 3.76 | 0.21 |
| R5 | methyl | 3.97 | 3.76 | 0.21 |
| $CH_2^{R2}$ | (1) | 2.36 | 2.70 | −0.34 |
| $CH_2^{R2}$ | (2) | 2.62 | 2.92 | −0.30 |
| $CH_2^{R2}$ | (1') | 3.01 | 2.94 | 0.07 |
| $CH_2^{R2}$ | (2') | 2.77 | 2.68 | 0.09 |
| $CH_2^{R3}$ | (1) | 3.12 | 3.33 | −0.21 |
| $CH_2^{R3}$ | (2) | 1.87 | 1.90 | −0.03 |
| $CH_2^{R3}$ | (3) | 2.03 | 2.88 | −0.85 |
| $CH_2{''}$ | (1) | 5.41 | 4.18 | 1.23 |
| $CH_2{''}$ | (2) | 1.76 | 1.73 | 0.03 |
| $CH_2{''}$ | (3) | 2.16 | 1.60 | 0.56 |
| $CH_2{''}$ | (4) | 3.14 | 2.85 | 0.29 |

$^a\delta$ in ppm relative to TSP at 10° C.; [dsDNA] = 2.5 × 10$^{-3}$ M (10 mM phosphate buffer, pH 7.0, 10 mM NaCl).
$^b\delta_{complex} - \delta_{free\ dsDNA}$.

TABLE III $^1$H Chemical Shifts for $d(CGCA_3T_3GCG)_2$ in the 1:1 Complex with 6b in $D_2O$.$^a$

| Base | H1' | H2' | H2" | H3' | H4' | H5' | H5" | H6/8 | H2/5/CH$_3$ |
|---|---|---|---|---|---|---|---|---|---|
| (+) strand | | | | | | | | | |
| 5'-C$_1$ | 5.71 | 1.95 | 2.37 | 4.68 | 4.04 | 4.03 | 3.70 | 7.60 | 5.82 |
| G$_2$ | 5.84 | 2.64 | 2.68 | 4.94 | 4.33 | 4.40 | 4.35 | 7.94 | |
| C$_3$ | 5.75 | 1.90 | 2.33 | 4.82 | 4.18 | 4.18 | 4.12 | 7.39 | 5.42 |
| A$_4$ | 5.81 | 2.74 | 2.80 | 5.06 | 4.38 | 4.47 | 4.22 | 8.20 | 7.18 |
| A$_5$ | 5.55 | 2.72 | 2.78 | 5.03 | nd$^b$ | 4.46 | 4.36 | 8.25 | 6.98 |
| A$_6$ | 5.84 | 2.68 | 2.77 | 5.06 | 4.22 | 4.40 | 4.22 | 8.13 | 7.46 |
| T$_7$ | 5.36 | 1.97 | 2.41 | 4.62 | nd | 4.02 | 3.88 | 6.93 | 1.23 |
| T$_8$ | 5.64 | 2.00 | 2.31 | 4.63 | 3.70 | 3.88 | 3.35 | 7.18 | 1.46 |
| T$_9$ | 5.42 | 1.98 | 2.30 | 4.78 | 4.10 | 4.20 | 4.10 | 7.11 | 1.56 |
| G$_{10}$ | 5.84 | 2.55 | 2.66 | 4.98 | 4.01 | 4.35 | 4.12 | 7.80 | |
| C$_{11}$ | 5.70 | 1.93 | 2.33 | 4.83 | 4.03 | 4.18 | 4.13 | 7.36 | 5.41 |
| G$_{12}$ | 6.15 | 2.36 | 2.62 | 4.67 | 4.18 | 4.17 | 4.06 | 7.95 | |
| (−) strand | | | | | | | | | |
| C$_{-12}$ | 5.71 | 1.95 | 2.37 | 4.68 | 4.04 | 3.98 | 3.70 | 7.58 | 5.82 |
| G$_{-11}$ | 5.84 | 2.64 | 2.68 | 4.94 | 4.33 | 4.40 | 4.35 | 7.94 | |
| C$_{-10}$ | 5.75 | 1.90 | 2.33 | 4.82 | 4.18 | 4.18 | 4.12 | 7.39 | 5.42 |
| A$_{-9}$ | 5.81 | 2.79 | 2.89 | 5.06 | nd | 4.47 | 4.22 | 8.15 | 7.53 |
| A$_{-8}$ | 5.52 | 2.78 | 2.89 | 5.08 | 4.22 | 4.46 | 4.36 | 8.23 | 8.08 |
| A$_{-7}$ | 5.86 | 2.71 | 2.81 | 5.05 | nd | 4.40 | 4.22 | 8.08 | 8.12 |
| T$_{-6}$ | 5.70 | 1.97 | 2.41 | 4.64 | nd | 4.15 | 3.92 | 6.87 | 1.21 |
| T$_{-5}$ | 6.17 | 2.00 | 2.40 | 4.62 | 3.70 | 4.00 | 3.85 | 7.22 | 1.48 |

TABLE III-continued

¹H Chemical Shifts for d(CGCA₃T₃GCG)₂ in the 1:1 Complex with 6b in D₂O.*

| Base | H1' | H2' | H2" | H3' | H4' | H5' | H5" | H6/8 | H2/5/CH₃ |
|---|---|---|---|---|---|---|---|---|---|
| T₋₄ | 5.75 | 1.98 | 2.42 | 4.78 | 4.10 | 4.15 | 4.10 | 7.28 | 1.62 |
| G₋₃ | 5.78 | 2.36 | 2.66 | 4.97 | 4.01 | 4.10 | 3.98 | 7.92 | |
| C₋₂ | 5.70 | 1.93 | 2.32 | 4.83 | 4.03 | 4.18 | 4.13 | 7.36 | 5.35 |
| G₋₁ | 6.15 | 2.36 | 2.62 | 4.67 | 4.18 | 4.17 | 4.06 | 7.95 | |

*δ in ppm relative to TSP at 10° C.; [dsDNA] = 2.5 × 10⁻³ M (10 mM phosphate buffer pH 7.0, 10 mM NaCl). The Watson-Crick imino protons (recorded in H₂O) are in the range: A=T 13.5–14.2 and G≡C 12.5–13.1 ppm (Blaskó, A., Bruice, T.C. PNAS (USA) 1993 90: 10018).
ᵇnot determined.

No NOEs were detected between the R2 polyamino substituent of 6b and d(CGCA₃T₃GCG (SEQ ID NO:3))₂. However, the NOE build-up between $CH_2^n(4)$ and $CH_2^{R2}$ (2') protons (FIGS. 11 and 27) will define the position of this part of the R2 polyamine group of 6b with regard to the dsDNA molecule (note that the position of the $CH_2^n$ chain was already defined from their NOEs with d(CGCA₃T₃GCG (SEQ ID NO:3))₂; vide supra). A survey of the sequential NOEs for the DNA selected protons in the ligated dsDNA is shown in Table IV.

Induced chemical shift differences (Δδ) are observed in certain proton resonances (FIG. 12) due to the minor groove binding. This is primarily due to the ring current effect from both the dsDNA and the tripyrrole peptide. The Δδ extends beyond the binding site due to distortion of the dsDNA upon binding.

With the exception of the T₈H5" (Δδ=–0.8 ppm (FIG. 12), the differences are greater for the H1' protons (minor groove pointers) than for any other selected protons. The increase in Δδ follows the order H2'<H6/8<H3'<H2"≈H5'<H1'. The aromatic pyrrole protons, H3 and H5, give upfield shifts upon binding (Δδ=0.2 ppm) while H1, H2 and H6 give downfield shifts (Δδ=–0.1 ppm) (Table II).

All the CH₃ groups of R1, R3, R4 and R5 give upfield shifts (Δδ=0–0.2 ppm). Small downfield shifts were seen in the case of $CH_2^{R2}(1')$, $CH_2^{R3}(1)$, $CH_2^{R3}(2)$ (Δδ<–0.1 ppm) and small upfield shifts in the case of $CH_2^{R2}(2')$ and $CH_2^n$ (2') (Δδ=0.2 ppm). Large upfield shifts are exhibited by the hydrocarbon linker methylene resonances (Δδ=0.3–1.2 ppm), the highest (Δδ=1.2 ppm) being at $CH_2^n(1)$. Large downfield shifts were seen in the case of $CH_2^{R3}(3)$ (Δδ=–0.8 ppm) and in the case of $CH_2^{R2}(1)$ and $CH_2^{R2}(2)$ (Δδ=–0.3 ppm). These are due to their adjacent protonated amines which are involved in hydrogen bonding to phosphates.

Sugar puckerings of d(CGCAAATTTGCG (SEQ ID NO:3))₂

From the DQF-COSY spectrum of the d(CGCA₃T₃GCG (SEQ ID NO:3))₂: 6b complex (FIGS. 22–25), coupling constants can be estimated and, therefore, some sugar residues can be characterized in terms of their vicinal proton dihedral angles.

TABLE IV

Comparison of the Sequential NOEs for: (a) d(CGC₃T₃GCGA(SEQ ID NO: 3))₂ and (b) the 1:1 Complex of d(CGCA₃T₃GCG(SEQ ID NO: 3))₂ with 6b.

| a. (±) strand | C₁ | G₂ | C₃ | A₄ | A₅ | A₆ | T₇ | T₈ | T₉ | G₁₀ | C₁₁ | G₁₂ | (SEQ ID NO: 3) |
|---|---|---|---|---|---|---|---|---|---|---|---|---|---|
| H6/8—CH₃ | | | | | | | o---o---o---o | | | | | | |
| H6/8—H1' | o---o | | | | | | o---o---o | | | | | | |
| H6/8—H2" | o---o | | | | | | o---o---o---o---o---o---o---o---o | | | | | | |
| CH₃—CH₃ | | | | | | | | o---o | | | | | |
| H6—H6 | | | | | | | o---o---o---o | | | | | |
| b. (+) strand: | C₁ | G₂ | C₃ | A₄ | A₅ | A₆ | T₇ | T₈ | T₉ | G₁₀ | C₁₁ | G₁₂ | (SEQ ID NO: 3) |
| H6/8—CH₃/H5/6/8 | | | | | | | o---o---o---o | | | o---o | | |
| H6/8/5—H1' | o---o | | | | | | | | | | o---o | | |
| H6/8/CH₃—H2" | o---o---o | | | | o---o | | | o---o | | o---o---o | | |
| H6/8—H3' | | | | | | | | | | | | o---o | |
| H2/CH₃—H/CH₃ | | | | o---o | | | o---o | | | | | | |
| b. (–) strand: | C₋₁₂ | G₋₁₁ | C₋₁₀ | A₋₉ | A₋₈ | A₋₇ | T₋₆ | T₋₅ | T₋₄ | G₋₃ | C₋₂ | G₋₁ | (SEQ ID NO: 3) |
| H6/8—CH₃/H5/6/8 | | | | | | | o---o | o---o---o---o | | | o---o | | |
| H6/8—H1' | | | | o---o | | | o---o---o | | o---o | | | |
| H6/8/CH₃—H2" | | o---o | | o---o | | | o---o---o | | | | o---o | |
| H6/8—H3' | | | | | | | | | | | | o---o | |
| H2/CH₃—H2/CH₃ | | | | | | | o---o---o---o---o | | | | | |

In terms of sugar puckering, the DNA's backbone conformation is dictated by the glycosidic torsion angle defined by C5'-C4'-C3'-O3'. The exact ³J coupling constants involving H3' are hard to determine due to their passive coupling including phosphorus (Kim, S.-G.; Lin, L.-J.; Reid, B. R. Biochemistry 1992, 31, 3564). However, they can be qualitatively constrained into restricted ranges from the corresponding cross-peaks intensities (Kim, S.-G., et al., 1992, supra).

Cross-peaks between H3'-H2" and H3'-H4' were weak or nonexistent in the DQF-COSY spectrum of the 1:1 complex (FIG. 22), except for some terminal base pairs. These very small coupling constants are indicative of the presence of the B-form of dsDNA (Kim, S.-G., et al., 1992, supra). Since the sugar conformation can be determined from the NOESY-derived distance data, the coupling constants estimated from the DQF-COSY complements the NOESY/RM characterization of the complexed dsDNA.

In the cases of the well resolved H1'-H2" and H1'-H2' cross-peaks, sugar coupling constants were estimated for G₁₀, G₁₂, C₁, C₃, and C₁₁ to be 3–5 Hz and 1.5 Hz for A₄ and A₆ (FIGS. 23–25). In all cases ³J$_{H1'-H2'}$>³J$_{H1'-H2''}$. This limits the deoxyribose pseudorotational phase angles (P) to 90°–190° (Kim, S.-G., et al., 1992, supra).

In the case of the terminal base pairs $C_1$, $C_3$, and $G_{12}$, the coupling constants for H3'-H4' were 3–5 Hz, while for the binding site residue $T_9/T_{-4}$, 2.5 Hz, placing them close to P=126°, H1'-exo and P=140°–162°, H2'-endo, respectively. No other cross-peaks could be seen and/or resolved.

Distance calculations and restrained molecular modeling refinements

For the 1:1 complex of the dodecamer d(CGCA$_3$T$_3$GCG (SEQ ID NO:3))$_2$ and 6b, 155 intramolecular interactions were found for both NMR-nonequivalent strands. Of these, 17 were used in refining the DNA distances of the previously determined solution structure of d(CGCA$_3$T$_3$GCG (SEQ ID NO:3))$_2$ (Blaskó, A., et al., 1993, supra) (Table V).

These intramolecular interactions represent the only well separated cross peaks (Table IV). In addition, 17 interactions between 6b and the dsDNA and intramolecular 6b interactions were used for docking (FIG. 11; Table V). The same minimization procedure used previously (Blaskó, A., et al., 1993, supra) was employed to obtain the most probable solution structure of the 1:1 complex of 6b with d(CGCA$_3$T$_3$GCG (SEQ ID NO:3))$_2$ (FIGS. 13A–C).

All deviations in the refined structure from the calculated NOE distances were less than 0.6 Å. The ROESY spectrum (FIG. 29) confirms most of the NOESY enhancements.

TABLE V

Experimental (NOESY) and Refined (Molecular Modeling) Distances for the 1:1 Complex of d(CGCA$_3$T$_3$GCG(SEQ ID NO: 3))$_2$ with 6b. in D$_2$O.[a] (Refined distances are in parentheses.)

a. Distances involving only d(CGCA$_3$T$_3$GCG)SEQ ID NO: 3))$_2$ protons:

|  |  | H1' | H2' | H5' | H6/8 | CH$_3$/H5/H2* |
|---|---|---|---|---|---|---|
| G$_2$ | H8 | 3.9[b](4.0) | | | | |
| C$_3$ | H6 | 4.1 (4.0) | | | | |
| A$_4$ | H8 | 4.9 (4.3) | | | | |
| A$_5$ | H8 | 3.9 (3.9) | | | | |
| A$_6$ | H8 | | | | | 4.1[b](4.1) |
| A$_6$ | H2 | | | | 3.4[c](3.9) | |
| T$_8$ | H6 | | 4.3[b](4.2) | | | 3.8[c](3.8) |
| T$_8$ | CH$_3$ | | | | | 4.3[b](4.4) |
| G$_{12}$ | H8 | 3.7 (3.8) | 4.9[b](4.8) | | | 4.0[b](4.2) |
| T$_{-5}$ | H6 | | | | | 3.8[c](3.8) |
| T$_{-6}$ | H6 | | | | | 4.4[c](4.4) |
| A$_{-7}$ | H8 | | | | | 4.3[c](4.3) |
| A$_{-8}$ | H2 | | | | | 4.7*[c](4.6) |
| A$_{-9}$ | H8 | 4.2 (4.1) | | | | | b. Distances involving d(CGCA$_3$T$_3$GCG(SEQ ID NO: 3))$_2$ and 6b protons:

H2-A$_{-7}$H2 3.4(3.4); H4-A$_{-7}$H2 3.7(3.7); H4-A$_{-8}$H1' 4.0(4.3);
H4-A$_{-8}$H2 3.6(3.6); H6-A$_{-8}$H1' 4.0(3.8); H6-A$_{-8}$H2 3.8(3.8);
CH$_3$$^{R1}$—A$_6$H1' 4.2(4.1); CH$_2$$^{R1}$-T$_{-4}$H6 4.0(4.5); CH$_2$$^n$(3)—T$_9$H3' 3.6 (4.0);
CH$_2$$^n$(2)—T$_9$H3' 3.8(3.8); CH$_2$$^{R3}$—G$_{10}$H1' 4.8(4.8);
H1—CH$_3$$^{R1}$ 3.8(4.2); H3—CH$_2$$^n$(1) 3.0(3.0); H3—CH$_2$$^n$(3) 3.8(4.4);
H5—CH$_2$$^n$(2) 3.3(3.8); CH$_2$$^n$(4)—CH$_2$$^{R2}$(2) 4.0(4.2);
CH$_2$$^n$(4)—CH$_2$$^{R2}$(2') 4.0(4.2)

[a]In Å, with the same residue. [b]Distances with the (n − 1) residue. [c]Distances with the (n + 1) residue. Distances marked with asterisks (*) belong to the protons marked with asterisks.

Comparison of solution structures of d(CGCA$_3$T$_3$GCG (SEQ ID NO:3))$_2$ (Blaskó, A., et al., 1993, supra) and the d(CGCA$_3$T$_3$GCG (SEQ ID NO:3))$_2$: 6b complex shows that the minor groove widens considerably between the T$_{-5}$ to T$_9$ and T$_{-4}$ to T$_8$ phosphates (4–3 Å, respectively) upon complexation of 6b. The ligand binds 7.3–9.0 and 5.5–6.4 Å from the (−) and (+) strands, respectively, when examining the regions from T$_{-4}$ to T$_{-6}$ and G$_{10}$ to T$_8$ (distances from the pyrrole nitrogens to P$_{-4}$P$_{-5}$P$_{-6}$ and P$_8$P$_9$P$_{10}$ respectively; Experimental section).

In addition, the 6b complexed dodecamer lengthens 1 Å relative to the solution structure of the dodecamer (Blaskó, A., et al., 1993, supra) as is evidenced by the unit height (34.93 Å/repeat). This is due to a combination of a relatively unwound helix (turn angle=35.90°/bp), a large axial rise (3.50 Å/bp), and a fairly large helical rise (10.03 bp/repeat). The angle of the bend (α; FIG. 14) in the helical axis of the solution structure of the d(CGCA$_3$T$_3$GCG (SEQ ID NO:3))$_2$ complexed with 6b (22.2°) is more than twice the same angle for the crystal (10.8°) and only 0.8° greater than the solution (21.4°) structure of the d(CGCA$_3$T$_3$GCG (SEQ ID NO:3))$_2$ alone (Blaskó, A., et al., 1993, supra). In the solution structure, the molecular contact surface area between d(CGCA$_3$T$_3$GCG (SEQ ID NO:3))$_2$ and 6b is 518 Å$^2$.

Dynamics of ligand exchange

The signals of the H2, H4, and H6 resonances of 6b exhibit different line broadenings ($\Delta v_{1/2}$=14, 15, and 10 Hz, respectively) when in the 1:1 complex with d(CGCA$_3$T$_3$GCG (SEQ ID NO:3))$_2$ (FIG. 8). This is in accord with minor groove binding (Umemoto, K.; Sarma, M. H.; Gupta, G.; Luo, J.; Sarma, R. H. *J. Am. Chem. Soc.* 1990, 112, 4539). As previously discussed (Blaskó, A., et al., 1993, supra) the broadening could be due to the relatively slow exchange of 6b between two equivalent binding sites and/or to a fast sliding motion in the minor groove.

Exchanges between two equivalent binding sites have been proposed for dsDNA complexes of distamycin (Pelton et al., 1990, supra) and netropsin (Patel et al., 1985, supra). If we consider that the exchange is governed by a "flip-flop" mechanism (Pelton et al., 1990, supra) (FIG. 18), not excluding the possible existence of a fast sliding motion of 6b in the minor groove, the rate of exchange can be calculated (Experimental Section). In studying the identical line shapes of the diagonal and cross peaks, the rate of exchange for this process was found to be 1.3±0.2 s$^{-1}$ (10° C., Experimental Section) corresponding to an activation energy ($\Delta G^*$) of ~17 kcal/mol.

The association constant of 6b with A$_3$T$_3$ sites (e.g. d(GGCGCA$_3$T$_3$GGCGG)(SEQ ID NO:1)/d(CCGCCA$_3$T$_3$GCGCC)(SEQ ID NO:2)} has been determined (Example I) to be 8×10$^8$M$^{-1}$. From this information, dissociation of 6b from the hexadecamer is much slower than association and, therefore, one can consider the rate of exchange equal to the off-rate ($k_{ex} \approx k_{off}$).

Here, and elsewhere (Blaskó, A., et al., 1993, supra), we consider these values as estimates and their determination does not include studies beyond our goal of cross relaxations contributing to the peak intensities and the mixing time profile (Klevit, R. E.; Wemmer, D. E.; Reid, B. R. *Biochemistry* 1986, 25, 3296).

Discussion

Both 1:1 and 2:1 complexes of d(CGCA$_3$T$_3$GCG (SEQ ID NO:3))$_2$ with 6b have been observed. The solution structure of the 1:1 complex of d(CGCA$_3$T$_3$GCG (SEQ ID NO:3))$_2$ with 6b has been determined by 2D NMR spectroscopy and restrained molecular modeling. Due to the complexity of ligation and the dynamics of 6b in the complex with dsDNA, small populations of the free dodecamer or of dodecamer:ligand complexes of structures other than reported here may exist in solution.

The titration of d(CGCA$_3$T$_3$GCG (SEQ ID NO:3))$_2$ with 6b in H$_2$O/D$_2$O 9:1 (at 1.8×10$^{-4}$M of dsDNA) (Blaskó, A., et al., 1993, supra) was carried out to a ratio of 2:1 of 6b to dsDNA. No detectable spectral changes in the imino protons' resonances were observed above a 1:1 mole ratio of 6b to d(CGCA$_3$T$_3$GCG (SEQ ID NO:3))$_2$ (in D$_2$O we could detect a 2:1 complex, vide infra).

The spectral changes in the imino proton region when titrating with 6b show that 6b targets the A+T-rich region involving one G.C residue. The titration in $D_2O$ ([dsDNA] =3.8×10$^{-4}$M) was carried out to a ratio of 2.5:1 of 6b to dsDNA. In this experiment spectral changes in the nonexchangeable protons extended from below a 1:1 ratio to a 2:1 ratio of 6b/d(CGCA$_3$T$_3$GCG (SEQ ID NO:3))$_2$ (FIG. 7).

The doubling of the dsDNA resonances (in the $D_2O$ experiment) below a 1:1 mole ratio is indicative of an asymmetrical type of binding (see thymidine CH$_3$'s (1.2–1.6 ppm)) of 6b to d(CGCA$_3$T$_3$GCG (SEQ ID NO:3))$_2$. The collapse of these resonances to only one set at a 2:1 mole ratio is indicative of a symmetrical binding mode for two 6b per one d(CGCA$_3$T$_3$GCG (SEQ ID NO:3))$_2$.

In a study based on fluorescence measurements, it was found that the equilibrium constants for binding of the first and second molecule of 6b to d(GGCGCA$_3$T$_3$GGCGG) (SEQ ID NO:1)/d(CCGCCA$_3$T$_3$GCGCC)(SEQ ID NO:2) shows slight cooperativity (Example I). Using d(CGCA$_3$T$_3$GCG (SEQ ID NO:3))$_2$ with 6b, our $^1$H NMR examination shows no (or undetectable) cooperativity in binding.

The inability to observe $^1$H NMR spectral changes in the imino region above a 1:1 ratio suggests that at any given time only one of two 6b molecules resides inside the groove (FIG. 19). In the 2:1 complex there should be a fast exchange between the two molecules of 6b when binding to d(CGCA$_3$T$_3$GCG (SEQ ID NO:3))$_2$ such that the minor groove widens (and remains wide during the exchange of two 6b molecules) and, as a result, spectral changes occur. On decreasing the temperature to −5° C., the internal motions of the 2:1 complex of 6b/d(CGCA$_3$T$_3$GCG (SEQ ID NO:3))$_2$ ([dsDNA]=4×10$^{-4}$M) decrease.

At −5° C. broadening of the A.T resonances occur while the G.C signals remain sharp. It was previously shown that the 4:1 distamycin/d(CGCA$_3$T$_3$GCG (SEQ ID NO:3))$_2$ complex maintains its A.T and G.C resonance line widths when going to −10° C. The broadening of the A.T resonances of the 2:1 complex of 6b/d(CGCA$_3$T$_3$GCG (SEQ ID NO:3))$_2$ at −5° C. could be due to (a) an asymmetric 2:1 rigid binding mode in which 6b exchanges between two equivalent sites of the dsDNA or (b) a symmetrical 2:1 binding mode in which two molecules of 6b exchange as shown in FIG. 19. The possibility of an asymmetric, rigid 2:1 binding can be ruled out due to the existence of only one set of 6b resonances.

The binding of the flat tripyrrole peptide portion of 6b in the A+T-rich region of the 1:1 complex results in broadening and downfield shifting of the involved resonances (Leupin, W.; Chazin, W. J.; Hyberts, S.; Denny, W. A.; Wüthrich, K. Biochemistry 1986, 25, 5902). Assignment of the nonexchangeable protons (Table III) revealed two sets of DNA resonances, but only one set of 6b resonances (Table II). This indicates that the predominant structure involves a single type of monomeric binding.

Induced chemical shift differences reveal that the most affected protons involved in the dsDNA to 6b interactions are H1' and H2" (FIG. 12). These chemical shift differences also show the changes which occur at the binding site by the perturbation of the involved protons.

The large chemical shift difference, Δδ, for T$_8$H5" indicates strong interactions between this proton and the CH$_2^n$ hydrocarbon linker of the central pyrrole ring of 6b, consistent with the large Δδ found for the CH$_2^n$ protons (Table II). This observation is in agreement with the refined solution structure of the d(CGCA$_3$T$_3$GCG (SEQ ID NO:3))$_2$: 6b complex (FIGS. 13A–C).

The increase in the number of NOEs observed for H6/8 with CH$_3$/H5/6/8 protons (not involved in the exchange phenomena) as compared to the free DNA (Blaskó et al., 1993, supra) can be ascribed to the stiffening of the DNA molecule at the binding site (Table IV, see H6/8 interactions with CH$_3$/H5/6/8) and/or to the dynamic motion of the dodecamer around a position which would bring the aromatic units of the binding site closer together as seen in the case of 5c (Blaskó et al., 1993, supra).

By convention, we assigned this sequence to the (+) strand. The characteristics of the reduced electrophoretic mobilities on agarose gels of DNA restriction digest fragments after preincubation with 6b suggest a distortion of DNA (He et al., 1993, supra).

Although the differences in the induced chemical shifts beyond the binding site are generally small, even in the case of the terminal base pairs (C$_1$, G$_{-1}$ and G$_{12}$, C$_{-12}$) structural distortions occur upon binding as is evidenced by Δδ≠0 (FIG. 12). The significant Δδ for G$_{10}$H2' enforces our observation that this proton is involved in an interaction with 6b.

A small effect on the proton resonances of the aromatic bases suggests that the binding of 6b does not significantly affect the positions of those protons that are major groove pointers. The upfield shift of the H5' and H5" resonances suggests high electron density around these protons. These electron densities derive from the central tren polyamino substituent of 6b.

The acetamido function of 6b affects the position of A$_6$H5" to a small extent while perturbation of G$_{10}$H5' is by the dimethylpropylamino substituent R3. These chemical shift differences suggest that, aside from the minor groove protons which experience disruption of the DNA ring currents due to 6b binding, all other affected protons are influenced by the conformational changes of the DNA which occurs upon complex formation.

There are changes in base pairing and stacking as well as sugar puckering of d(CGCA$_3$T$_3$GCG (SEQ ID NO:3))$_2$ upon formation of the d(CGCA$_3$T$_3$GCG (SEQ ID NO:3))$_2$: 6b complex. From the derived dihedral angles of the ribose moieties, we can state that the A.T regions of the complexed dsDNA maintains its B-conformation (Kim et al., 1992, supra) and the terminal G.C ends do not.

Instead, the G.C ends appear to exist in an intermediate B- to A-DNA form when monitored by the H3'–H4' dihedral angles. Since the conformation of the terminal base pairs is not strictly maintained due to the dynamic "fraying" of the ends, it is not surprising that those dihedral angles do not correspond to B-DNA.

The —CH$_2$CH$_2$CH$_2$N(CH$_3$)$_2$ tail at the carboxyl terminus of 6b is completely within the minor groove. This observation is consistent with the induced chemical shift differences for the R3 protons of 6b in the complex (Table II). The CH$_3$ protons of the acetamido moiety R1 are slightly deshielded while R3, R4, and R5 methyl protons are strongly deshielded due to their proximities with the phosphate backbone.

A strong deshielding is observed on the first, third and fourth methylene groups of the CH$_2^n$ chain attached to the nitrogen of the central pyrrole ring. This suggests that these three methylenes have proximities with the dsDNA phosphates as shown by the structure of the 1:1 d(CGCA$_3$T$_3$GCG (SEQ ID NO:3))$_2$/6b complex (FIGS. 13A–C). The deshielding of H3 and H5 was ascribed to the pyrrole ring interactions with the phosphate ridge on the minor groove side.

Microgonotropen 6b possesses five aliphatic amino groups: two primary, one secondary and one tertiary in the tren substituent (—CH$_2$CH$_2$CH$_2$CH$_2$NHCH$_2$CH$_2$N ($CH_2CH_2NH_2)_2$) and one tertiary in the dimethyl propylamino tail (—$CH_2CH_2CH_2N(CH_3)_2$). The extent of their protonation when 6b is lodged in the minor groove is not certain. In solution at pH 7.0, 6b would be expected to have at least four of its five amino groups protonated (Bruice, T. C.; Mei, H.-Y.; He, G.-X.; Lopez, V. *Proc. Natl. Acad. Sci. (USA)* 1992, 89, 1700; Lowry, T. H.; Richardson, K. S. "Mechanism and Theory in Organic Chemistry", 3rd Edition, Harper & Row, New York, 1987, p. 311).

The upfield shift of the $CH_2^{R3}$(3) resonance suggests protonation of the —$CH_2CH_2CH_2N(CH_3)_2$ nitrogen. The latter is involved in hydrogen bonding with $C_{11}O4'$. The deshielding of the tren polyamino end methylenes, $CH_2^{R2}$ (1')/(2'), by <0.1 ppm is also suggestive of protonation of the corresponding terminal tren nitrogens involved in hydrogen bondings (the dominant effect on $\Delta\delta$) with the phosphate oxygens of $T_9P$ and $G_{10}P$ as shown by the molecular modeling results (FIG. 13A–C).

We have assumed (vide infra), in our restrained molecular modeling, that all five amino functions are fully protonated. This is in agreement with the induced chemical shift differences for the methylene protons flanking the involved amino groups (Table II). When complexed to dsDNA, the four tren amino groups are intimately associated with two negatively charged phosphates, $T_9P$ and $G_{10}P$.

Examination of the X-ray structure of the d($CGCA_3T_3GCG$ (SEQ ID NO:3))$_2$: distamycin complex (Coll, M.; Frederick, C. A.; Wang, A. H.-J.; Rich, A. *Proc. Natl. Acad. Sci. (USA)* 1987, 84, 8385) and the d($CGCGAATT^{Br}CGCG$ (SEQ ID NO:3))$_2$: netropsin complex (Kopka, M. L.; Yoon, C.; Goodsell, D.; Pjura, P.; Dickerson, R. E. *Proc. Natl. Acad. Sci. (USA)* 1985, 82 1376) leads to the conclusion that the minor groove can increase its width upon binding to lexitropsins. Using X-ray structures, comparison of the width (phosphate to phosphate at the A.T binding site) of the minor grooves of d($CGCA_3T_3GCG$ (SEQ ID NO:3))$_2$ (9.4–9.9 Å) and d($CGCA_3T_3GCG$ (SEQ ID NO:3))$_2$: distamycin complex (9.4–10.8 Å) shows an increase of 0–0.9 Å (Coll et al., 1987, supra).

Using the NMR solution structures, comparison of the width of the minor grooves of d($CGCA_3T_3GCG$ (SEQ ID NO:3))$_2$ (6.5–10 Å) (Blaskó, A., et al., 1993, supra) and d($CGCA_3T_3GCG$ (SEQ ID NO:3))$_2$: 6b (9.2–9.6 Å) shows an increase of 0.4–3.1 Å.

There is some variability in the positioning of ligands within the minor groove of B-DNA even when there is a common motif such as the "flat sickle-shape" of 6b, 5c, and distamycin. Thus, the amide nitrogens of 6b are embedded to a distance of 3.1–4.5 Å from the floor of the groove.

The crystal structure of the d($CGCA_3T_3GCG$ (SEQ ID NO:3))$_2$: distamycin complex (Coll et al., 1987, supra) shows distamycin penetrating to within 4.2–4.5 Å from the bottom of the minor groove.

Examination of FIGS. 13A–C shows how the positively charged dimethylpropylamino tail ($R_3$) of 6b resides at a position which is adjacent to the $C_{11}O2$ and O4' in the minor groove while the protonated tren moiety is paired with the phosphates of $T_9$ and $G_{10}$. The three primary amines of 6b's tren amino substituent are located within 1.75 Å of two phosphodiester oxyanions while the fourth amine (tertiary) is 3.0 Å from the same two adjacent phosphodiester oxyanions.

The binding of distamycin in the minor groove is enhanced by its amidine tail forming bifurcated hydrogen bonds to the bottom of the minor groove (Coll et al., 1987, supra).

Changing the amidine tail (—$CH_2CH_2C(=NH)NH_2$)} of the carboxyl terminus of distamycin to a (—$CH_2CH_2CH_2N(CH_3)_2$ group and the formyl substituent at the amino terminus to acetamide causes a decrease in the equilibrium constant for 1:1 complex formation with d($GGCGCA_3T_3GGCGG$)(SEQ ID NO:1)/d($CCGCCA_3T_3GCGCC$)(SEQ ID NO:2) from $4 \times 10^7$ for distamycin to $6 \times 10^6 M^{-1}$ (Browne et al., 1993, supra).

However, further change of the N-methyl group on its central pyrrole to include a four methylene linker and a tren polyamino side chain (6b) leads to a binding constant of $8 \times 10^8 M^{-1}$ to the same oligomer (He et al., 1993, supra). This increase from $6 \times 10^6$ to $8 \times 10^8 M^{-1}$ in the binding constant must be due to the electrostatic interactions of the polyamino side chain with the phosphodiester linkages (He, G.-X., supra, 1993).

The significance of the central polyamino groups of 6b can be seen when comparing the bending angle of the d($CGCA_3T_3GCG$ (SEQ ID NO:3))$_2$: 6b complex (22.2°) with the angles found in distamycin complexed (1:1 and 2:1) to d($CGCA_3T_3GCG$ (SEQ ID NO:3))$_2$ (13.9° and 11.3°, respectively; FIG. 14).

The molecular contact surface area between d($CGCA_3T_3GCG$ (SEQ ID NO:3))$_2$ and 6b is 518 Å$^2$ In the 1:1 complexes of the dodecamer d($CGCA_3T_3GCG$ (SEQ ID NO:3))$_2$ with 6b, 5c (Blaskó et al., 1993, supra), or distamycin (Pelton et al., 1990, supra), exchange is between two equivalent ($A_3T_3$) binding sites via the "flip-flop" mechanism. The rate constant for exchange (which equals the off-rate) for 6b (10° C.) is ca. 1.3 s$^{-1}$. This may be compared to 0.2 s$^{-1}$ for distamycin at 30° C. (Pelton et al., 1990, supra). Thus, the exchange rate with 6b at identical $A_3T_3$ sites appreciably exceeds that for distamycin.

What is claimed is:

1. A tripyrrole peptide having first, second, and third pyrrole rings, said peptide which binds DNA thereby prohibiting the binding of DNA with an enzyme that regulates DNA expression and/or replication, the peptide having a polyamine group attached to the nitrogen atom of the second pyrrole of the tripyrrole peptide and having the following characteristics:
   a. binds to the minor groove of DNA with an equilibrium constant of $>10^9$ M$^{-1}$; and
   b. incapable of alkylating the enzyme or DNA.

2. A triheterocyclic peptide having first, second, and third 5-member heterocyclic moieties, said peptide having the following formula:

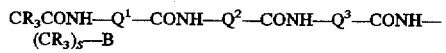

wherein $Q^1$ is selected from a group consisting of:

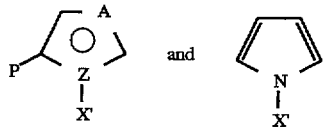

wherein $Q^2$ is selected from a group consisting of:

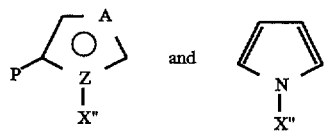

wherein $Q^3$ is selected from a group consisting of:

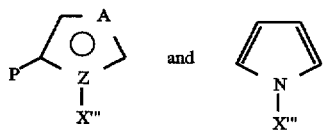

wherein at least one of A and Z is other than C;
wherein A is C, N, O, or S;
wherein B is $N(CR_3)_n$ or $C(NH_2)_2$;
wherein n is an integer from 2 to 10,
wherein P is H, a lower alkyl or a halogen;
wherein $Q^1$, $Q^2$, and $Q^3$ are the same or different;
wherein R is H or a lower alkyl group;

wherein S is an integer from 1 to 10;

wherein X' represents $CR_3$, $(CR_2)_n$—NRY, or $(CR_2)_n$—$CR_2Y$, wherein X" represents $CR_3$, $(CR_2)_n$—NRY, or $(CR_2)_n$—$CR_2Y$, and not $(CR_2)_n$—$N((CH_2)_3$—$N(CH_3)_2)_2$, wherein X'" represents $CR_3$, $(CR_2)_n$—NRY, or $(CR_2)_n$—$CR_2Y$, wherein Y is a polyamine group, and wherein Z is C or N;

wherein at least one of X', X", or X'" is other than $CR_3$.

3. A tripyrrole peptide having first, second, and third pyrrole rings, said peptide having the following formula:

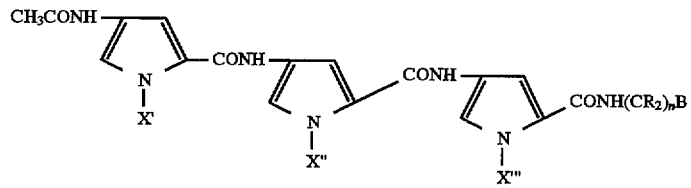

wherein B is $N(CR_3)_n$ or $C(NH_2)_2$;
wherein n is an integer from 2 to 10,
wherein R is H, a lower alkyl group, or halogen;
wherein X' represents $CR_3$, $(CR_2)_n$—NRY, or $(CR_2)_n$—$CR_2Y$, wherein X" represents $CR_3$, $(CR_2)_n$—NRY, or $(CR_2)_n$—$CR_2Y$, and not $(CR_2)_n$—$N((CH_2)_3$—$N(CH_3)_2)_2$, wherein X'" represents $CR_3$, $(CR_2)_n$—NRY, or $(CR_2)_n$—$CR_2Y$, wherein Y is a polyamine group, and wherein at least one of X', X", or X'" is other than $CR_3$.

4. The peptide of claim 1, 2 or 3, wherein the polyamine group is a moiety which binds the major groove of DNA through the phosphodiester linkage.

5. The peptide of claim 1, 2 or 3, wherein the binding is nonintercalative binding to DNA.

6. The peptide of claim 1, 2 or 3, wherein the polyamine group forms a complex with a metal ion.

7. The peptide of claim 1, 2 or 3, wherein the amino terminus of the peptide is acetylated.

8. The peptide of claim 1, 2 or 3, wherein the carboxyl terminus of the polypeptide has an amide linkage to β-(N, N-dimethylamino)propylamine.

9. The peptide of claim 1, 2 or 3, wherein the ring nitrogens of the first and third pyrrole rings are N-methylated.

10. The peptide of claim 1, 2 or 3, wherein the peptide binds the minor groove of DNA at A+T-rich regions of DNA.

11. The peptide of claim 1, 2 or 3, wherein the polyamine group includes four aliphatic amino groups.

12. The peptide of claim 2 or 3, wherein the polyamine group has the formula

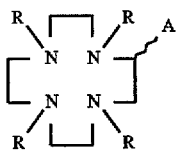

wherein A represents the attachment site.

13. The peptide of claim 2 or 3, wherein the polyamine group has the formula

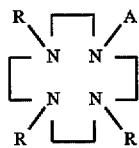

wherein A represents the attachment site.

14. The peptide of claim 2 or 3, wherein the polyamine group has the formula

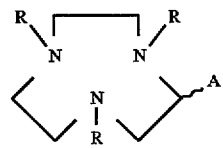

wherein A represents the attachment site.

15. The peptide of claim 2 or 3, wherein the polyamine group has the formula

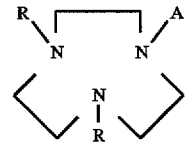

wherein A represents the attachment site.

16. The peptide of claim 2 or 3, wherein the polyamine group has the formula

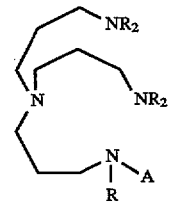

wherein A represents the attachment site.

17. The peptide of claim 2 or 3, wherein the polyamine group has the formula

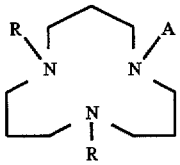

wherein A represents the attachment site.

18. The peptide of claim 2 or 3, wherein the polyamine group has the formula

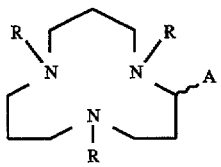

wherein A represents the attachment site.

19. The peptide of claim 2 or 3, wherein the polyamine group has the formula

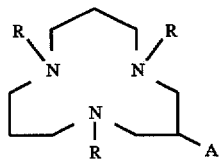

wherein A represents the attachment site.

20. The peptide of claim 2 or 3, wherein the polyamine group has the formula

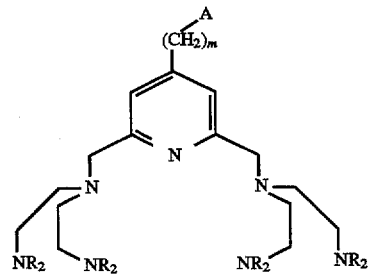

wherein A represents the attachment site; and wherein m is an integer from 1 to 5.

21. The peptide of claim 2 or 3, wherein the polyamine group has the formula

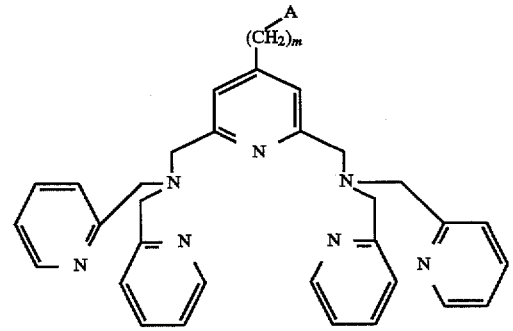

wherein A represents the attachment site; and wherein m is an integer from 1 to 5.

22. The peptide of claim 2 or 3, wherein the polyamine group has the formula

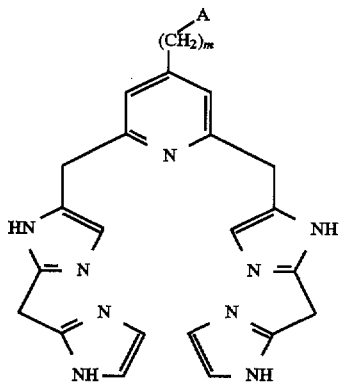

wherein A represents the attachment site; and wherein m is an integer from 1 to 5.

23. The peptide of claim 2 or 3, wherein the polyamine group has the formula

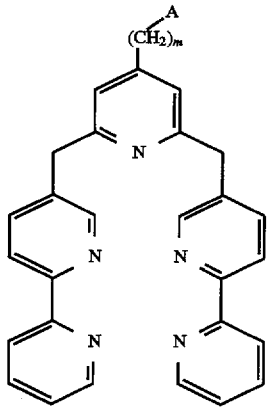

wherein A represents the attachment site; and wherein m is an integer from 1 to 5.

24. The tripyrrole peptide of claim 3, wherein a polyamine group is attached to the nitrogen atom of the first pyrrole of the tripyrrole peptide.

25. The tripyrrole peptide of claim 3, wherein a polyamine group is attached to the nitrogen atom of the second pyrrole of the tripyrrole peptide.

26. The tripyrrole peptide of claim 3, wherein a polyamine group is attached to the nitrogen atom of the third pyrrole of the tripyrrole peptide.

27. The peptide of claim 11, wherein two of the aliphatic amino groups are primary amino groups.

28. The peptide of claim 11, wherein one of the aliphatic amino groups is a secondary amino group.

29. The peptide of claim 11, wherein one of the aliphatic amino groups is a tertiary amino group.

30. The peptide of claim 24, 25, or 26, wherein the polyamine group has the formula —$(CH_2)_3NHCH_2CH_2N(CH_2CH_2NH_2)_2$.

31. The tripyrrole peptide of claim 25 which is a tren-microgonotropen molecule.

32. A tren-microgonotropen having the formula

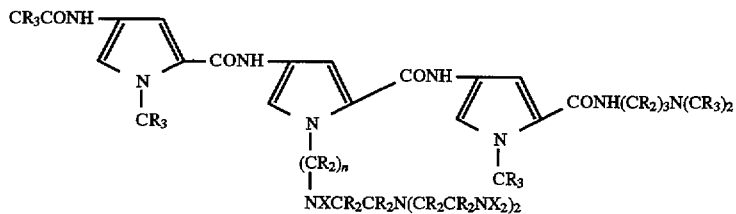

wherein n is 3, 4, or 5;

wherein R is a H, lower alkyl or a halogen; and wherein X is a H or lower alkyl.

* * * * *